US008227578B2

(12) United States Patent
Nakamura et al.

(10) Patent No.: US 8,227,578 B2
(45) Date of Patent: *Jul. 24, 2012

(54) ANTI-HUMAN DLK-1 ANTIBODY SHOWING ANTI-TUMOR ACTIVITY IN VIVO

(75) Inventors: Koji Nakamura, Tokyo (JP); Rie Tajima, Kanagawa (JP)

(73) Assignee: Abe, Ikubo & Katayama, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/514,230

(22) PCT Filed: Nov. 12, 2007

(86) PCT No.: PCT/JP2007/072335

§ 371 (c)(1),
(2), (4) Date: May 8, 2009

(87) PCT Pub. No.: WO2008/056833

PCT Pub. Date: May 15, 2008

(65) Prior Publication Data

US 2009/0326205 A1 Dec. 31, 2009

(30) Foreign Application Priority Data

Nov. 10, 2006 (JP) ................. 2006-305355

(51) Int. Cl.
*C07K 16/00* (2006.01)
(52) U.S. Cl. ............... 530/387.3; 530/387.9; 530/388.1; 530/389.1; 424/133.1
(58) Field of Classification Search ............... 530/387.3, 530/387.9, 388.1, 389.1; 424/133.1
See application file for complete search history.

(56) References Cited

U.S. PATENT DOCUMENTS

| 5,580,738 | A | 12/1996 | Laborda | |
|---|---|---|---|---|
| 5,644,031 | A | 7/1997 | Laborda | |
| 2003/0185815 | A1 | 10/2003 | Padigaru et al. | |
| 2004/0241170 | A1* | 12/2004 | Jensen et al. | 424/178.1 |
| 2005/0221392 | A1* | 10/2005 | Jensen et al. | 435/7.2 |
| 2008/0112956 | A1 | 5/2008 | Nakamura et al. | |
| 2009/0299038 | A1* | 12/2009 | Nakamura et al. | 530/387.3 |

FOREIGN PATENT DOCUMENTS

| EP | 1702982 A1 | 9/2006 |
|---|---|---|
| JP | 2001-269174 A | 10/2001 |
| JP | 2005-507236 A1 | 3/2005 |
| JP | 2006-516089 A1 | 6/2006 |
| WO | 02081625 A2 | 10/2002 |
| WO | WO-2004/030615 A2 | 4/2004 |
| WO | WO 2004/003019 * | 6/2004 |
| WO | WO-2005052156 A1 | 6/2005 |
| WO | 2009/116670 A1 | 9/2009 |

OTHER PUBLICATIONS

MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Luo et al. Hepatology 44(4):1012-1024 (Oct. 2006).*
"*dlk*, a Putative Mammalian Homeotic Gene Differentially Expressed in Small Cell Lung Carcinoma and Neuroendocrine Tumor Cell Line", by Laborda, J. et al., J. Biol.Chem., vol. 268 (6), p. 3817-3820 (1993).
"Pref-1, a Protein Containing EGF-like Repeats, Inhibits Adipocyte Differentiation", by Smas, C. M. et al., Cell, vol. 73 (4), p. 725-734 (1993).
"Molecular markers of neuroendocrine development and evidence of environmental regulation", by Helman, L. J. et al., Proc. Natl. Acad. Sci. USA, vol. 84, p. 2336-2339 (1987).
"*Mus musculus* SCP-1 mRNA for stromal cell derived protein-1, complete cds", by Maruyama et al., Unpublished, Genebank accession No. D16847 (1993).
"Cloning of a Membrane-Spanning Protein with Epidermal rowth Factor-Like Repeat Motifs from Adrenal Glomerulosa Cells", by Halder, S. K. et al., Endocrinology, vol. 139, p. 3316-3328 (1998).
"Two fetal antigens (FA-1 and FA-2) and endometrial proteins (PP12 and PP14) isolated from amniotic fluid; preliminary observations in fetal and maternal tissues", by Fay, T. N. et al., Eur. J. Obstet. Gynecol. Reprod. Biol., vol. 29, p. 73-85 (1988).
"Expression of Dlk/Pref-1 defines a subpopulation in the oval cell compartment of rat liver", by Tanimizu, N. et al., Gene Expression Patterns, vol. 5, p. 209-218 (2004).
"Transit-Amplifying Ductular (Oval) Cells and Their Hepatocytic Progeny Are Characterized by a Novel and Distinctive Expression of Delta-Like Protein/Preadipocyte Factor 1/Fetal Antigen 1", by Jensen, C. H. et a!., Am. J. Pathol., vol. 164 (4), p. 1347-1359 (2004).
"Regulation of Human Skeletal Stem Cells Differentiation by Dlk 1/Pref-1" by Abdallah, RM. et al., J. Bone Miner. Res., vol. 19 (5), p. 841-852 (2004).

(Continued)

*Primary Examiner* — Lynn Bristol
(74) *Attorney, Agent, or Firm* — McDermott Will & Emery LLP; Paul M. Zagar

(57) ABSTRACT

The present invention provides an antibody specifically against hDlk-1 and having anti-tumor activity in vivo (an anti-hDlk-1 antibody), a fragment of the antibody, a hybridoma that produces the antibody, a complex of the antibody or antibody fragment and an agent, a pharmaceutical composition comprising the antibody and the like, a tumor therapeutic agent, a tumor angiogenesis inhibitor, a tumor diagnostic agent, a method for detecting a tumor, a kit for detecting and/or diagnosing a tumor, etc.

12 Claims, 33 Drawing Sheets

OTHER PUBLICATIONS

"Fetal antigen 1, a member of the epidermal growth factor superfamily in neurofibromas and serum from patients with neurofibromatosis type 1", by Jensen, C. H. et al., Br. J. Dermatol., vol. 140 (6), p. 1054-1059 (1999).

"Elevated Serum Levels of Fetal Antigen 1, a Member of the Epidermal Growth Factor Superfamily, in Patients with Small Cell Lung Cancer", by Jensen, C.H. et al., Tumour Biol., vol. 20 (5), p. 256-262 (1999).

"Imprinting status of DLK1 gene in brain tumors and lymphomas" by Yin, D. et al., Int. J. Oncol., vol. 24 (4), p. 1011-1015 (2004).

"DLK1: increased expression in gliomas and associated with oncogenic activities", by Yin, D. et al., Oncogene, vol .25 (13), p. 1852-1861 (2006).

"Imprinting, expression and localisation of DLK1 in Wilms tumours", by Fukuzawa, R. et al., J. Clin. Pathol., vol. 58, p. 145-150 (2006).

"Identification of myelodysplastic syndrome-specific genes by DNA microarray analysis with purified hematopoietic stem cell fraction", by Miyazato, A. et al., Blood, vol. 98, p. 422-427 (2001).

"Dlk 1 in normal and abnormal hematopoiesis", by Sakajiri, S. et al., Leukemia, vol. 19 (8), p. 1404-1410 (2005).

"Antibody engineering, A Practical Approach", by Djavadi-Ohaniance L. et al. (1996), In Antibody Engineering, Chapter 4, pp. 77-97. IRL Press, Oxford.

"Protein structure of fetal antigen 1 (FA1), A novel circulating human epidermal-growth-factor0like protein expressed in neuroendocrine tumors and its relation to the gene products of dlk and pG2", by Jensen, C. H. et al., European Journal of Biochemistry, vol. 225, p. 83-92 (1994).

"A Role foor Pref-1 and HES-1 in Thymocyte Development", by Kaneta, M. et al., Journal of Immunology, vol. 164, p. 256-264 (2000).

"Isolation of hepatoblasts based on the expression of Dlk/Pref-1", by Tanimizu, N. et al., Journal of Cell Science, vol. 116, p. 1775-1786 (2003).

"Membrane protein of hepatic stem cell as molecular target for liver cancer", by Atushi Miyajima et al., Abstracts of the 45th General Meeting of Japan Society of Clinical Oncology (Sep. 20, 2007), vol. 42 (2), p. 212 with its English translation.

Patrick Dufner, et al., Harnessing phage and ribosome display for antibody optimisation, Trends in Biotechnology, vol. 24, No. 11, pp. 523-529, 2006.

* cited by examiner

Fig. 1
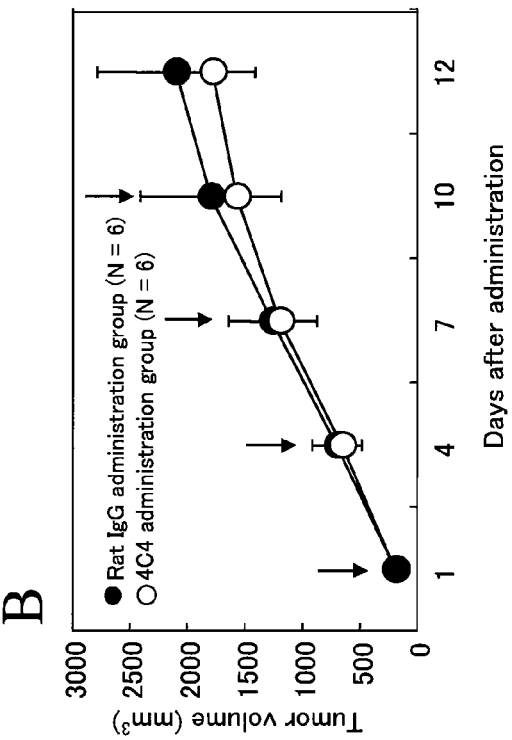
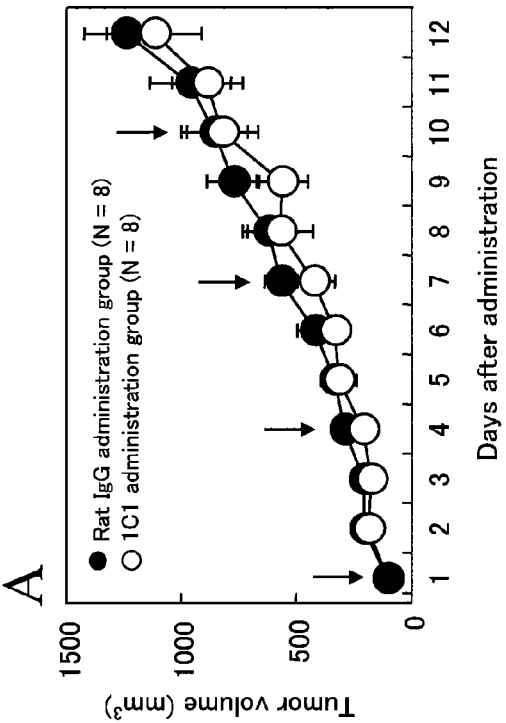
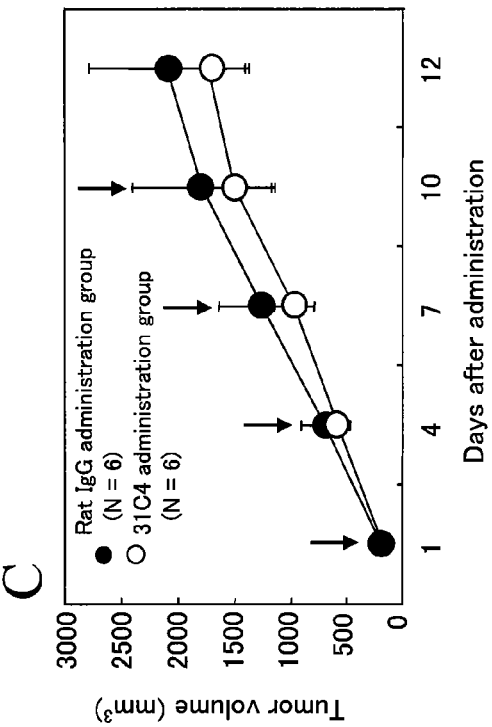

Fig. 14
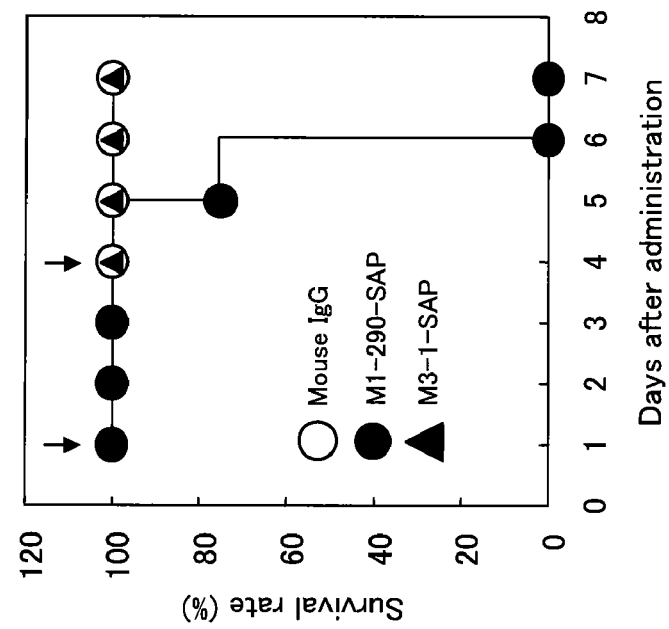
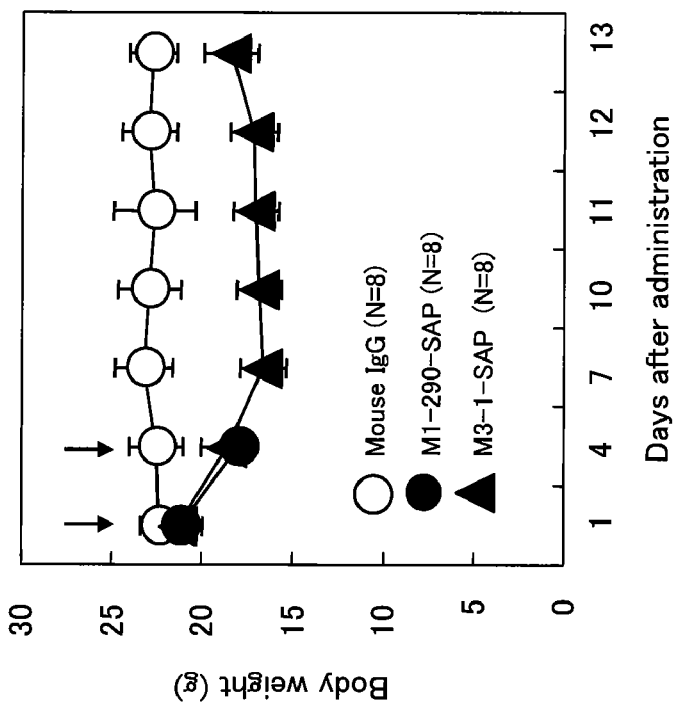

Fig. 21

ATGAAATGCAGCTGGGTTATCTTCTTCCTGATGGCAGTGGTTACAGGGGTCAATTCAGAG
 M   K   C   S   W   V   I   F   F   L   M   A   V   V   T   G   V   N   S   <u>E</u>

GTTCAGCTGCAGCAGTCTGGGGCAGAGCTTGTGAAGCCAGGGGCCTCAGTCAAGTTGTCC
 V   Q   L   Q   Q   S   G   A   E   L   V   K   P   G   A   S   V   K   L   S

TGCACAGCTTCTGGCTTCAACATTAGAGACACCTATATACACTGGGTGAAGCAGAGGCCT
 C   T   A   S   G   F   N   I   R   <u>D   T   Y   I   H</u>   W   V   K   Q   R   P

GAGCAGGGCCTGGAGTGGATTGGAAGGATTGATCCTCCGAATGGTAATCTTAAATATGAC
 E   Q   G   L   E   W   I   G   <u>R   I   D   P   P   N   G   N   L   K   Y   D</u>

CCGAAGTTCCAGGGCAAGGCCACTATAACAGCAGACACATCCTCCAACACAGCCTACCTG
 <u>P   K   F   Q   G</u>   K   A   T   I   T   A   D   T   S   S   N   T   A   Y   L

CAGTTCAGCAGCCTGACATCTGAGGACACTGCCGTCTATTACTGTGCAAGGTCTGATGGT
 Q   F   S   S   L   T   S   E   D   T   A   V   Y   Y   C   A   R   <u>S   D   G</u>

TACTCCTTTGCTTACTGGGGCCAAGGGACTCTGGTCACTGTCTCTGCAGCC
 <u>Y   S   F   A   Y</u>   W   G   Q   G   T   L   V   T   V   S   A   A

Fig. 22

ATGAGGTGCCTAGCTGAGTTCCTGGGGCTGCTTGTGCTCTGGATCCCTGGAGCCATTGGG
 M   R   C   L   A   E   F   L   G   L   L   V   L   W   I   P   G   A   I   G

GATATTGTGATGACTCAGGCTGCACCCTCTGTACCTGTCACTCCTGGAGAGTCAGTATCC
 <u>D</u>   I   V   M   T   Q   A   A   P   S   V   P   V   T   P   G   E   S   V   S

ATCTCCTGCAGGTCTAGTAAGAGTCTCCTGCATAGTAATGGCAACACTTACTTGTATTGG
 I   S   C   <u>R   S   S   K   S   L   L   H   S   N   G   N   T   Y   L   Y</u>   W

TTCCTGCAGAGGCCAGGCCAGTCTCCTCAGCTCCTGATATATCGGATGTCCAACCTTGCC
 F   L   Q   R   P   G   Q   S   P   Q   L   L   I   Y   <u>R   M   S   N   L   A</u>

TCAGGAGTCCCAGACAGGTTCAGTGGCAGTGGGTCAGGAACTGCTTTCACACTGAGAATC
 <u>S</u>   G   V   P   D   R   F   S   G   S   G   S   G   T   A   F   T   L   R   I

AGTAGAGTGGAGGCTGAGGATGTGGGTGTTTATTACTGTATGCAACATGTAGAATATCCA
 S   R   V   E   A   E   D   V   G   V   Y   Y   C   <u>M   Q   H   V   E   Y   P</u>

TTCACGTTCGGCTCGGGGACAAAGTTGGAAATAAAA
 <u>F   T</u>   F   G   S   G   T   K   L   E   I   K

Fig. 23

SpeI
ACTAGTACCACCATGAAATGCAGCTGGGTTATCTTCTTCCTGATGGCAGTGGTTACAGGG
            M  K  C  S  W  V  I  F  F  L  M  A  V  V  T  G

GTCAATTCAGAGGTTCAGCTGCAGCAGTCTGGGGCAGAGCTTGTGAAGCCAGGGGCCTCA
 V  N  S  E  V  Q  L  Q  Q  S  G  A  E  L  V  K  P  G  A  S

GTCAAGTTGTCCTGCACAGCTTCTGGCTTCAACATTAGAGACACCTATATACACTGGGTG
 V  K  L  S  C  T  A  S  G  F  N  I  R  D  T  Y  I  H  W  V

AAGCAGAGGCCTGAGCAGGGCCTGGAGTGGATTGGAAGGATTGATCCTCCGAATGGTAAT
 K  Q  R  P  E  Q  G  L  E  W  I  G  R  I  D  P  P  N  G  N

CTTAAATATGACCCGAAGTTCCAGGGCAAGGCCACTATAACAGCAGACACATCCTCCAAC
 L  K  Y  D  P  K  F  Q  G  K  A  T  I  T  A  D  T  S  S  N

ACAGCCTACCTGCAGTTCAGCAGCCTGACATCTGAGGACACTGCCGTCTATTACTGTGCA
 T  A  Y  L  Q  F  S  S  L  T  S  E  D  T  A  V  Y  Y  C  A

AGGTCTGATGGTTACTCCTTTGCTTACTGGGGCCAAGGGACTCTGGTCACTGTCTCTGCA
 R  S  D  G  Y  S  F  A  Y  W  G  Q  G  T  L  V  T  V  S  A

HindIII
*GGTGAGTCCTAACTTCAAGCTT*

Fig. 24

NheI
GCTAGCACCACCATGAGGTGCCTAGCTGAGTTCCTGGGGCTGCTTGTGCTCTGGATCCCT
          M   R   C   L   A   E   F   L   G   L   L   V   L   W   I   P

GGAGCCATTGGGGATATTGTGATGACTCAGGCTGCACCCTCTGTACCTGTCACTCCTGGA
 G   A   I   G   D   I   V   M   T   Q   A   A   P   S   V   P   V   T   P   G

GAGTCAGTATCCATCTCCTGCAGGTCTAGTAAGAGTCTCCTGCATAGTAATGGCAACACT
 E   S   V   S   I   S   C   R   S   S   K   S   L   L   H   S   N   G   N   T

TACTTGTATTGGTTCCTGCAGAGGCCAGGCCAGTCTCCTCAGCTCCTGATATATCGGATG
 Y   L   Y   W   F   L   Q   R   P   G   Q   S   P   Q   L   L   I   Y   R   M

TCCAACCTTGCCTCAGGAGTCCCAGACAGGTTCAGTGGCAGTGGGTCAGGAACTGCTTTC
 S   N   L   A   S   G   V   P   D   R   F   S   G   S   G   S   G   T   A   F

ACACTGAGAATCAGTAGAGTGGAGGCTGAGGATGTGGGTGTTTATTACTGTATGCAACAT
 T   L   R   I   S   R   V   E   A   E   D   V   G   V   Y   Y   C   M   Q   H

GTAGAATATCCATTCACGTTCGGCTCGGGGACAAAGTTGGAAATAAAAC*GTAAGTAGACT*
 V   E   Y   P   F   T   F   G   S   G   T   K   L   E   I   K

EcoRI
*TTTGCGAATTC*

ANTI-HUMAN DLK-1 ANTIBODY SHOWING ANTI-TUMOR ACTIVITY IN VIVO

CROSS-REFERENCE TO PRIOR APPLICATION

This is the U.S. National Phase Application under 35 U.S.C. §371 of International Patent Application No. PCT/JP2007/072335 filed Nov. 12, 2007, which claims the benefit of Japanese Patent Application No. 2006-305355 filed Nov. 10, 2006, both of them are incorporated by reference herein. The International Application was published in Japanese on May 15, 2008 as WO 2008/056833 A1 under PCT Article 21(2).

TECHNICAL FIELD

The present invention relates to anti-human Dlk-1 antibodies having anti-tumor activity and particularly to anti-human Dlk-1 antibodies having anti-tumor activity in vivo. In addition, the present invention also relates to hybridomas that produce the aforementioned antibodies and a use of the aforementioned antibodies.

BACKGROUND ART

Human Dlk-1 (delta-like 1 homolog (*Drosophila*); which may be hereinafter referred to as "hDlk-1") is a type I transmembrane (one-transmembrane-type) protein with a full length of 383 amino acid residues which has 6 EGF-like motifs in its extracellular region. The extracellular region shows homology with a Notch/Delta/Serrate family. A hDlk-1 gene has been cloned as a molecule expressed in a GRP (gastrin releasing peptide)-responsive lung small cell carcinoma-derived cell line (Non-Patent Document 1), or as a factor for suppressing preadipocyte differentiation (Non-Patent Document 2). From the viewpoint of the homology of the amino acid sequence of hDlk-1 with that of Delta that is a ligand of a Notch receptor as a cell differentiation regulator, such Dlk-1 is generally referred to as a gene symbol, DLK1. It also has several other gene symbols such as Pref-1 (Non-Patent Document 2), pG2 (Non-Patent Document 3), SCP-1 (Non-Patent Document 4) and ZOG (Non-Patent Document 5). However, these gene symbols basically indicate the same molecule.

Moreover, hDlk-1 is cleaved with an unidentified protease which cuts the neighborhood of cell membrane in the extracellular region of hDlk-1, and it is then secreted into blood. Free hDlk-1 (hDlk-1 extracellular region) is a molecule identical to a glycoprotein called FA-1 (Fetal antigen-1) (Non-Patent Document 6) consisting of 225 to 262 amino acid residues.

The hDlk-1 gene and a gene product thereof are expressed at a high level in undifferentiated, highly proliferative, fetal cells. In particular, the hDlk-1 gene and the gene product thereof are highly expressed in fetal liver, fetal kidney, fetal skeletal muscle, fetal brain and the like. After birth, however, expression of such a hDlk-1 gene and a gene product thereof can not be observed in most of the tissues. In normal adult tissues, the hDlk-1 gene and the gene product thereof are localized in adrenal gland, placenta and hypophysis (Patent Document 1, Non-Patent Document 2).

Furthermore, even in mature tissues, expression of hDlk-1 is observed in cells that are considered to be undifferentiated stem cells or precursor cells. For example, it has been reported that expression of hDlk-1 has been observed in hepatic oval cells that are undifferentiated and have pluripotency in adult liver (Non-Patent Documents 7 and 8) or in mesenchymal stem cells that are the stem cells of bone/cartilage/adipose cells (Non-Patent Document 9). It has been suggested that hDlk-1 is associated with the properties of such tissue stem cells, such as the maintenance of undifferentiation ability.

Such an expression pattern of hDlk-1 localized in fetal cells or stem cells and a family of genes/gene products having EGF-like motifs (Notch-receptor, Notch ligand (Delta, Jagged, serrate), etc.) generally controls the growth or differentiation of cells by intercellular interaction via EGF-like motifs. Thus, it has been suggested that hDlk-1 also has such functions. In fact, it has been well known that expression of hDlk-1 is decreased concomitant with differentiation of adipose precursor cells and that adipose differentiation is suppressed, if the hDlk-1 gene is forced to express in adipose precursor cells (Non-Patent Document 2). However, at the present time, details regarding a molecule (a ligand) interacting with hDlk-1 are unknown.

On the other hand, it has been reported that the hDlk-1 gene and the gene product thereof are expressed with a high frequency in various types of cancers or tumors. The types of cancers, in which expression of hDlk-1 has been confirmed so far, include: solid cancers such as neuroendocrine tumor, neuroblastoma, glioma, neurofibromatosis type 1, small cell lung cancer, liver cancer, kidney cancer and ovarian cancer (Patent Documents 1 and 2 and Non-Patent Documents 1, 3, 10, 11, 12, 13 and 14); and blood cancers such as myelodysplastic syndrome (Patent Document 3 and Non-Patent Documents 15 and 16) and acute myelocytic leukemia (Non-Patent Document 16). It has been reported that cell growth is accelerated if a hDlk-1 gene is introduced into a K562 cell that is an erythroleukemia cell line (Non-Patent Document 16) and also that, if such a hDlk-1 gene is introduced into glioblastomas, it causes the disappearance of contact inhibition of cells as well as acceleration of cell growth, so that anchorage-independent cell growth ability can be achieved. The relationship between hDlk-1 and carcinogenesis has been suggested (Non-Patent Document 17).

<Patent Documents>
Patent Document 1: WO 2005/052156
Patent Document 2: WO 02/081625
Patent Document 3: Japanese Patent Laid-Open No. 2001-269174

<Non-Patent Documents>
Non-Patent Document 1: Laborda, J. et al., J. Biol. Chem., vol. 268 (6), pp. 3817-3820 (1993)
Non-Patent Document 2: Smas, C. M. et al., Cell, vol. 73 (4), pp. 725-734 (1993)
Non-Patent Document 3: Helman, L. J. et al., Proc. Natl. Acad. Sci. USA, vol. 84, pp. 2336-2339 (1987)
Non-Patent Document 4: Maruyama, K. et al., Unpublished, Genebank accession number D16847 (1993)
Non-Patent Document 5: Halder, S. K. et al., Endocrinology, vol. 139, pp. 3316-3328 (1998)
Non-Patent Document 6: Fay, T. N. et al., Eur. J. Obstet. Gynecol. Reprod. Biol., vol. 29, pp. 73-85 (1988)
Non-Patent Document 7: Tanimizu, N. et al., Gene Expression Patterns, vol. 5, pp. 209-218 (2004)
Non-Patent Document 8: Jensen, C H. et al., Am. J. Pathol., vol. 164 (4), pp. 1347-1359 (2004)
Non-Patent Document 9: Abdallah, B. M. et al., J. Bone Miner. Res., vol. 19 (5), pp. 841-852 (2004)
Non-Patent Document 10: Jensen, C. H. et al., Br. J. Dermatol., vol. 140 (6), pp. 1054-1059 (1999)
Non-Patent Document 11: Jensen, C. H. et al., Tumour Biol., vol. 20 (5), pp. 256-262 (1999)

Non-Patent Document 12: Yin, D. et al., Int. J. Oncol., vol. 24 (4), pp. 1011-1015 (2004)
Non-Patent Document 13: Yin, D. et al., Oncogene, vol. 25 (13), pp. 1852-1861 (2006)
Non-Patent Document 14: Fukuzawa, R. et al., J. Clin. Pathol., vol. 58, pp. 145-150 (2006)
Non-Patent Document 15: Miyazato, A. et al., Blood, vol. 98, pp. 422-427 (2001)
Non-Patent Document 16: Sakajiri, S. et al., Leukemia, vol. 19 (8), pp. 1404-1410 (2005)
Non-Patent Document 17: Yin, D. et al., Oncogene, vol. 25 (13), pp. 1852-1861 (2006)

DISCLOSURE OF THE INVENTION

As described above, in the case of normal tissues, expression of hDlk-1 is localized in embryonic cells or stem cells. However, in the case of cancer tissues, hDlk-1 is expressed with a high frequency in various types of cells. Such hDlk-1 is a cell membrane protein/secretory protein. Based on these facts, hDlk-1 is considered to become a good target in the treatment of various types of tumors, etc. When such hDlk-1 is targeted, an anti-hDlk-1 antibody is considered to be useful.

Thus, an object of the present invention is to provide an anti-human Dlk-1 antibody having anti-tumor activity and in particular, an anti-human Dlk-1 monoclonal antibody having anti-tumor activity in vivo. Moreover, another object of the present invention is to provide a hybridoma that produces the aforementioned antibody, a complex of the aforementioned antibody and an agent, a pharmaceutical composition for diagnosing or treating a tumor, a method for detecting a tumor and a kit for detecting or diagnosing a tumor.

The present inventors have conducted intensive studies directed towards achieving the aforementioned objects. As a result, the inventors have found an antibody that specifically reacts with human Dlk-1 (particularly, an anti-human Dlk-1 monoclonal antibody) and has anti-tumor activity and a complex (an immunoconjugate) of the antibody and various types of agents. The inventors have then confirmed that such an antibody and a complex have anti-tumor activity in vivo. Furthermore, the present inventors have also found that such an antibody and a complex are useful for the treatment, diagnosis and detection of a tumor, thereby completing the present invention.

That is to say, the present invention is as follows.
(1) An antibody against human Dlk-1, which has anti-tumor activity in vivo.

The above-described tumor is at least one type selected from the group consisting of human colon cancer, human breast cancer, human liver cancer and human neuroblastoma, for example.

The anti-tumor activity of the antibody according to (1) above is tumor angiogenesis-inhibiting activity, for example.

The antibody according to (1) above is a polyclonal antibody or a monoclonal antibody, for example.

For example, the antibody according to (1) above includes: an antibody wherein the amino acid sequences of CDRs 1 to 3 of the H chain V region are the amino acid sequences as shown in SEQ ID NOS: 30 to 32, respectively; and/or an antibody wherein the amino acid sequences of CDRs 1 to 3 of the L chain V region are the amino acid sequences as shown in SEQ ID NOS: 33 to 35, respectively.

The antibody of the present invention includes an antibody produced by a hybridoma, a genetically recombinant antibody, etc.

The term "hybridoma" is used herein to mean cells producing an antibody having desired antigenic specificity, which are formed by cell fusion between B cells obtained by immunizing mammals other than humans with an antigen and myeloma cells.

The genetically recombinant antibody includes antibodies produced by gene recombination, such as a chimeric antibody (a humanized chimeric antibody), a humanized antibody, a human antibody and an antibody fragment thereof. A genetically recombinant antibody, which has characteristics as a monoclonal antibody, has low antigenecity and has a prolonged half-life in blood, is preferably used as a therapeutic agent. Herein, an example of the chimeric antibody is an antibody whose amino acid sequence of the H chain V region comprises the amino acid sequence as shown in SEQ ID NO: 23 and whose amino acid sequence of the L chain V region comprises the amino acid sequence as shown in SEQ ID NO: 25.

(2) A monoclonal antibody against human Dlk-1, which is produced by a hybridoma having accession No. FERM BP-10707.
(3) A monoclonal antibody against human Dlk-1, which is produced by a hybridoma having accession No. FERM BP-10899.
(4) A monoclonal antibody against human Dlk-1, which is produced by a hybridoma having accession No. FERM BP-10900.

An example of the antibodies according to (1) to (4) above is an antibody, which binds to (recognizes) at least a portion of a region comprising amino acids at positions 26 to 85, a region comprising amino acids at positions 92 to 167, or a region comprising amino acids at positions 131 to 244, in the amino acid sequence of human Dlk-1 as shown in SEQ ID NO: 2.

(5) An example of the antibodies according to (1) to (4) above is an antibody, which binds to a site (e.g. an epitope), to which a monoclonal antibody produced by the hybridoma having accession No. FERM BP-10707, FERM BP-10899, or FERM BP-10900 binds (recognizes).

(6) An antibody fragment derived from the antibody according to any one of (1) to (5) above.

Examples of the antibody fragment according to (6) above include those comprising the amino acid sequences as shown in SEQ ID NOS: 30 to 32. A specific example of the antibody fragment is an antibody fragment comprising the amino acid sequence as shown in SEQ ID NO: 23.

Examples of the antibody fragment according to (6) above include those comprising the amino acid sequences as shown in SEQ ID NOS: 33 to 35. A specific example of such an antibody fragment is an antibody fragment comprising the amino acid sequence as shown in SEQ ID NO: 25.

(7) A hybridoma, which produces the antibody according to (1) above.

A hybridoma producing a monoclonal antibody against human Dlk-1, which has accession No. FERM BP-10707 (deposited Oct. 18, 2006, International Patent Organism Depository, National Institute of Advanced Industrial Science and Technology, AIST Tsukuba Central 6, 1-1, Higashi 1-chome Tsukuba-shi, Ibaraki-ken 305-8566, Japan).

A hybridoma producing a monoclonal antibody against human Dlk-1, which has accession No. FERM BP-10899 (deposited Aug. 21, 2007, International Patent Organism Depository, National Institute of Advanced Industrial Science and Technology, AIST Tsukuba Central 6, 1-1, Higashi 1-chome Tsukuba-shi, Ibaraki-ken 305-8566, Japan).

A hybridoma producing a monoclonal antibody against human Dlk-1, which has accession No. FERM BP-10900 (deposited Aug. 21, 2007, International Patent Organism Depository, National Institute of Advanced Industrial Science and Technology, AIST Tsukuba Central 6, 1-1, Higashi 1-chome Tsukuba-shi, Ibaraki-ken 305-8566, Japan).
(11) An antibody-agent complex, which comprises the antibody according to any one of (1) to (5) above and a compound having anti-tumor activity and/or cell-killing activity.
(12) An antibody-agent complex, which comprises the antibody fragment according to (6) above and a compound having anti-tumor activity and/or cell-killing activity.

In the complexes according to (11) and (12) above, the tumor is at least one type selected from the group consisting of human colon cancer, human breast cancer, human liver cancer and human neuroblastoma, for example.

In the complexes according to (11) and (12) above, the anti-tumor activity is tumor angiogenesis-inhibiting activity, for example.
(13) A pharmaceutical composition, which comprises the antibody according to any one of (1) to (5) above, the antibody fragment according to (6) above and the complex according to (11) or (12) above.

The composition according to (13) above is used in the treatment of tumor, for example. The treatment of tumor indicates inhibition of tumor angiogenesis, for example. In addition, an example of the above-described composition is a composition, which does not cause weight reduction as a side effect.

The composition according to (13) above is used in the diagnosis of tumor, for example.

In the composition according to (13) above, the tumor is at least one type selected from the group consisting of human colon cancer, human breast cancer, human liver cancer and human neuroblastoma, for example.
(14) A tumor therapeutic agent, which comprises at least one type selected from the group consisting of the antibody according to any one of (1) to (5) above, the antibody fragment according to (6) above and the complex according to (11) or (12) above.

An example of the therapeutic agent according to (14) above is a therapeutic agent, which does not cause weight reduction as a side effect.

In the therapeutic agent according to (14) above, the tumor is at least one type selected from the group consisting of human colon cancer, human breast cancer, human liver cancer and human neuroblastoma, for example.
(15) A tumor angiogenesis inhibitor, which comprises at least one type selected from the group consisting of the antibody according to any one of (1) to (5) above, the antibody fragment according to (6) above and the complex according to (11) or (12) above.

An example of the inhibitor according to (15) above is an inhibitor, which does not cause weight reduction as a side effect.

In the inhibitor according to (15) above, the tumor is at least one type selected from the group consisting of human colon cancer, human breast cancer, human liver cancer and human neuroblastoma, for example.
(16) A tumor diagnostic agent, which comprises at least one type selected from the group consisting of the antibody according to any one of (1) to (5) above, the antibody fragment according to (6) above and the complex according to (11) or (12) above.

In the diagnostic agent according to (16) above, the tumor is at least one type selected from the group consisting of human colon cancer, human breast cancer, human liver cancer and human neuroblastoma, for example.
(17) A method for detecting a tumor, which comprises: allowing at least one type selected from the group consisting of the antibody according to (1) to (5) above, the antibody fragment according to (6) above and the complex according to (11) or (12) above, to react with a sample collected from a living body; and detecting a signal of the reacted antibody.

The above-described tumor is at least one type selected from the group consisting of human colon cancer, human breast cancer, human liver cancer and human neuroblastoma, for example.
(18) A method for diagnosing and/or treating a tumor, which comprises administering to a patient, at least one type selected from the group consisting of the antibody according to any one of (1) to (5) above, the antibody fragment according to (6) above and the complex according to (11) or (12) above, or the pharmaceutical composition according to (13) above.

The above-described tumor is at least one type selected from the group consisting of human colon cancer, human breast cancer, human liver cancer and human neuroblastoma, for example.

An example of the method according to (18) above is a method for treating a tumor by inhibiting or suppressing the angiogenesis of the tumor.
(19) The antibody according to any one of (1) to (5) above, the antibody fragment according to (6) above, or the complex according to (11) or (12) above, which is used in the diagnosis and/or treatment of the tumor.

The above-described tumor is at least one type selected from the group consisting of human colon cancer, human breast cancer, human liver cancer and human neuroblastoma, for example.
(20) A use of the antibody according to any one of (1) to (5) above, the antibody fragment according to (6) above, or the complex according to (11) or (12) above, in production of a pharmaceutical for diagnosing and/or treating the tumor.

The above-described tumor is at least one type selected from the group consisting of human colon cancer, human breast cancer, human liver cancer and human neuroblastoma, for example.
(21) A kit for detecting, diagnosing, or treating a tumor, which comprises at least one type selected from the group consisting of the antibody according to any one of (1) to (5) above, the antibody fragment according to (6) above and the complex according to (11) or (12) above.

The above-described tumor is at least one type selected from the group consisting of human colon cancer, human breast cancer, human liver cancer and human neuroblastoma, for example.

BRIEF DESCRIPTION OF DRAWINGS

FIG. 1 shows the results obtained by administering 3 clones (1C1, 4C4 and 31C4) of a known anti-hDlk-1 monoclonal antibody (WO 2005/052156) to Xenograft Treatment models using a hDlk-1-expressing liver cancer cell line (Huh-7-hDlk cells). Each antibody was intraperitoneally administered to the model total 4 times (indicated with the arrows in the figures), namely, on the $1^{st}$ day (Day 1), $4^{th}$ day (Day 4), $7^{th}$ day (Day 7) and $10^{th}$ day (Day 10).

FIG. 1A: Rat IgG (control group) (●), 1C1 (○)
FIG. 1B: Rat IgG (control group) (●), 4C4 (○)
FIG. 1C: Rat IgG (control group) (●), 31C4 (○)

In each of FIGS. 1A to 1C, the number of mice in each group was represented by N and each measurement value (tumor volume) was represented by a mean value±standard error. At least 3 independent experiments were carried out in each case. In all cases, there was observed no anti-tumor activity to liver cancer that had been established subcutaneously in nude mice.

Figure 2:
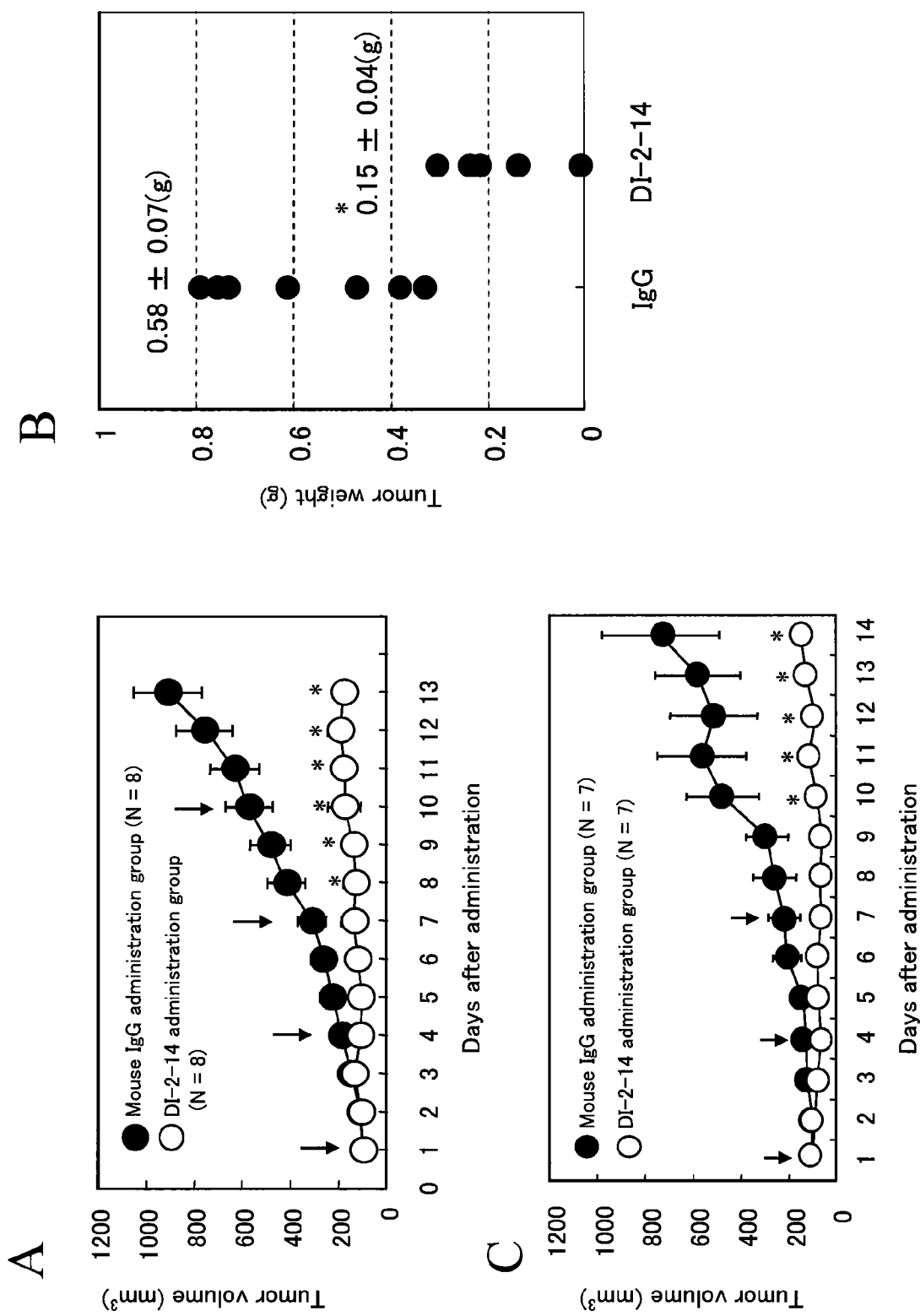

FIG. 2 shows evaluation of the anti-tumor activity of a novel anti-hDlk-1 monoclonal antibody clone DI-2-14 (mouse IgG1) on Xenograft Treatment models using Huh-7-hDlk-cells.

FIG. 2A: Tumor growth in a control group (mouse IgG) and a DI-2-14 administration group was indicated with the time elapsed (a mean value±standard error). The arrow indicates administration of the antibody (20 mg/kg body weight, intraperitoneal administration). *$P<0.01$ (by Student's t-test)

FIG. 2B: A figure obtained by plotting the tumor weight of each mouse at the time of the $14^{th}$ day (Day 14) (the final day of the experiment) in the test of FIG. 2A above. The numerical value described on each plot indicates a mean value±standard error. *$P<0.01$ (by Student's t-test)

FIG. 2C: The results obtained by evaluating the anti-tumor activity of DI-2-14 in another independent experiment. *$P<0.01$ (by Student's t-test)

Figure 3:
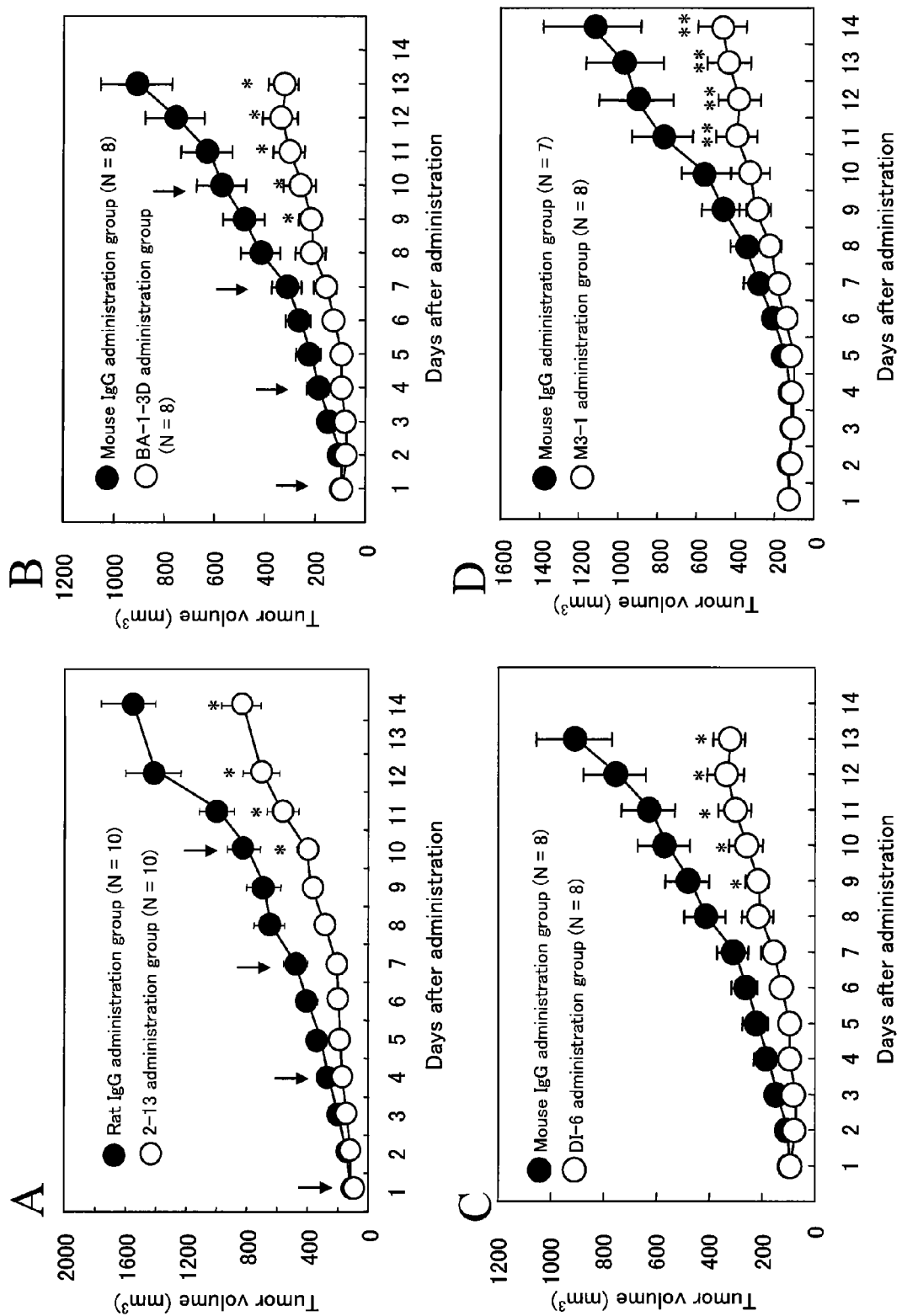

FIG. 3 shows evaluation of the anti-tumor activity of A: clone 2-13 (rat IgG2b), B: clone BA-1-3D (mouse IgG2a), C: clone DI-6 (mouse IgG1) and D: clone M3-1 (mouse IgG1), on Xenograft Treatment models using Huh-7-hDlk cells. The tumor volume is indicated by a mean value±standard error. The asterisk shows the results of a significant difference test (*$P<0.01$, **$P<0.05$ by Student's-t-test).

Figure 4:
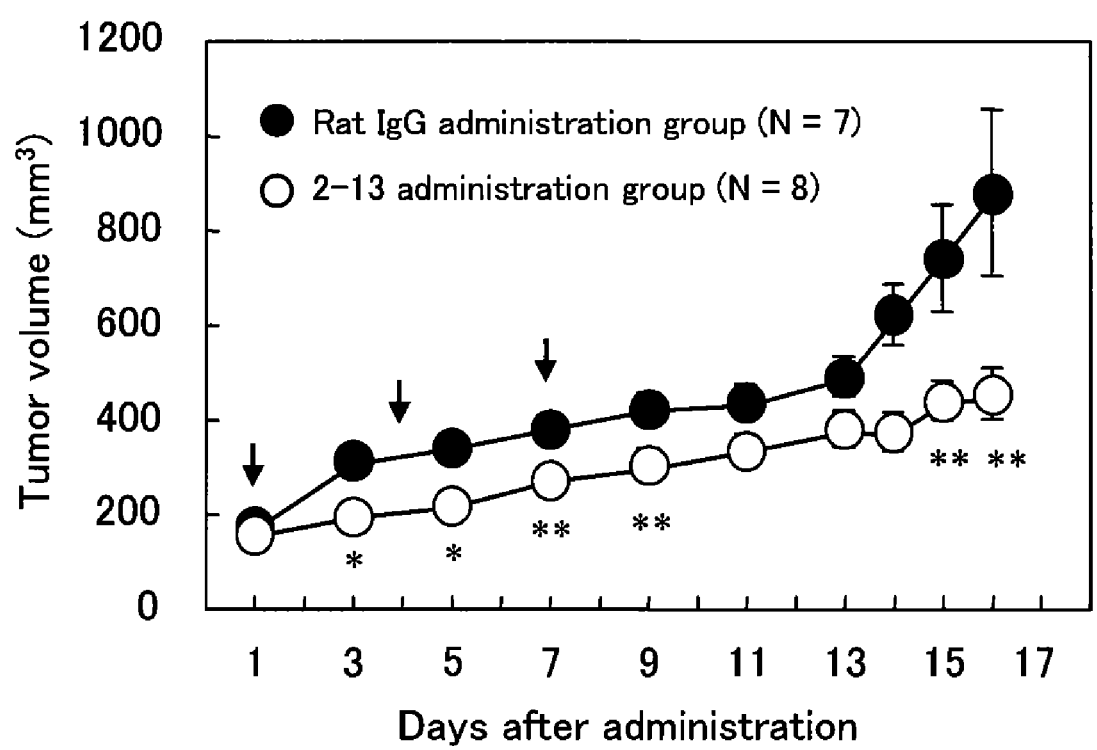

FIG. 4 shows the anti-tumor activity of an anti-hDlk-1 monoclonal antibody (clone 2-13) on Xenograft Treatment models using hDlk-1-expressing colon cancer cell line (SW480-hDlk cells). The SW480-hDlk cells were transplanted subcutaneously in nude mice to establish colon cancer tissues. The arrow indicates an intraperitoneal administration of antibody (20 mg/kg body weight) to the mice. The tumor volume was indicated by a mean value±standard error (*$P<0.01$, **$P<0.05$ by Student's-t-test).

Figure 5:
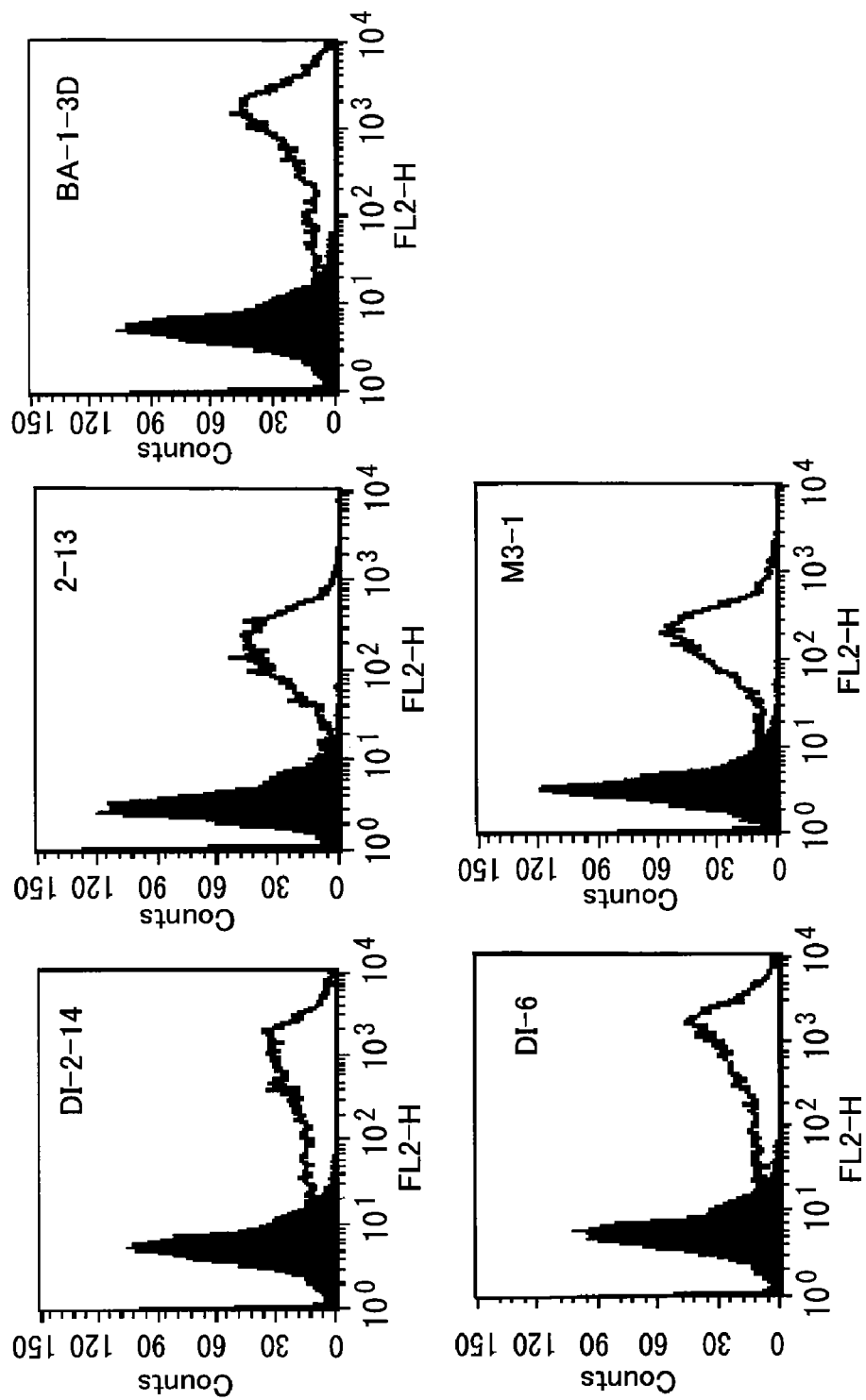

FIG. 5 shows the reactivity of anti-hDlk-1 monoclonal antibodies with HEK293-hDlk cells measured by flowcytometry. The number described in each histogram indicates each clone number. The filled portions indicate the isotype control antibodies. The black-lined portions indicate anti-hDlk-1 monoclonal antibodies.

Figure 6:
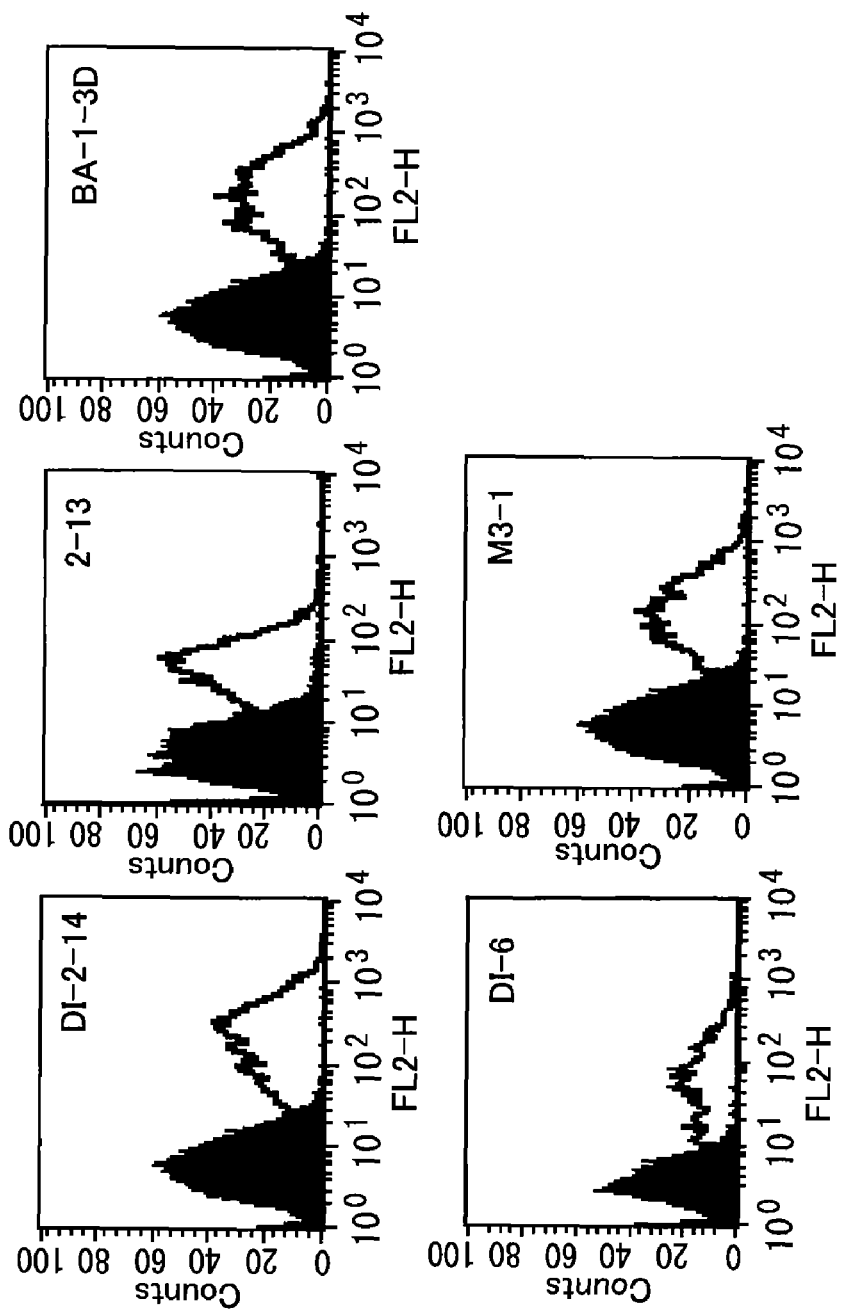

FIG. 6 shows the reactivity of anti-hDlk-1 monoclonal antibodies with Huh-7-hDlk cells measured by flowcytometry. The number described in each histogram indicates each clone number. The filled portions indicate the isotype control antibodies. The black-lined portions indicate anti-hDlk-1 monoclonal antibodies.

Figure 7:
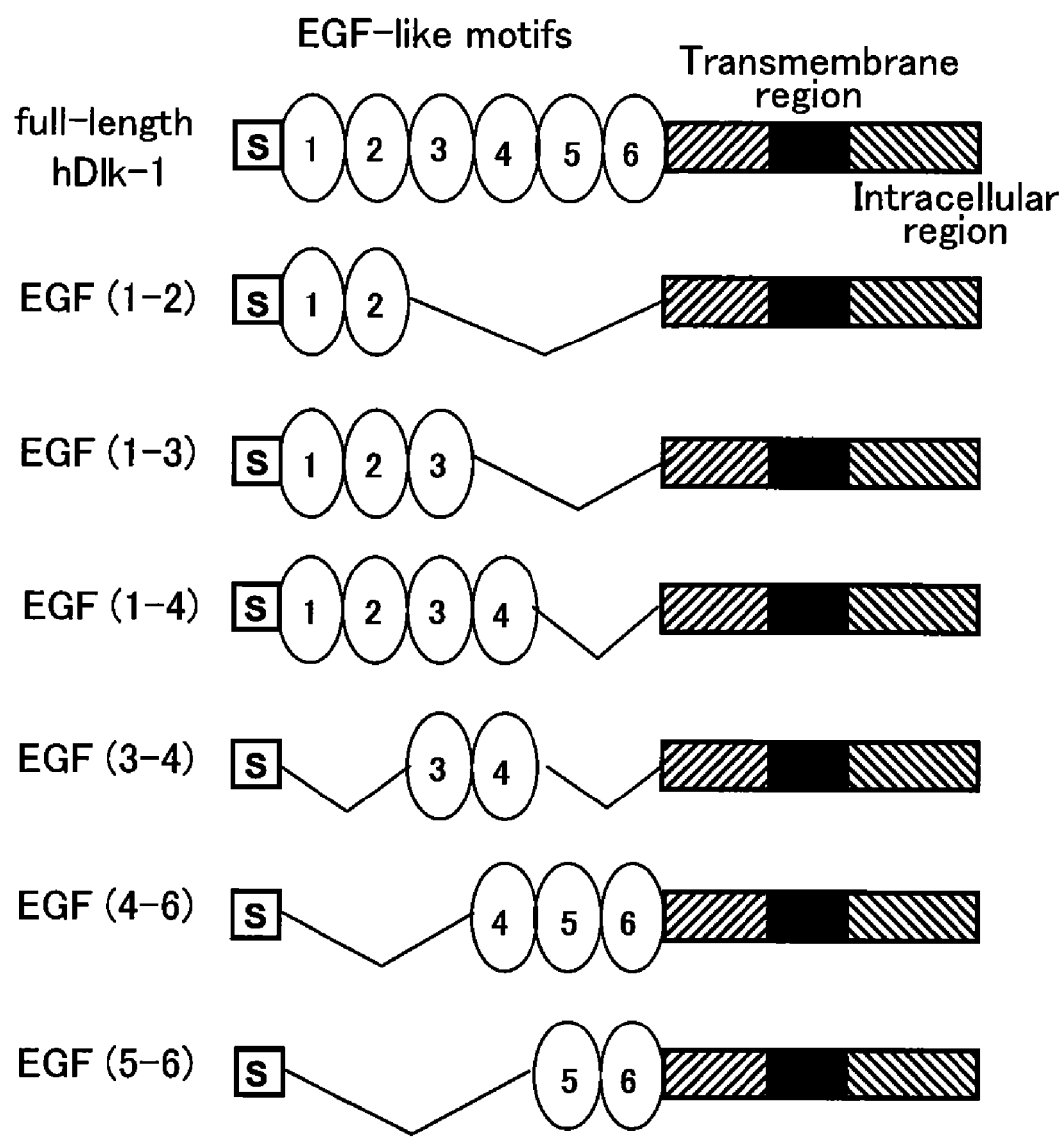

FIG. 7 is a schematic view showing mutants in which each EGF-like motif was deleted, which were produced in order to analyze epitopes recognized by anti-hDlk-1 monoclonal antibodies.

Figure 8:
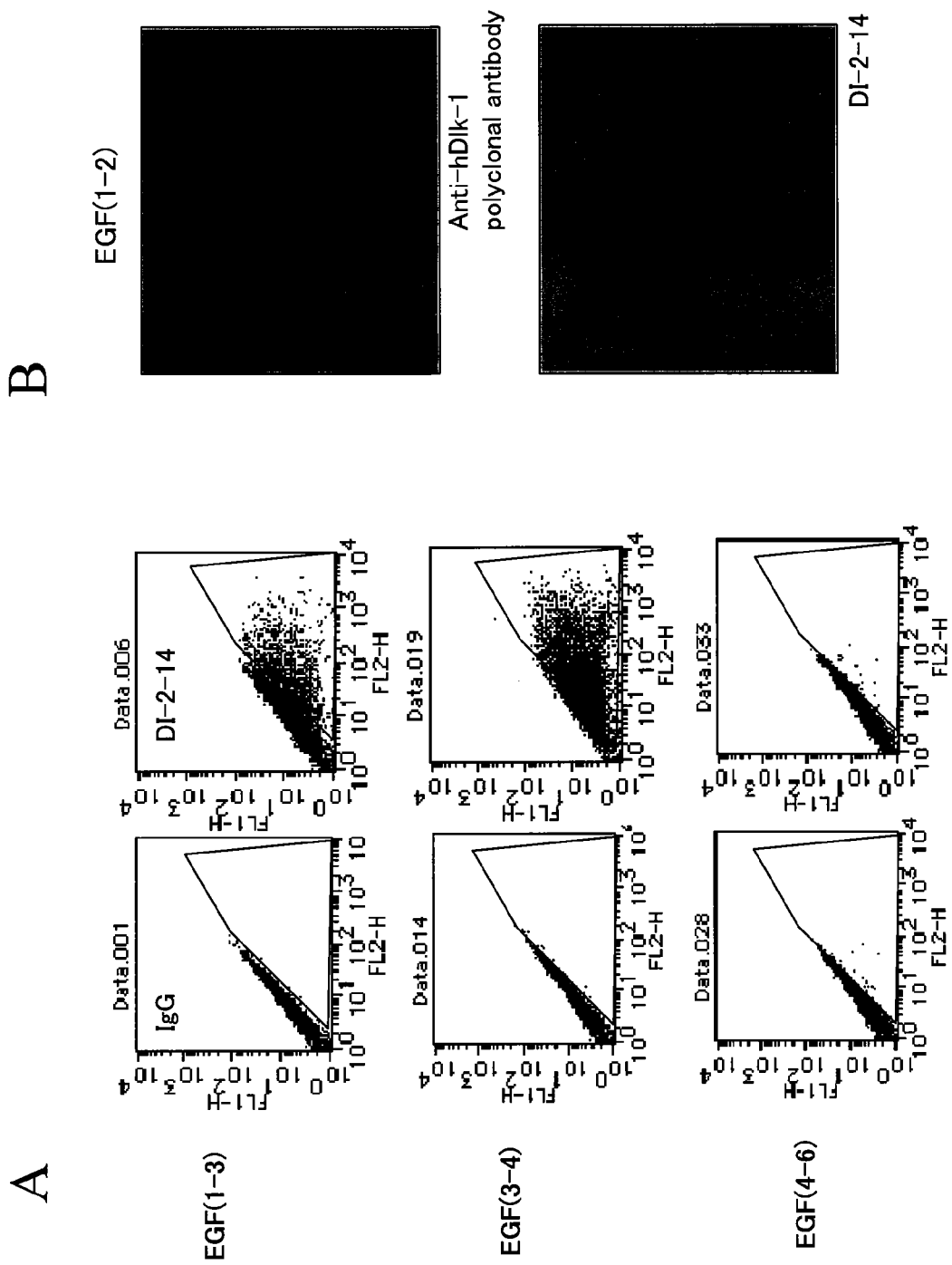

FIG. 8 shows the results of the epitope analysis of clone DI-2-14.

FIG. 8A: A figure showing the results obtained by transiently transfecting each described hDlk-1 gene mutant into COS-7 cells by lipofection and then performing FACS analysis on the cells 24 to 72 hours after the gene transfection (left: mouse IgG1, right: DI-2-14). The gated portions indicate each mutant-expressing cells recognized by the clone DI-2-14.

FIG. 8B: Photographs showing the smears of EGF (1-2)-expressing COS-7 cells, which were immunostained with a positive control (an anti-hDlk-1 polyclonal antibody) and the clone DI-2-14. Portions stained into brownish-red color indicate expression of the EGF (1-2).

Figure 9:
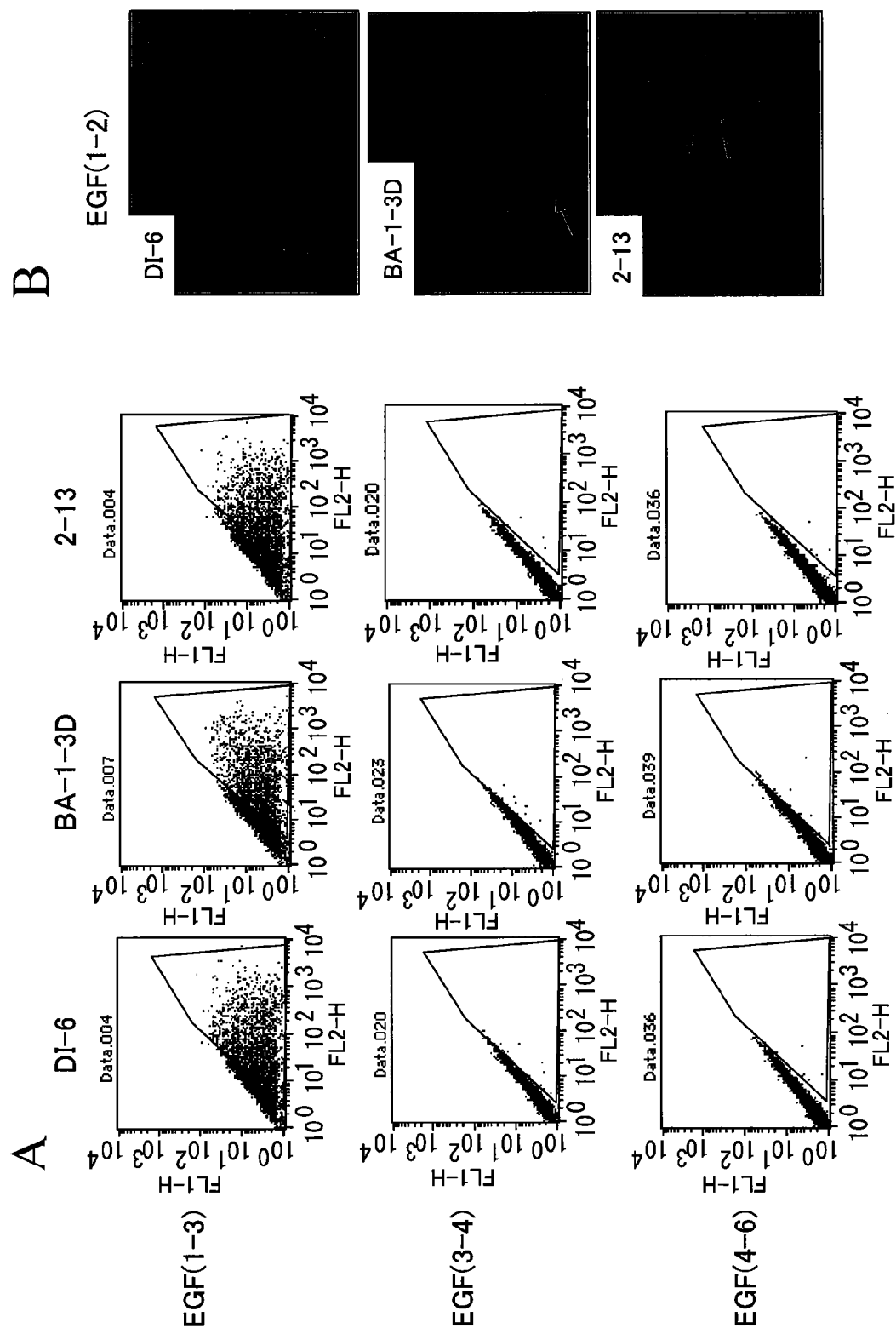

FIG. 9 shows the results of the epitope analyses of clones DI-6, BA-1-3D and 2-13.

FIG. 9A: A figure showing the results obtained by transiently transfecting each described hDlk-1 gene mutant into COS-7 cells by lipofection and then performing FACS analysis on the cells 24 to 72 hours after the gene transfection. The gated portions indicate each mutant-expressing cells recognized by each clone.

FIG. 9B: Photographs showing the smears of EGF (1-2)-expressing COS-7 cells, which were immunostained with clones DI-6, BA-1-3D and 2-13. Portions stained into brownish-red color, which are indicated by the arrows, shows expression of the EGF (1-2).

Figure 10:
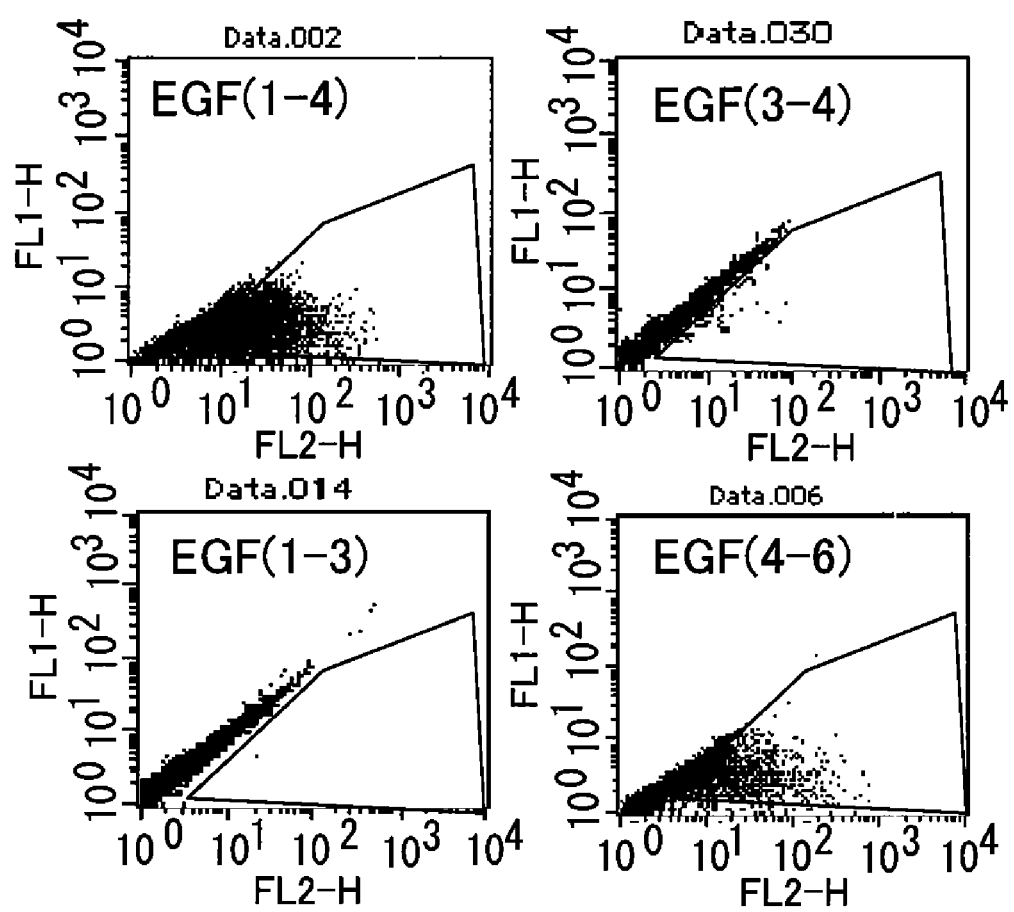

FIG. 10 shows the results of the epitope analysis of clone M3-1 by FACS.

The results obtained by transiently transfecting each described hDlk-1 gene mutant into COS-7 cells by lipofection and then performing FACS analysis on the cells 24 to 72 hours after the gene transfection. The gated portions indicate each mutant-expressing cells recognized by DI-2-14.

Figure 11:
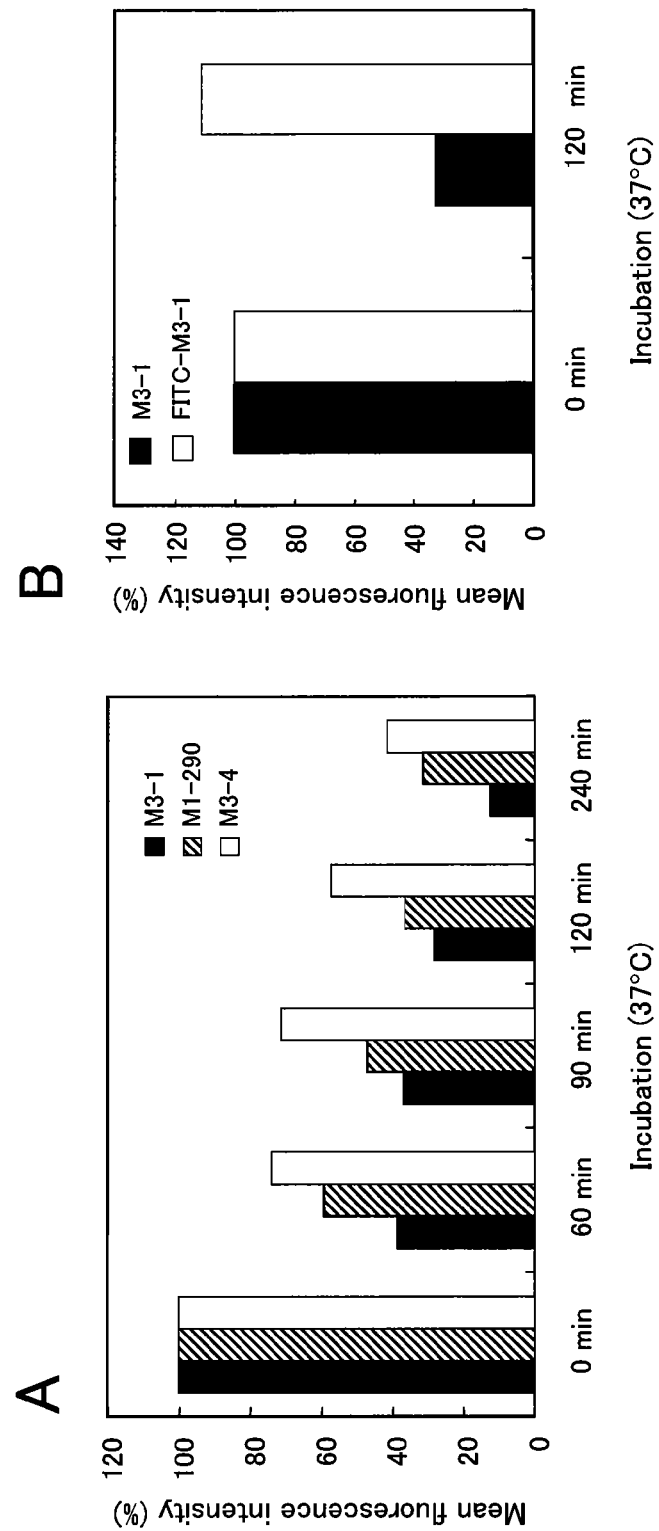

FIG. 11 shows the analytical results of the internalization activity of each anti-hDlk-1 monoclonal antibody after it bound to an antigen.

FIG. 11A: HEK293-hDlk cells were allowed to react with each anti-hDlk-1 monoclonal antibody (clones M3-1, M1-290 and M3-4) (4° C., 20 minutes) and the resultant cells were then washed with PBS 2 times. Thereafter, the cells were incubated at 37° C. for the period of time as described in the figure. Thereafter, the cells were allowed to react with PE-labeled anti-mouse IgG, followed by FACS analysis. The results are indicated with relative values, which are obtained when the mean fluorescence intensity in the case of no incubation (0 minute) is defined as 100%.

FIG. 11B: FITC-labeled clone M3-1 (FITC-M3-1) was allowed to react with HEK293-hDlk cells (4° C., 20 minutes) and the resultant cells were then washed with PBS 2 times. Thereafter, the cells were incubated at 37° C. for 120 minutes. FIG. 11B shows a change in the mean fluorescence intensity obtained as a result of the aforementioned incubation. The black column indicates a change in the mean fluorescence intensity obtained when unlabeled M3-1 was reacted with the cells in the same manner as in FIG. 11A above, the cells were then incubated at 37° C. for 120 minutes and they were then allowed to react with PE-labeled anti-mouse IgG.

Figure 12:
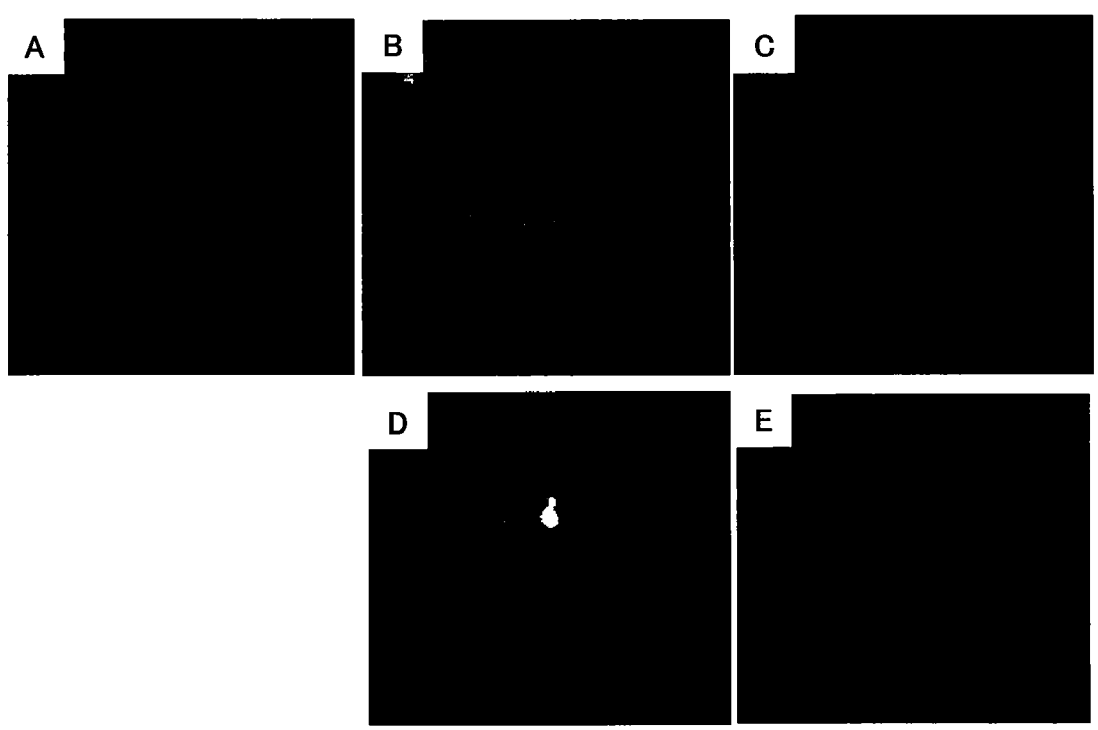

FIG. 12 shows the analytical results of the internalization activity of each rhodamine-labeled anti-hDlk-1 monoclonal antibody after it is bound to an antigen.

FIG. 12A: HEK293-hDlk cells were allowed to react with rhodamine-labeled M3-1 (Rho-M3-1) (4° C., 20 minutes) and the resultant cells were then washed with PBS 2 times. Immediately after the washing, a smear was prepared and localization of Rho-M3-1 was observed under a fluorescence microscope. FIG. 12A is a photograph showing such localization of Rho-M3-1. Orange colored portions indicate localization of Rho-M3-1. Localization of Rho-M3-1 into cell membrane was observed.

FIG. 12B to 12E: Rho-M3-1 (B), Rho-DI-1 (C) and Rho-M1-290 (D) and Rho-M3-4 (E) were allowed to react with HE 293-hDlk cells and the resultant cells were then washed with PBS 2 times, followed by incubation at 37° C. for 15 minutes. Thereafter, smears were produced and localization of each clone was observed under a fluorescence microscope. FIGS. 12B to 12E are photographs showing such localization of each clone. Both Rho-M3-1 and Rho-DI-1, which recognize the same epitopes (EGF 4-6), were incorporated into the cells and they were localized therein in the form of dots.

Figure 13:
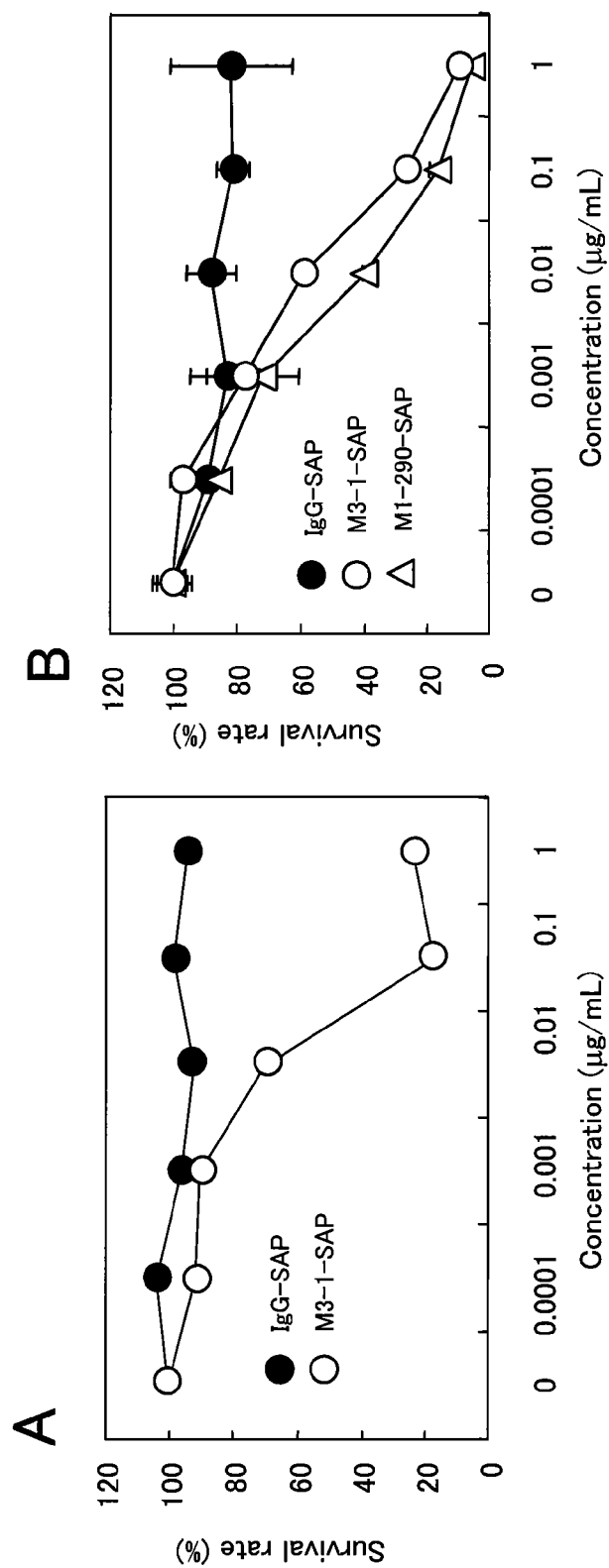

FIG. 13 shows the cytotoxic activity of saporin-conjugated anti-hDlk-1 monoclonal antibodies to Huh-7-hDlk cells and SK-N-F1 cells.

FIG. 13A: A figure showing the effects of a control (mouse IgG-saporin (IgG-SAP)) and M3-1-SAP on Huh-7-hDlk cells. The longitudinal axis indicates the survival rate of the cells, which is indicated by a relative value obtained when the survival rate of cells in the case of adding no antibodies is defined as 100% (N=3, a mean value±standard deviation).

FIG. 13B: A view showing the effects of a control (IgG-SAP), M3-1-SAP and M1-290-SAP on SK-N-F1 cells.

In FIG. 14, FIG. 14A shows a change in the body weight of each mouse and FIG. 14B shows the survival rate of mice, which were obtained when mouse IgG (20 mg/kg body weight), M3-1-SAP (5 mg/kg body weight) and M1-290-SAP (5 mg/kg body weight) were administered to the Xenograft models of Huh-7-hDlk cells. The value is indicated by a mean value±standard deviation. The arrows indicate the day in which the antibodies were administered.

Figure 15:
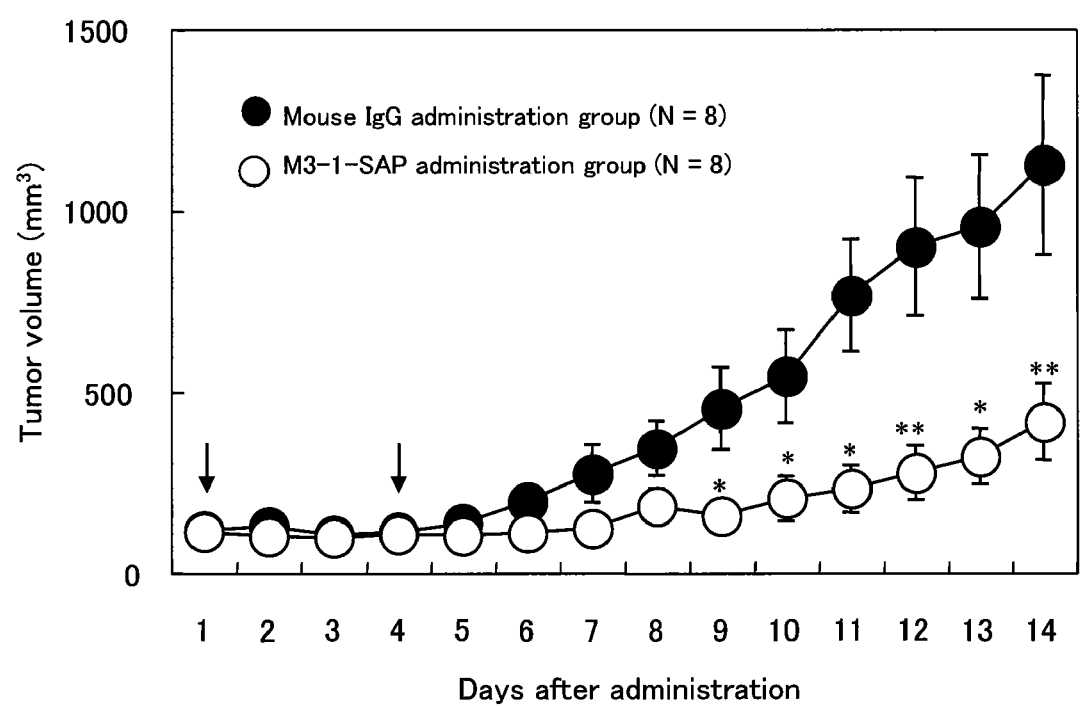

FIG. 15 shows the tumor growth-inhibiting effects of mouse IgG (●; N=8) and M3-1-SAP (○; N=8) obtained when these antibodies were intraperitoneally administered to the Xenograft models of Huh-7-hDlk cells. The arrows indicate the day in which the antibodies were administered. The value is indicated by a mean value±standard deviation (*P<0.01, **P<0.05 by Student's t-test).

Figure 16:
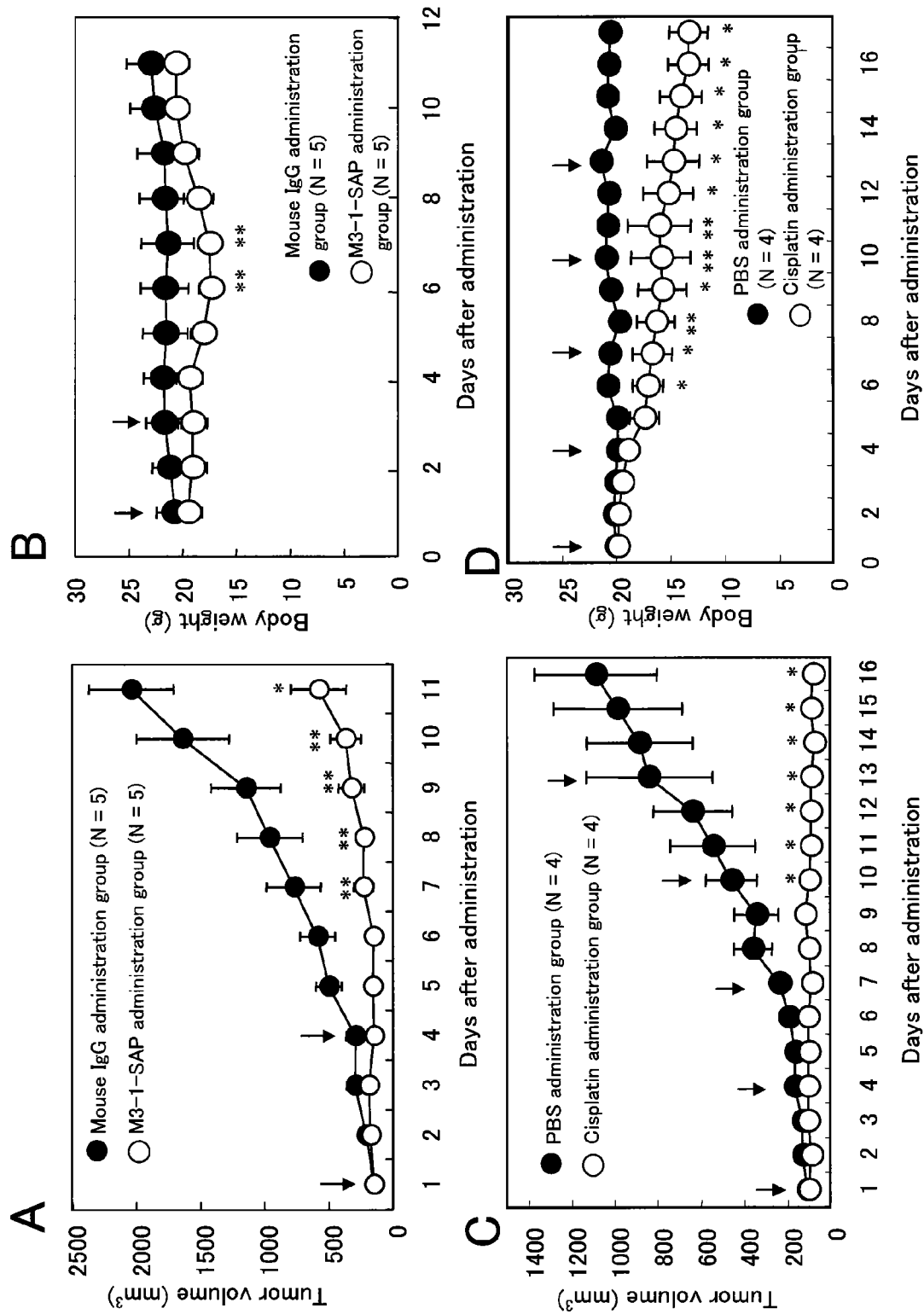

In FIG. 16, FIG. 16A shows a tumor growth-inhibiting effect and FIG. 16B shows a change in body weight, which were obtained when mouse IgG (●; N=5) and M3-1-SAP (○; N=5) were intratumorally administered (40 μg) to the Xenograft models of Huh-7-hDlk cells. FIG. 16C shows a tumor growth-inhibiting effect and FIG. 16D shows a change in body weight, which were obtained when PBS (●; N=4) and cisplatin (○; N=4) were intraperitoneally administered (5 mg/kg body weight) to the Xenograft models of Huh-7-hDlk cells. In all the figures, the arrows indicate the day in which the antibodies were administered and the value is indicated by a mean value±standard error (*P<0.01, **P<0.05 by Student's t-test).

Figure 17:
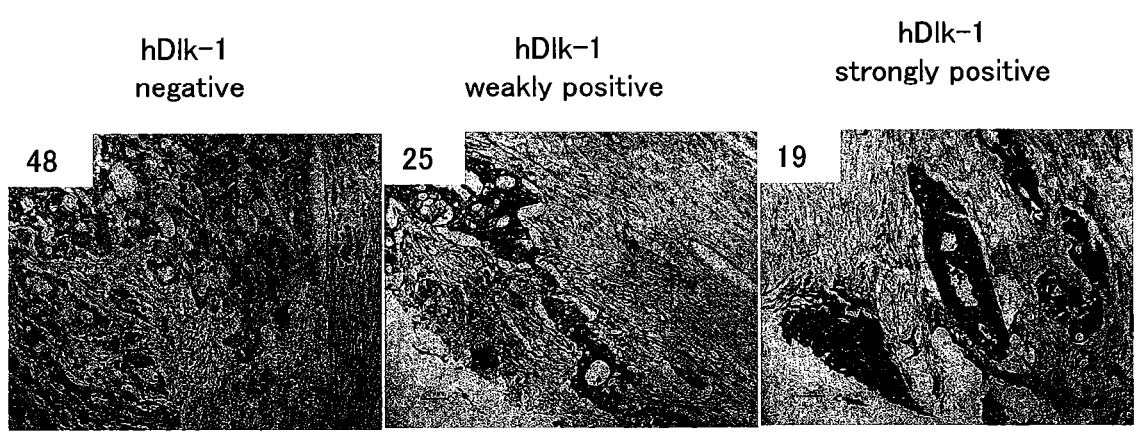

FIG. 17 includes photographs showing typical examples of a human colon cancer tissue array (manufactured by Cybrdi; CC05-01-001) immunostained with an anti-hDlk-1 antibody. The brownish-red portions indicate cancer tissues stained with the anti-hDlk-1 antibody. The term "hDlk-1 negative" means a section in which no stained regions were observed, as in the case of section No. 48 (69-year-old male, adenocarcinoma, Grade III). Section No. 19 (55-year-old female, adenocarcinoma, Grade II) was extremely strongly stained and sections stained at the same level as section No. 19 were defined as "hDlk-1 strongly positive." In addition, as in the case of section No. 25 (75-year-old male, adenocarcinoma, Grade II), a section that was clearly confirmed to be hDlk-1 positive and was slightly stained was defined as "hDlk-1 weakly positive."

Figure 18:
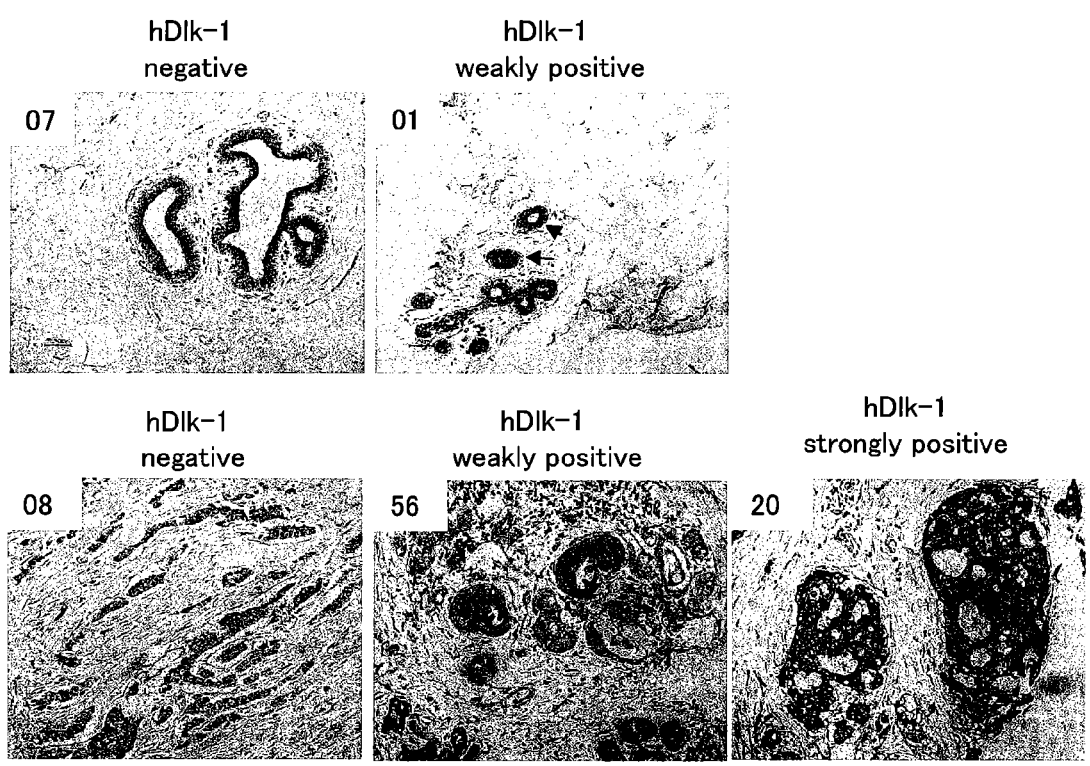

FIG. 18 includes photographs showing typical examples of a human breast cancer tissue array (manufactured by Cybrdi; CC08-02-002) immunostained with an anti-hDlk-1 antibody. The brownish-red portions indicate cancer tissues stained with the anti-hDlk-1 antibody.

The upper photographs show normal mammary gland tissues contained in the tissue array, which were stained with the anti-hDlk-1 antibody. Left: No. 07 (68-year-old female, normal mammary gland; hDlk-1 negative), right: No. 01 (43-year-old female, normal lobules of mammary gland; hDlk-1 weakly positive). The arrows indicate hDlk-1 weakly positive portions.

The lower photographs show the tissues of patients with infiltrating duct carcinoma. Left: No. 08 (45-year-old female, Grade II; hDlk-1 negative), center: No. 56 (28-year-old female, Grade II; hDlk-1 weakly positive), right: No. 20 (59-year-old female, Grade II; hDlk-1 strongly positive).

Figure 19:
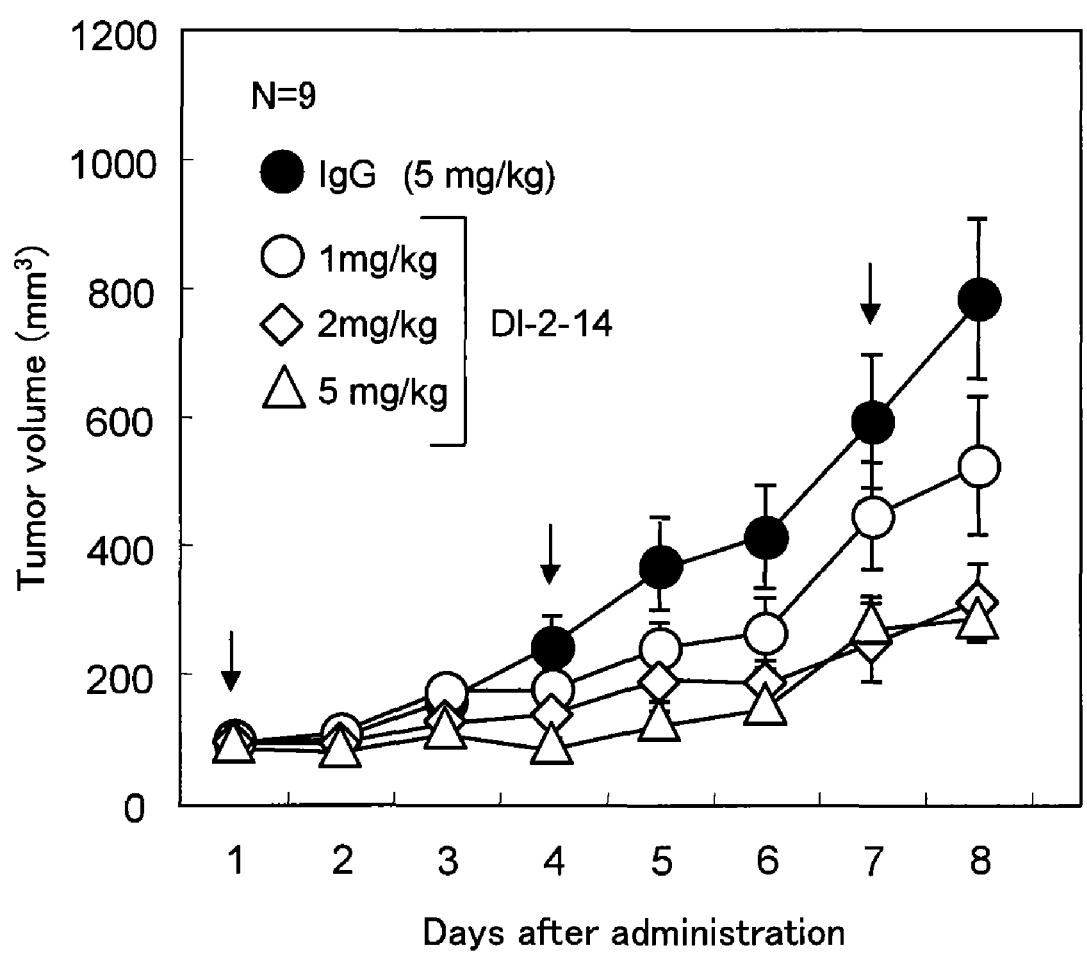

FIG. 19 shows the dose-dependent anti-tumor activity of clone DI-2-14 on Xenograft treatment models of Huh-7-dlk cells.

Figure 20:
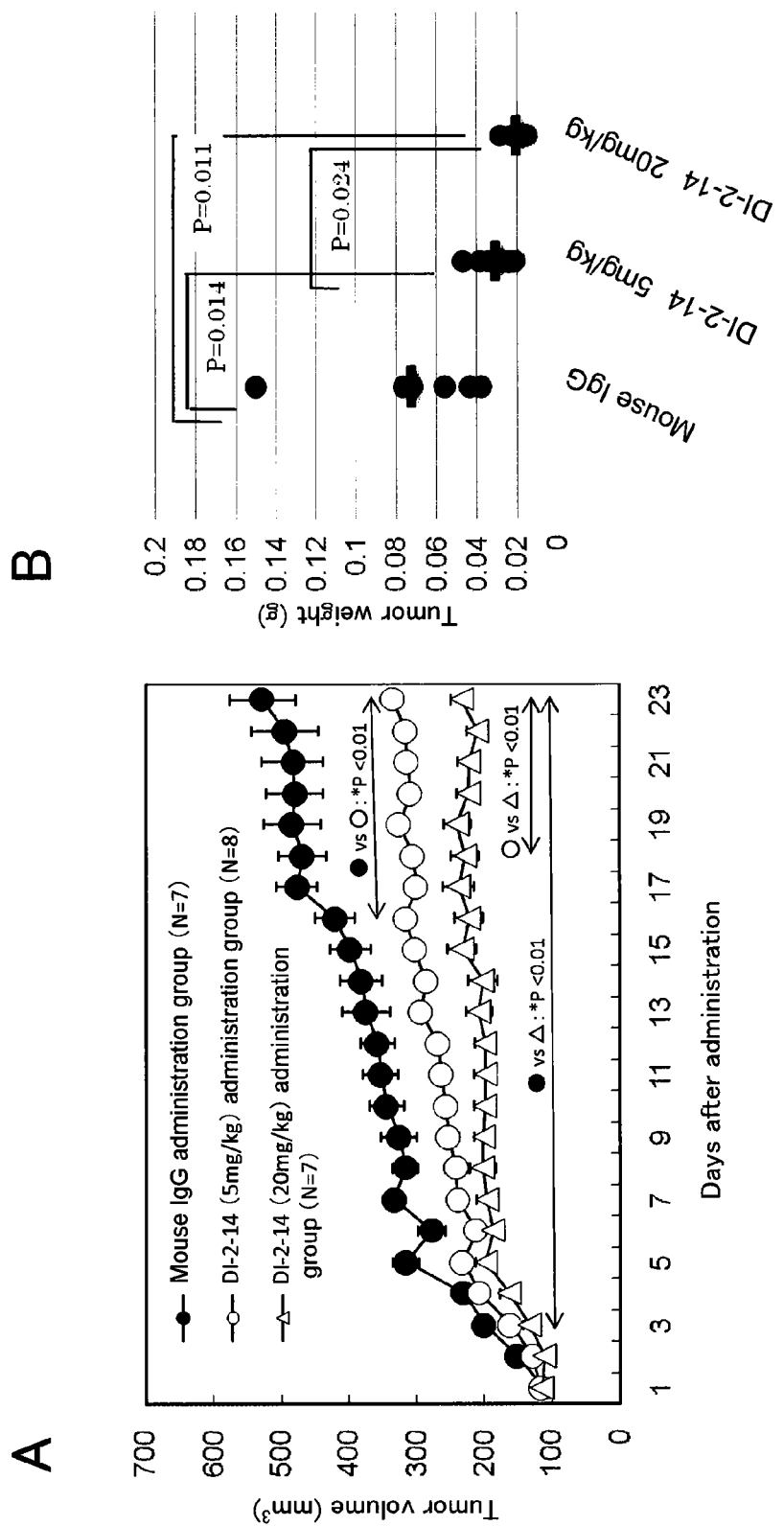

FIG. 20 shows the dose-dependent anti-tumor activity of clone DI-2-14 on Xenograft treatment models of SK-N-F1 cells.

FIG. 20A shows tumor growth after initiation of the administration of the antibodies. The tumor volume was indicated by a mean value±standard error (*P<0.01, **P<0.05 by Student's t-test).

FIG. 20B is a graph showing the weight of the excised cancer tissues on the 23$^{rd}$ day (Day 23) after the administration of the antibodies.

FIG. 21 shows the cDNA nucleotide sequence (SEQ ID NO: 22) of the H chain (heavy chain) variable region (VH) of clone DI-2-14 and a putative amino acid sequence thereof (SEQ ID NO: 23). Signal peptides are described in italics. The double-lined glutamic acid (E) represents the N-terminal amino acid residue of a mature peptide. The CDR sequences (underlined) were provided in accordance with the definition of Kabat et al. (Sequences of Proteins of Immunological Interests, Fifth edition, NIH Publication No. 91-3242, U.S. Department of Health and Human Services, 1991). The amino acid sequences of CDRs 1 to 3 of clone DI-2-14 VH are as shown in SEQ ID NOS: 30 to 32, respectively.

FIG. 22 shows the cDNA nucleotide sequence (SEQ ID NO: 24) of the L chain (light chain) variable region (VL) of clone DI-2-14 and a putative amino acid sequence thereof (SEQ ID NO: 25). Signal peptides are described in italics. The double-lined aspartic acid (D) represents the N-terminal amino acid residue of a mature peptide. The CDR sequences (underlined) were provided in accordance with the definition of Kabat et al. (1991; as described above). The amino acid sequences of CDRs 1 to 3 of clone DI-2-14 VL are as shown in SEQ ID NOS: 33 to 35, respectively.

FIG. 23 shows the nucleotide sequence (SEQ ID NO: 26) of a clone DI-2-14 VH gene and the amino acid sequence thereof (SEQ ID NO: 27). An SpeI site was added to the 5'-terminus and a HindIII site was added to the 3'-terminus (the two sites were underlined). The nucleotide sequence described in italics indicates a sequence corresponding to an intron.

FIG. 24 shows the nucleotide sequence (SEQ ID NO: 28) of a clone DI-2-14 VL gene and the amino acid sequence thereof (SEQ ID NO: 29). An NheI site was added to the 5'-terminus and an EcoRI site was added to the 3'-terminus (the two sites were underlined). The nucleotide sequence described in italics indicates a sequence corresponding to an intron.

Figure 25:
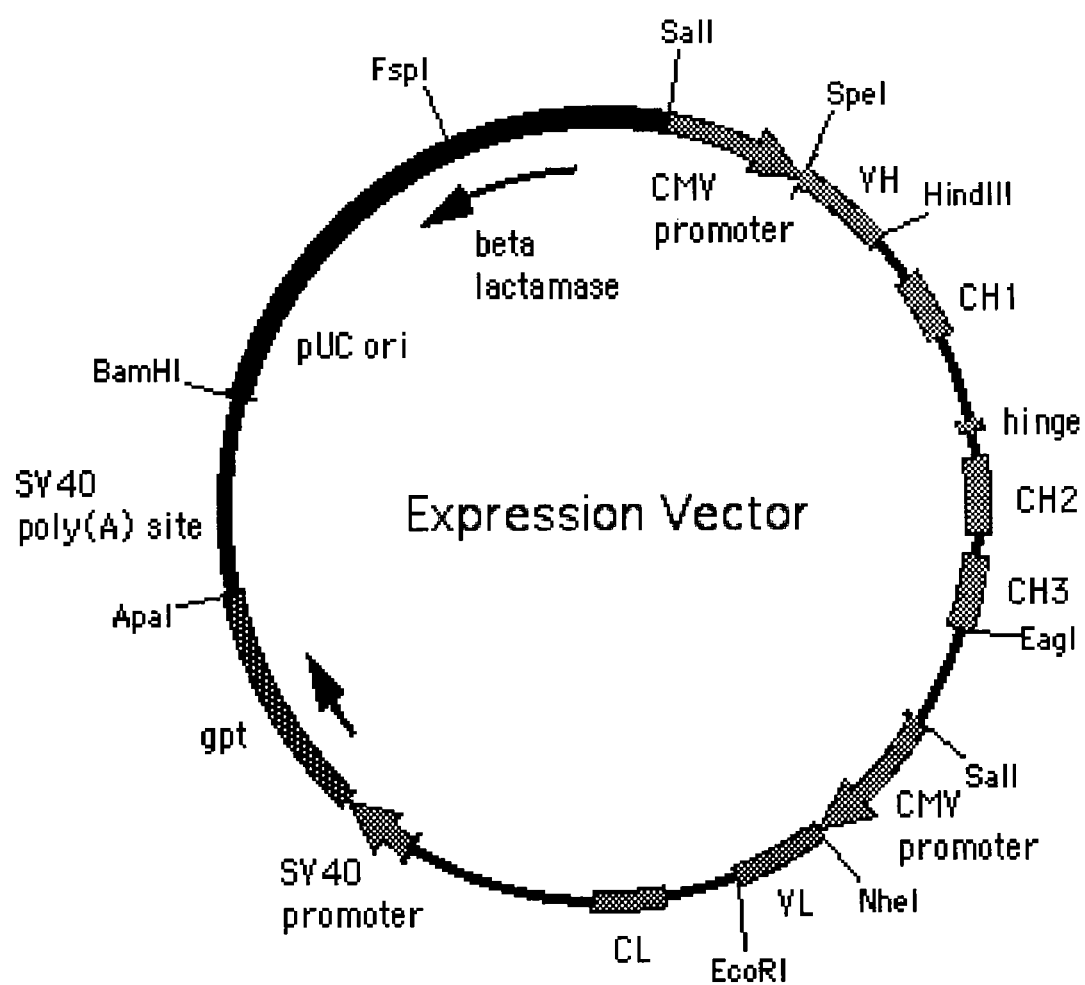

FIG. 25 is a schematic view of a chimeric DI-2-14 gene expression vector (pChDI-2-14). In a clockwise direction starting from the SalI site, this vector comprises a heavy chain translation unit starting with a human cytomegalovirus (CMV) major immediate early promoter and an enhancer used for initiation of the transcription of an antibody heavy chain gene. The CMV region then proceeds to a VH exon, the gene sequence of a human γ1 heavy chain constant region (which comprises the exons of CH1, a hinge region, CH2 and CH3, via introns) and after CH3, a poly A portion used for mRNA processing. After the heavy chain gene sequence, the vector comprises a light chain translation unit starting with a CMV promoter and an enhancer and it further comprises a VL exon, the exon (CL) of a human κ chain constant region having an intron portion upstream thereof and the poly A signal of a κ gene. Thereafter, the light chain gene proceeds to a segment comprising an SV40 early promoter, an *E. coli* xanthine guanine phosphoribosyl transferase (gpt) gene and the poly A portion of SV40. Finally, the plasmid has a part of a pUC19 plasmid comprising the replication origin of bacteria and a β-lactamase gene.

Figure 26:
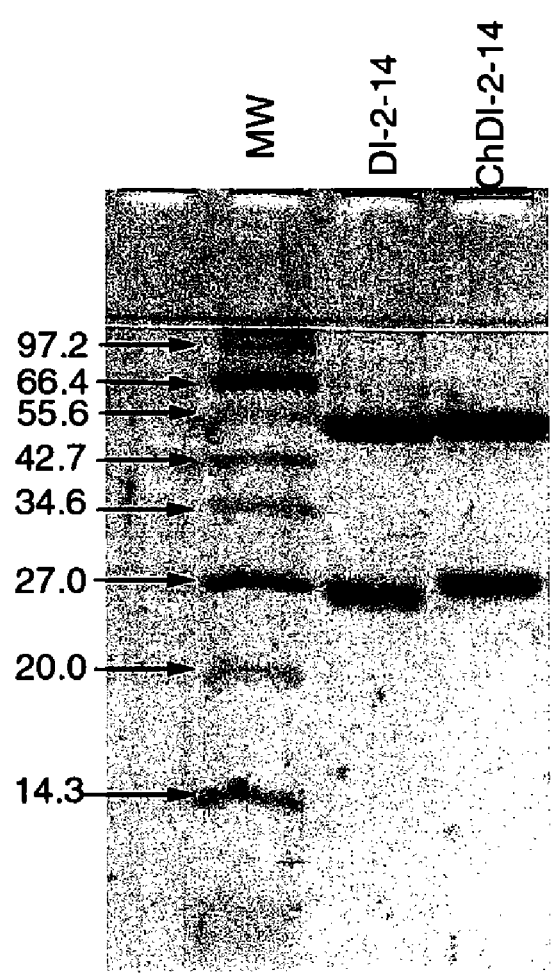

FIG. 26 shows mouse DI-2-14 and chimeric DI-2-14 (ChDI-2-14), which were developed by SDS-PAGE and were then stained with CBB. MW indicates a size marker and the arrows indicate the molecular weights of bands (kD).

Figure 27:
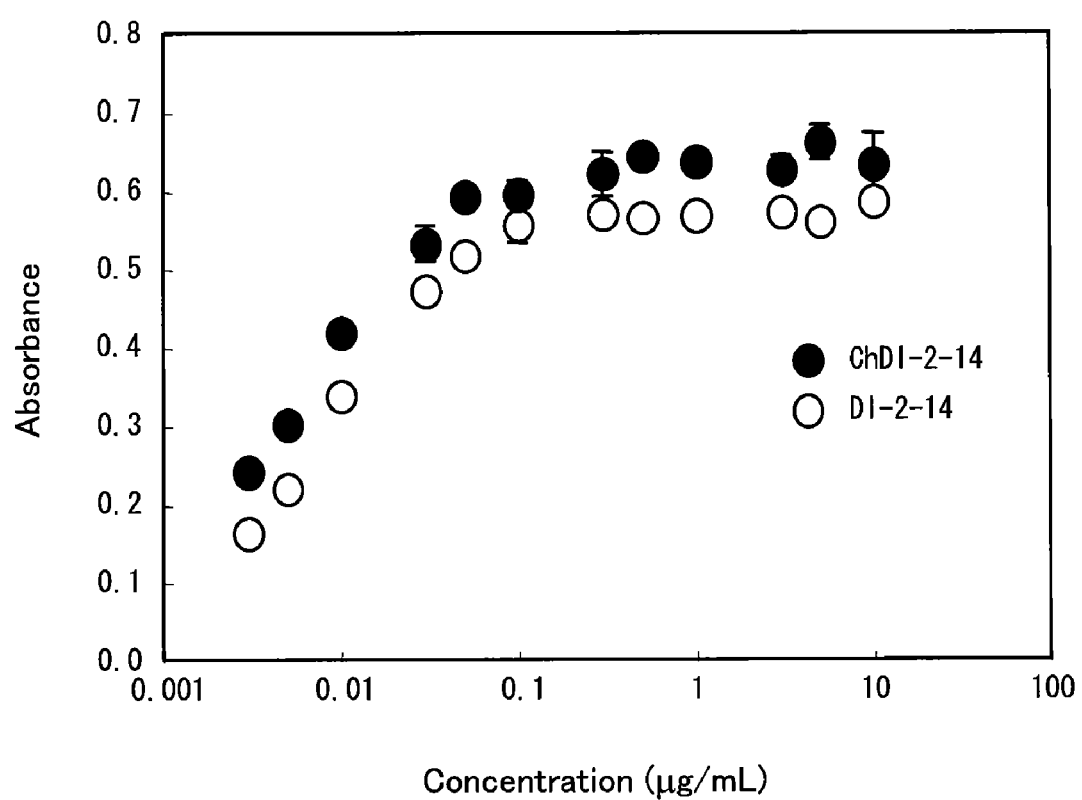

FIG. 27 shows the antigen-binding activity of DI-2-14 and ChDI-2-14 measured by purified FA-1 (hDlk-1 extracellular region) solid-phase ELISA. ○ indicates a mouse IgG1 antibody (clone DI-2-14) and ● indicates a chimeric antibody (ChDI-2-14).

Figure 28:
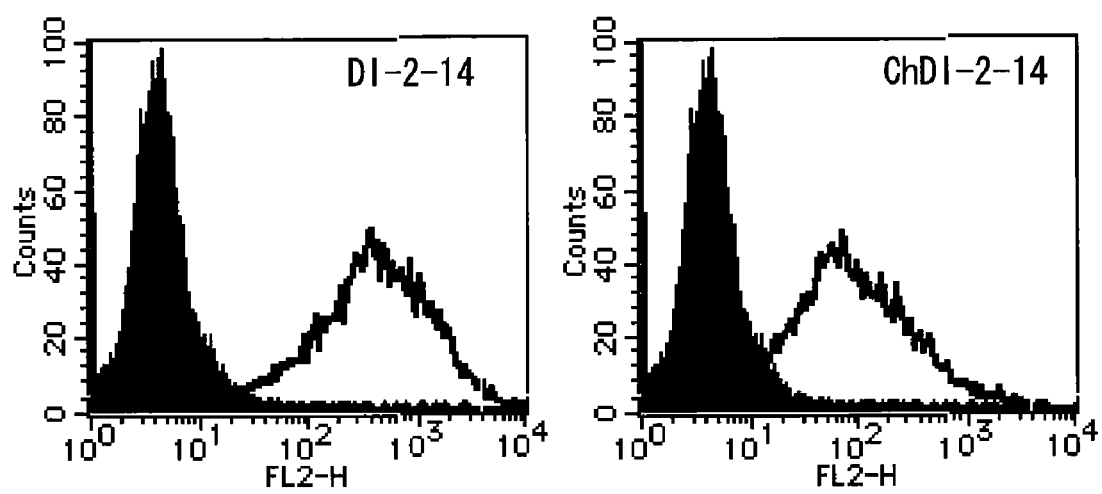

FIG. 28 shows the reactivity of DI-2-14 and ChDI-2-14 with HEK293-hDlk cells measured by flowcytometry. The filled histograms indicate isotype control antibodies and the black-lined (opened) histograms indicate DI-2-14 and ChDI-2-14.

Figure 29:
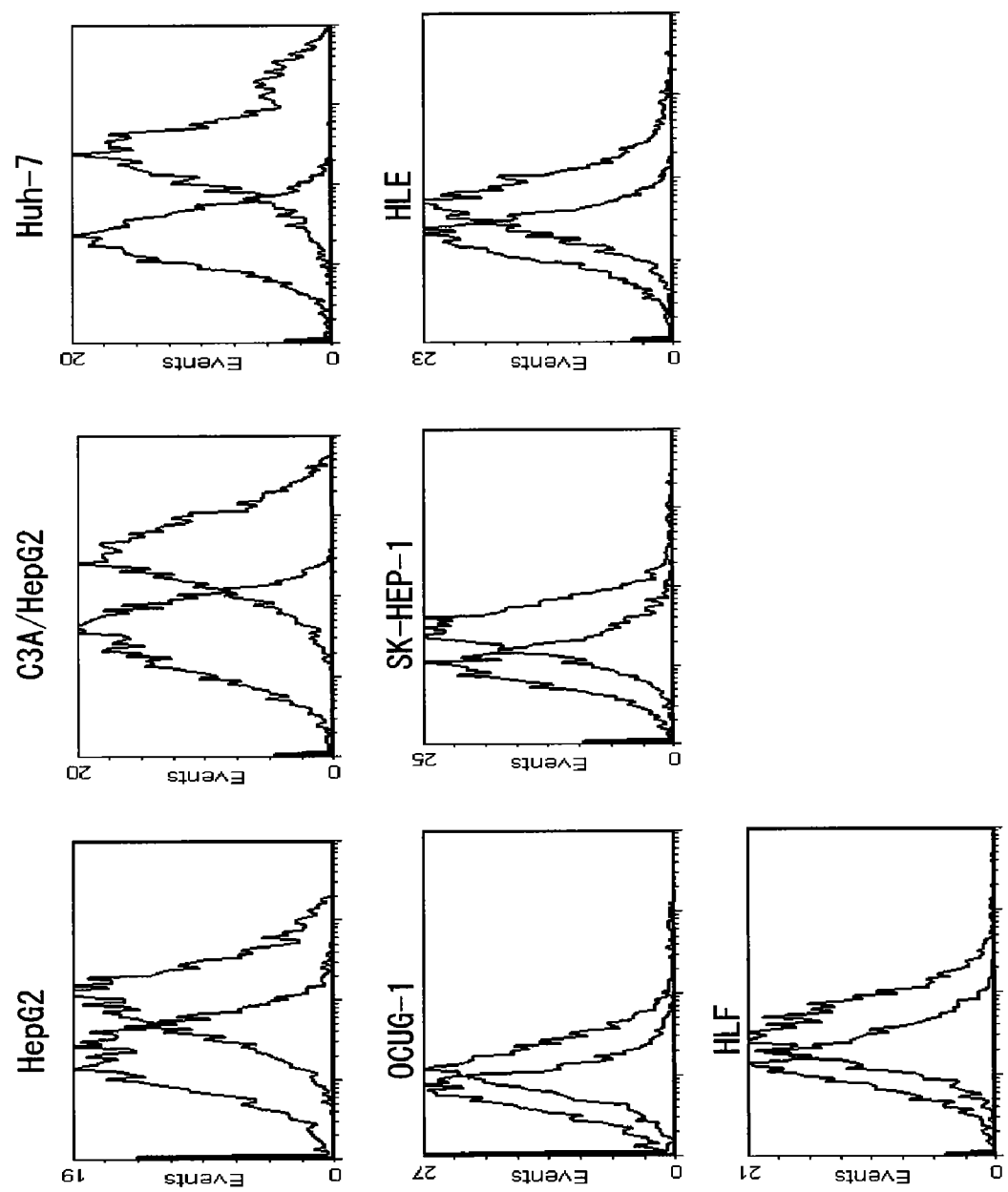

FIG. 29 shows the results obtained by analyzing expression of cell surface Dlk-1 in human liver cancer cell lines by flowcytometry. The blue line indicates mouse IgG1 and the red line indicates an anti-human Dlk-1 antibody. These are histograms obtained by staining each type of cells.

Figure 30:
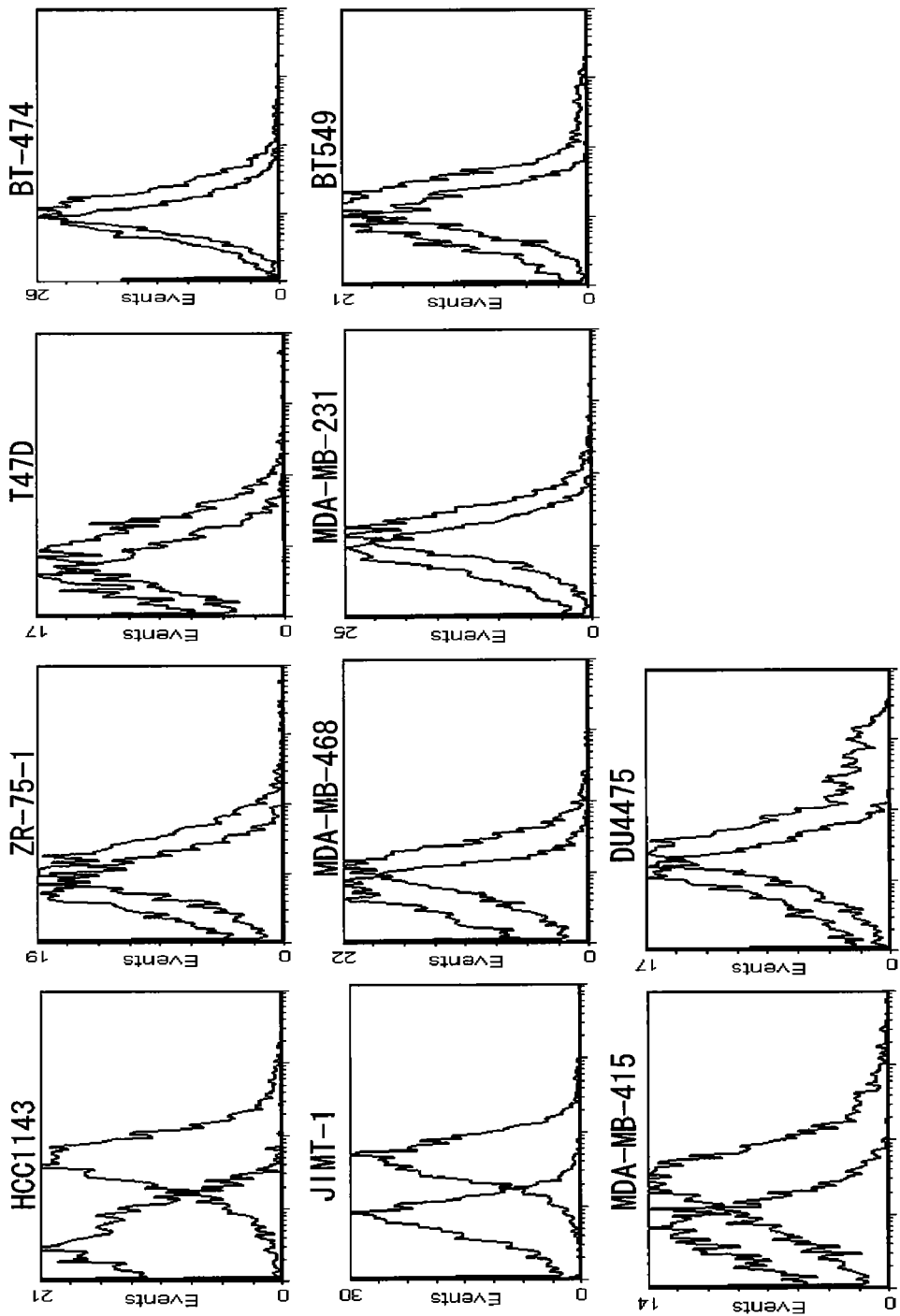

FIG. 30 shows the results obtained by analyzing expression of cell surface Dlk-1 in human breast cancer cell lines by flowcytometry. The blue line indicates mouse IgG1 and the red line indicates an anti-human Dlk-1 antibody. These are histograms obtained by staining each type of cells.

Figure 31:
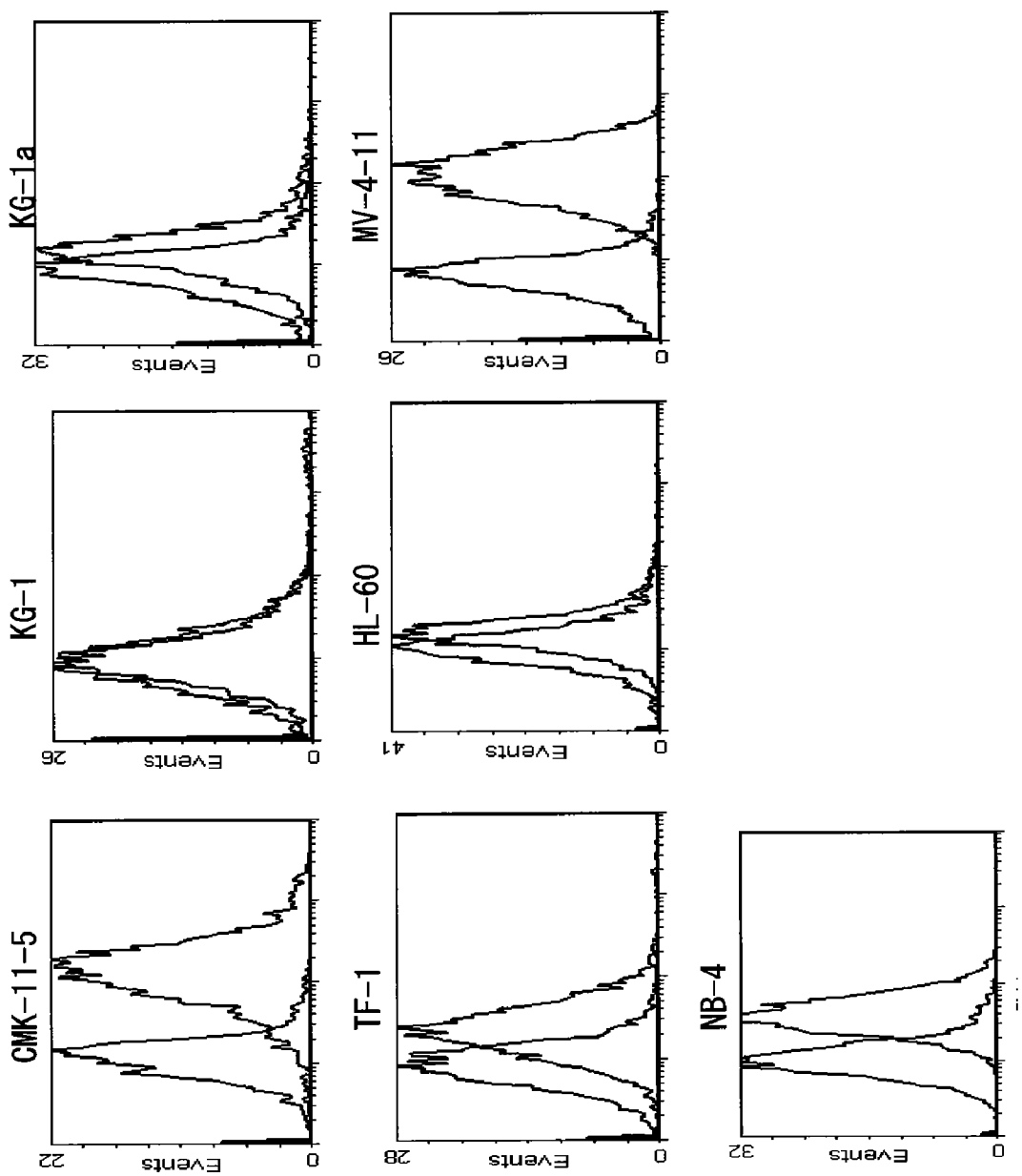

FIG. 31 shows the results obtained by analyzing expression of cell surface Dlk-1 in human leukemia cell lines by flowcytometry. The blue line indicates mouse IgG1 and the red line indicates an anti-human Dlk-1 antibody. These are histograms obtained by staining each type of cells.

Figure 32:
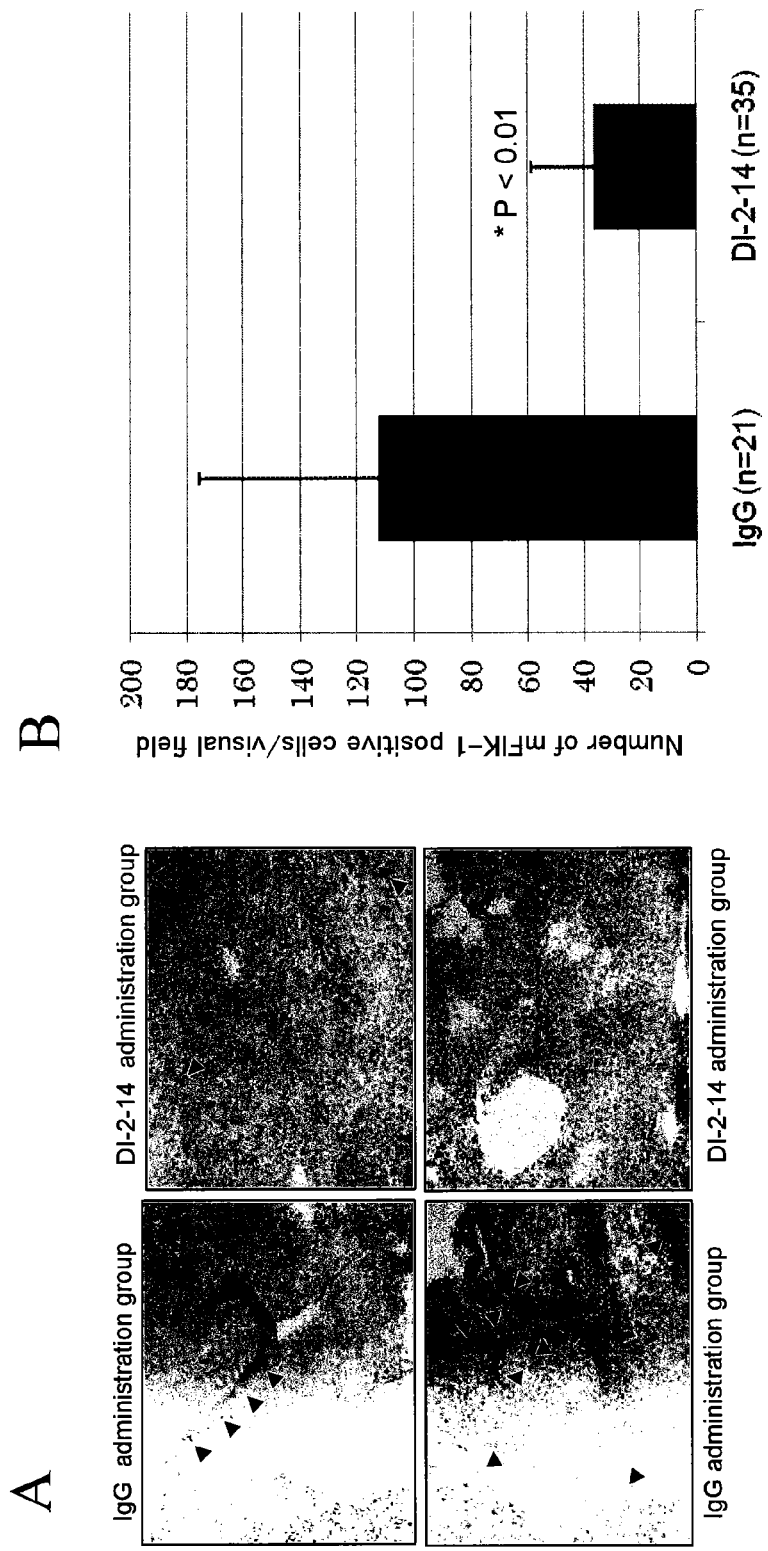

FIG. 32 shows the immunohistostaining of Flk-1/VEGF-R2 in cancer tissues excised from the Xenograft treatment models of Huh-7-dlk cells.

FIG. 32A includes photographs in which the fresh frozen sections of cancer tissues collected (excised) from a mouse IgG administration group (a control group) and a clone DI-2-14 administration group were immunostained with an anti-mouse Flk-1/VEGF-R2 antibody (objective 200-fold). In the photographs, portions indicated by the arrowhead (▲) indicates Flk-1/VEGF-R2 positive tumor vascular endothelial cells.

FIG. 32B is a graph, which was prepared by immunostaining the fresh frozen sections of cancer tissues collected (excised) from an IgG administration group (2 individuals) and a DI-2-14 administration group (4 individuals) with an anti-mouse Flk-1/VEGF-R2 antibody, then counting the number of Flk-1/VEGF-R2 positive tumor vascular endothelial cells in 8 to 13 visual fields (the IgG administration group: total 21 visual fields, the DI-2-14 administration group: total 35 visual fields) under an objective lens of 200-fold and then showing the number of cells per visual field (*$P<0.01$ by Student's t-test).

Figure 33:
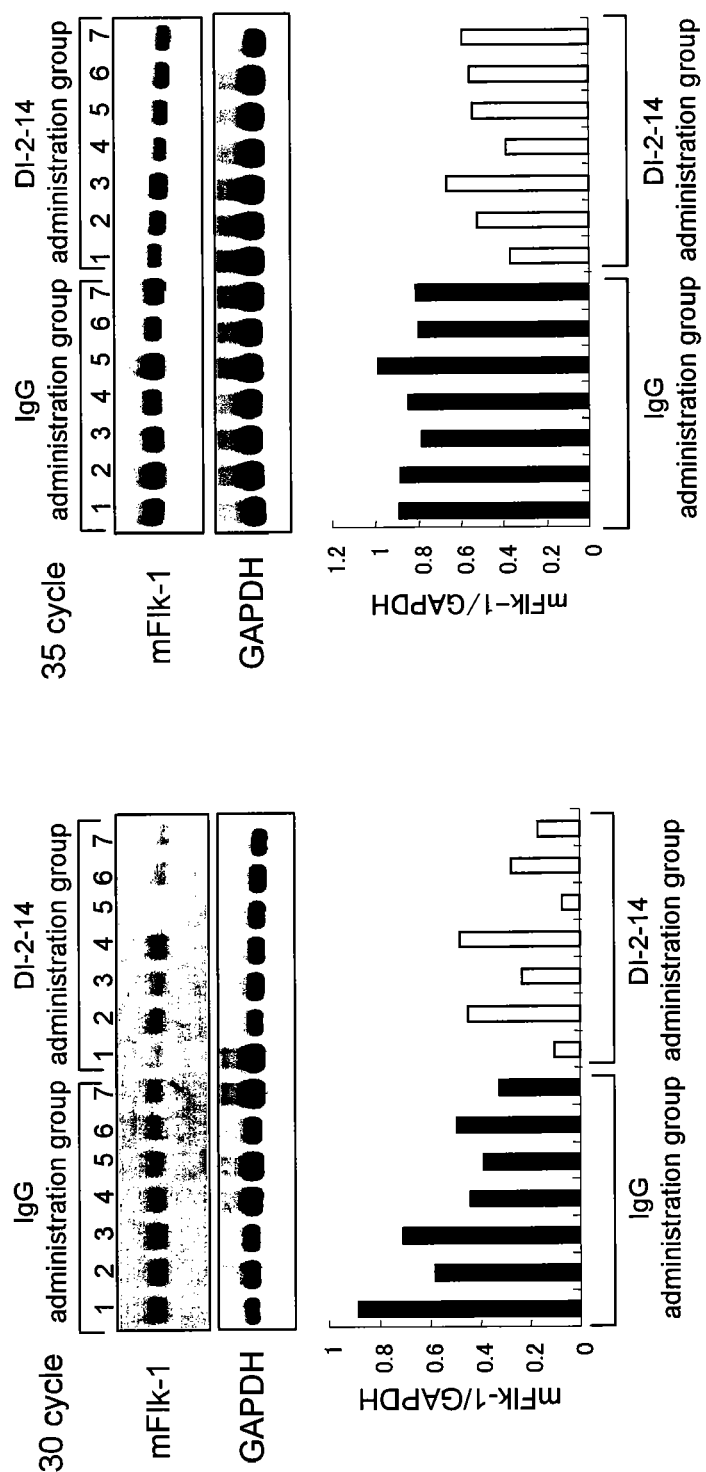

FIG. 33 shows gene expression of Flk-1/VEGF-R2 in cancer tissues excised from the Xenograft treatment models of Huh-7-dlk cells.

FIG. 33A shows an electrophoretic image, in which tumor was excised from each of an IgG administration group (N=7) and a DI-2-14 administration group (N=7), RNA was then extracted from the tumor using a Trizol reagent, $1^{st}$ strand cDNA was then synthesized and the gene expression of mouse Flk-1/VEGF-R2 (mFlk-1) and mouse/human GAPDH (GAPDH) was then confirmed by a PCR method (30 cycles) using each $1^{st}$ strand cDNA as a template. With regard to the lower graph, a band of the amplification product obtained by PCR performed on mFlk-1 and GAPDH was quantified by NIH image and it was then expressed in the form of a ratio (mFlk-1/GAPDH).

FIG. 33B is a figure obtained in the same manner as in FIG. 33A above, with the exception that the amplification reaction was carried out for 35 cycles by the PCR method.

BEST MODE FOR CARRYING OUT THE INVENTION

Hereinafter, the present invention will be described in detail. The following descriptions are not intended to limit the scope of the present invention. Other than the following examples, the present invention may be modified and may be carried out, as appropriate, within a range that does not impair the intention of the present invention.

The present specification includes all of the contents as disclosed in the specification of Japanese Patent Application No. 2006-305355, which is a priority document of the present application. Moreover, all publications cited in the present specification, which include prior art documents and patent documents such as laid-open application publications and patent publications, are incorporated herein by reference in their entirety.

1. Summary of the Present Invention

As described above, human Dlk-1 (delta-like 1 homolog (*Drosophila*); hDlk-1) is a type I transmembrane (one-transmembrane-type) protein with a full length of 383 amino acid residues and this protein has 6 EGF-like motifs in its extracellular region. It has been known that a hDlk-1 gene and a gene product thereof are expressed with a high frequency in various types of cancer or tumor cells. In general, it is difficult to prepare and obtain an antibody exhibiting anti-tumor activity in vivo. Thus, even if an anti-hDlk-1 monoclonal antibody is produced, it has anti-tumor activity in vitro but it does not exhibit the activity in vivo in many cases. Moreover, the functional domain of hDlk-1 that acts on the growth of cancer cells, a ligand (or a receptor) of hDlk-1, its intracellular signal-transducing pathway and the like have not been clarified. Thus, it is substantially impossible to efficiently produce an antibody by narrowing down its target. Under such circumstances, in the present invention, a clone having anti-tumor activity in vivo has been successfully obtained by screening it from a large number of clones.

First, based on immunohistochemistry using known anti-hDlk-1 antibodies, the present inventors have discovered that hDlk-1 is expressed in colon cancer and breast cancer, in addition to the aforementioned cancers and tumor cells, in which expression of hDlk-1 had previously been confirmed.

Next, the present inventors have newly produced approximately 100 clones of anti-hDlk-1 monoclonal antibodies for the purpose of producing anti-hDlk-1 antibodies capable of killing hDlk-1-expressing cancer cells at an individual level or inhibiting tumor growth, namely, anti-hDlk-1-antibodies having anti-tumor activity in vivo. Thereafter, the inventors have evaluated the in vivo pharmaceutical effects (anti-tumor action) of these clones, using tumor-bearing mice established by transplanting various types of cancer cell lines subcutaneously in nude mice. As a result, the present inventors have succeeded in obtaining several clones exhibiting significant tumor growth-inhibiting activity (clone name: DI-2-14, 2-13, BA-1-3D, DI-6 and M3-1).

Moreover, among the aforementioned anti-hDlk-1 antibodies, the present inventors have found an antibody excellent in terms of migratory ability to move into cells that express hDlk-1 (internalization activity) and the inventors have produced an antibody-agent complex, which comprises such an antibody and a compound having anti-tumor activity or cell-killing activity. This complex is what is called an "immunoconjugate," which is excellent in terms of ability to deliver agents into tumor cells as targets.

The present inventors have found that the aforementioned anti-hDlk-1 antibody or antibody-agent complex having anti-tumor activity is useful for the treatment of various types of tumors, or for the diagnosis and detection of tumors.

2. Preparation of Anti-hDlk-1 Antibody (1) Preparation of Antigen

Information regarding the amino acid sequence (SEQ ID NO: 2) of hDlk-1 is disclosed as "Accession number: NP_003827" at the website of NCBI (GenBank) (http://www.ncbi.nlm.nih.gov/), for example. Moreover, information regarding a nucleotide sequence (SEQ ID NO: 1) encoding the amino acid sequence of hDlk-1 is disclosed as "Accession number: NM_003836" at the same above website.

As an antigen, a polypeptide or peptide (which may be simply referred to as a "peptide" at times) comprising at least a portion of (entire or a part of) the amino acid sequence of hDlk-1 can be used and preferably, a peptide comprising at least a portion of (entire or a part of) the amino acid sequence of the extracellular region (FA-1) of hDlk-1 can be used. As stated above, the extracellular region of hDlk-1 comprises 6 EGF-like motifs (EGF-1 to EGF-6). This region indicates a region comprising amino acids at positions 26 to 244 in the amino acid sequence as shown in SEQ ID NO: 2 and preferably a region consisting of amino acids from "position 24" to "positions 248 to 285" (approximately 225 to 262 amino acid residues) in the amino acid sequence as shown in SEQ ID NO: 2.

Herein, in the case of a peptide used as an antigen, the length of the aforementioned "at least a portion of the amino acid sequence" is not particularly limited. For example, a region comprising one or two or more out of the 6 EGF-like motifs is preferable. More preferable examples include a region comprising EGF-1 and EGF-2 (namely, a region consisting of amino acids at positions 26 to 85 in the amino acid sequence as shown in SEQ ID NO: 2), a region comprising EGF-3 and EGF-4 (namely, a region consisting of amino acids at positions 92 to 167 in the amino acid sequence as shown in SEQ ID NO: 2) and a region comprising EGF-4, EGF-5 and EGF-6 (namely, a region consisting of amino acids at positions 131 to 244 in the amino acid sequence as shown in SEQ ID NO: 2).

As a method for preparing a peptide used as an antigen, either a chemical synthesis, or a synthesis by a genetic engineering means using *Escherichia coli* or the like, may be applied. Methods well known to persons skilled in the art may be applied.

In the case of performing a chemical synthesis of peptide, such a peptide may be synthesized by well known methods for synthesizing peptides. As such a synthesis, either a solid-phase synthesis method or a liquid-phase synthesis method may be applied. Commercially available peptide synthesizing apparatuses (e.g. PSSM-8, etc.; manufactured by Shimadzu Corp.) may be used.

In the case of synthesizing a peptide by genetic engineering, DNA encoding the peptide is first designed and synthesized. The designing and synthesis of the DNA can be carried out, for example, by a PCR method, using a vector comprising a full-length hDlk-1 gene or the like as a template and also using primers designed such that a desired DNA region can be synthesized therewith. Thereafter, the thus synthesized DNA is ligated to a suitable vector to obtain a recombinant vector used in expression of a protein. This recombinant vector is then introduced into a host such that a gene of interest can be expressed therein, so as to obtain a transformant (Sambrook J. et al., Molecular Cloning, A Laboratory Manual, $3^{rd}$ edition, Cold Spring Harbor Laboratory Press, 2001).

As a vector, a phage or plasmid capable of autonomously replicating in host microorganisms can be used. Further, an animal virus or insect virus vector can also be used. For preparation of a recombinant vector, the purified DNA may be cleaved with suitable restriction enzymes, the obtained DNA portion may be then inserted into the restriction site of suitable vector DNA, etc. and it may be then ligated to a vector. The type of a host used in transformation is not particularly limited, as long as it is able to express a gene of interest. Examples of such a host include bacteria (*Escherichia coli*, *Bacillus subtilis*, etc.), yeasts, animal cells (COS cells, CHO cells, etc.), insect cells and insects. It is also possible to use a mammal such as a goat as a host. A method for introducing a recombinant vector into a host is known.

The aforementioned transformant is cultured and a peptide used as an antigen is then collected from the culture. The term "culture" is used to mean any one of (a) a culture supernatant and (b) cultured cells, a cultured cell mass, or a disintegrated product thereof.

After completion of the culture, when a peptide of interest is produced in a bacterial cells (bacterial bodies) or in cells, such bacterial cells or cells are disintegrated and a peptide is then extracted. On the other hand, a peptide of interest is produced outside the bacterial cell or cells, a culture solution is directly used, or the bacterial cells or cells are eliminated by centrifugation or the like. Thereafter, common biochemical methods used in isolation and purification of peptides, such as ammonium sulfate precipitation, gel filtration, ion exchange chromatography and affinity chromatography, are applied singly or in combination, so as to isolate and purify a peptide of interest.

In the present invention, a peptide used as an antigen can also be obtained by in vitro translation using a cell-free synthesis system. In this case, two types of methods, namely, a method using RNA as a template and a method using DNA as a template (transcription/translation) can be applied. As such a cell-free synthesis system, commercially available systems such as EXPRESSWAY™ system (Invitrogen), PURESYSTEM (registered trade mark; Post Genome Institute Co., Ltd.) and TNT system (registered trade mark; Promega) can be used.

The thus obtained peptide may also be bound to a suitable carrier protein such as bovine serum albumin (BSA), keyhole limpet hemocyanin (KLH), human thyroglobulin, or chicken gamma globulin.

Furthermore, such an antigen may be a peptide, which consists of an amino acid sequence comprising a deletion, substitution or addition of one or multiple amino acids with respect to the amino acid sequence of hDlk-1 (SEQ ID NO: 2) or the aforementioned partial sequence thereof. For example, there can also be used a peptide, which consists of an amino acid sequence comprising a deletion of one or multiple (preferably one or several (for example 1 to 10 and more preferably 1 to 5)) amino acids, a substitution of one or multiple (preferably one or several (for example 1 to 10 and more preferably 1 to 5)) amino acids with other amino acids, or an addition of one or multiple (preferably one or several (for example 1 to 10 and more preferably 1 to 5)) amino acids, with respect to the amino acid sequence of hDlk-1 or a partial sequence thereof.

In the present invention, an example of a gene to be introduced into cells or the like is a gene encoding a hDlk-1 protein, a partial fragment thereof, a mutant protein thereof, or a fragment thereof. As such a gene, a gene having the nucleotide sequence as shown in SEQ ID NO: 1 or a partial sequence thereof can be used, for example.

Further, as such a gene to be introduced into cells or the like, a nucleotide sequence, which hybridizes with a sequence complementary to the nucleotide sequence as shown in SEQ ID NO: 1 under stringent conditions and encodes a protein having hDlk-1 activity, or a partial sequence thereof can also be used.

The term "stringent conditions" is used to mean conditions applied to washing after hybridization, which consist of a salt (sodium) concentration of buffer between 10 and 500 mM and a temperature between 42° C. and 72° C. and preferably consist of the aforementioned salt concentration of buffer between 50 and 300 mM and a temperature between 55° C. and 68° C.

Mutation can be introduced into a gene by known methods such as a Kunkel method or a Gapped duplex method, using mutation introduction kits that utilize site-directed mutagenesis, such as GENETAILOR™ Site-Directed Mutagenesis System (manufactured by Invitrogen) or TaKaRa Site-Directed Mutagenesis System (Mutan-K, Mutan-Super Express Km, etc.; manufactured by Takara Bio Inc.).

(2) Preparation of Polyclonal Antibody

The prepared antigen is administered to a mammal for immunization. The type of such a mammal is not particularly limited. Examples of such a mammal include a rat, a mouse and a rabbit. Among others, a mouse is preferable.

The dose of the antigen per animal can be determined, as appropriate, depending on the presence or absence of an adjuvant. Examples of such an adjuvant include a Freund's complete adjuvant (FCA), a Freund's incomplete adjuvant (FIA) and an aluminum hydroxide adjuvant. Immunization can be carried out by injecting the antigen into the vein, footpad, subcutis, abdominal cavity, etc. In addition, immunization interval is not particularly limited. Immunization is carried out 1 to 10 times and preferably 2 or 3 times, at intervals of several days to several weeks and preferably at intervals of 1 week. Three to seven days after the final immunization, an antibody titer is measured by enzyme immunoassay (ELISA or EIA), radioimmunoassay (RIA), etc. On the day at which a desired antibody titer is obtained, blood is collected and antiserum is then obtained. In a case where an antibody should be purified in the aforementioned method for collecting the antibody, a suitable method is appropriately selected from known methods such as an ammonium sulfate salting-out method, ion exchange chromatography, gel filtration chromatography and affinity chromatography, or these methods may be used in combination, so as to purify the antibody. Thereafter, the reactivity of a polyclonal antibody contained in the antiserum is measured by ELISA, etc.

(3) Preparation of Monoclonal Antibody (3-1) Collection of Antibody-Producing Cells The type of the anti-hDlk-1 antibody of the present invention is not limited. A monoclonal antibody is preferable.

The prepared antigen is administered to a mammal such as a rat, a mouse or a rabbit for immunization. The dose of the antigen per animal can be determined, as appropriate, depending on the presence or absence of an adjuvant. The same adjuvants as those described above are used herein. Also, the same immunization methods as described above are applied herein. One to sixty days and preferably one to fourteen days after the final immunization, antibody-producing cells are collected. Examples of such antibody-producing cells include splenic cells, lymph node cells and peripheral blood cells. Among others, lymph node cells and splenic cells are preferable.

(3-2) Cell Fusion

In order to obtain a hybridoma (an antibody-producing cell line), cell fusion is carried out between antibody-producing cells and myeloma cells. As myeloma cells to be fused with antibody-producing cells, easily available, established cell lines, such as the cell lines of animals such as mice, can be used. As available cell lines, those, which have drug selectivity, cannot survive in a HAT selective medium (containing hypoxanthine, aminopterin and thymidine) when they are in an unfused state and can survive therein only when they are fused with antibody-producing cells, are preferable.

Examples of myeloma cells used herein include mouse myeloma cell lines such as P3-X63-Ag8.653, P3-X63-Ag8 (X63), P3-X63-Ag8.U1(P3U1), P3/NS I/1-Ag4-1(NS1) and Sp2/0-Ag14(Sp2/0). Such myeloma cells can be selected, while taking into consideration the compatibility with antibody-producing cells, as appropriate.

Subsequently, myeloma cells are fused with antibody-producing cells for cell fusion. For such cell fusion, antibody-producing cells at a cell density of $1 \times 10^6$ to $1 \times 10^7$ cells/mL are mixed with myeloma cells at a cell density of $2 \times 10^5$ to $2 \times 10^6$ cells/mL, in a medium used for animal cells that does not contain serum, such as DMEM or a RPMI-1640 medium. The cell ratio between such antibody-producing cells and such myeloma cells (antibody-producing cells:myeloma cells) is not limited. In general, such a cell ratio is preferably between 1:1 and 10:1 and more preferably 3:1. Subsequently, a fusion reaction is carried out in the presence of a cell fusion promoter. As such a cell fusion promoter, polyethylene glycol having a mean molecular weight between 1,000 and 6,000 daltons (D) or the like can be used, for example. Also, antibody-producing cells can be fused with myeloma cells using a commercially available cell fusion device that utilizes electrical stimulation (e.g. electroporation).

(3-3) Selection of Hybridoma and Cloning

A hybridoma of interest is selected from cells obtained after the cell fusion treatment. As a selection method, a cell suspension is diluted with a fetal bovine serum-containing RPMI-1640 medium or the like, as appropriate and the diluted solution is then dispersed on a microtiter plate. A selective medium is added to each well and culture is then carried out while the selective medium is appropriately exchanged with a fresh one. As a result, cells that grow approximately 14 days after initiation of the culture in the selective medium can be obtained as hybridomas.

Subsequently, the presence or absence of an antibody against hDlk-1 in a culture supernatant of the growing hybridomas is screened. Such screening of hybridomas may be carried out in accordance with ordinary methods and thus the type of the screening method is not particularly limited. For example, a portion of the culture supernatant of the growing hybridomas contained in the well may be collected and such hybridomas may be then screened by ELISA, EIA, RIA, etc.

The fused cells may be cloned by limiting dilution or the like. An antibody exhibiting strong reactivity with hDlk-1 is determined by flowcytometry or the like and a hybridoma that produces the antibody is selected and is established as a clone.

(3-4) Collection of Monoclonal Antibody

As a method of culturing the established hybridomas and then collecting a monoclonal antibody from the obtained culture, a common cell culture method, an ascites formation method, etc. can be adopted. The term "culture" is used to mean that a hybridoma is allowed to grow in a culture dish or culture bottle, or that a hybridoma is allowed to proliferate in the abdominal cavity of an animal, as described below.

In the cell culture method, hybridomas may be cultured in an animal cell culture medium such as a 10% fetal bovine serum-containing RPMI-1640 medium, an MEM medium or a serum-free medium under common culture conditions (e.g. 37° C., 5% $CO_2$ concentration) for 7 to 14 days and an antibody may be then obtained from the culture supernatant.

In the ascites formation method, hybridomas are administered at a cell density of approximately $1 \times 10^7$ cells into the abdominal cavity of an animal of the same species as a mammal from which myeloma cells are derived, so as to cause proliferation of a large amount of hybridomas. Thereafter, ascites is preferably collected 2 to 3 weeks later.

In a case where an antibody should be purified in the aforementioned method for collecting the antibody, a suitable method is appropriately selected from known methods such as an ammonium sulfate salting-out method, ion exchange chromatography, gel filtration and affinity chromatography, or these methods are used in combination, so as to purify the aforementioned antibody.

(3-5) Selection of Clone Having Anti-Tumor Activity

The anti-hDlk-1 antibody of the present invention is an antibody having anti-tumor activity in vivo.

Herein, the term "anti-tumor activity" is used to mean activity of killing tumor cells (cancer cells) or inhibiting tumor growth. In the present invention, as such anti-tumor activity, tumor angiogenesis-inhibiting activity is preferable, for example. Moreover, the types of human tumors (tumor cells), on which the antibody of the present invention is able to exhibit anti-tumor activity, include: the aforementioned known human tumors in which expression of hDlk-1 had been confirmed (specifically, solid cancers such as neuroendocrine tumor, neuroblastoma, glioma, neurofibromatosis type 1, small cell lung cancer, liver cancer, kidney cancer and ovarian cancer and blood cancers such as myelodysplastic syndrome and acute myelocytic leukemia); and human colon cancer and human breast cancer in which expression of hDlk-1 has been newly confirmed by the present inventors. Of these, one or two or more types selected from human colon cancer, human breast cancer, human liver cancer and human neuroblastoma are particularly preferable.

The presence of anti-tumor activity in vivo can be confirmed by using a cancer-bearing mouse, in which desired tumor cells have been transplanted subcutaneously, and then administering the obtained antibody to the mouse. In this case, the antibody may be administered to the mouse immediately after transplantation of the tumor cells (a Prevention model), or the antibody may also be administered to the mouse after the tumor has grown up to a desired volume after transplantation (a Treatment model). An administration method is not limited. For example, the antibody may be administered into the abdominal cavity of the mouse once every 3 days at a dose of 20 mg/kg body weight via intraperitoneal administration. In the case of the Prevention model, the presence or absence of anti-tumor activity and the level thereof can be evaluated depending on tumor formation frequency and tumor volume. In the case of the Treatment model, the presence or absence of anti-tumor activity and the level thereof can be evaluated depending on tumor volume.

In the present invention, preferred examples of an anti-hDlk-1 antibody having anti-tumor activity in vivo include an anti-hDlk-1 monoclonal antibody (clone name: M3-1) produced by a hybridoma having accession No. FERM BP-10707, an anti-hDlk-1 monoclonal antibody (clone name: DI-2-14) produced by a hybridoma having accession No. FERM BP-10899 and an anti-hDlk-1 monoclonal antibody (clone name: DI-6) produced by a hybridoma having accession No. FERM BP-10900. Furthermore, an anti-hDlk-1 monoclonal antibody with a clone name of DI-2-14 can be preferably used as an antibody having high anti-tumor activity in vivo.

Herein, the hybridoma having accession No. FERM BP-10707 has been referred to as "Mouse-Mouse hybridoma: M3-1," and has been deposited with International Patent Organism Depositary (IPOD), National Institute of Advanced Industrial Science and Technology (AIST Tsukuba Central 6, Higashi 1-1-1, Tsukuba, Ibaraki, Japan, postal code: 305-8566), on Oct. 18, 2006. The hybridoma having accession No. FERM BP-10899 has been referred to as "Mouse-Mouse hybridoma DI-2-14," and has been deposited with the same above national institute on Aug. 21, 2007. The hybridoma having accession No. FERM BP-10900 has been referred to as "Mouse-Mouse hybridoma DI-6," and has been deposited with the same above national institute on Aug. 21, 2007.

Further, preferred examples of the anti-hDlk-1 antibody of the present invention include an anti-hDlk-1 antibody wherein the amino acid sequences of CDRs 1 to 3 of the H chain V region are the amino acid sequences as shown in SEQ ID NOS: 30 to 32, respectively and/or an anti-hDlk-1 antibody wherein the amino acid sequences of CDRs 1 to 3 of the L chain V region are the amino acid sequences as shown in SEQ ID NOS: 33 to 35, respectively. The aforementioned H chain V region preferably consists of the amino acid sequence as shown in SEQ ID NO: 23 and the aforementioned L chain V region preferably consists of the amino acid sequence as shown in SEQ ID NO: 25.

Still further, another preferred example of the anti-hDlk-1 antibody of the present invention is an anti-hDlk-1 antibody that binds to a site (e.g. an epitope), to which a monoclonal antibody produced by the hybridoma having accession No. FERM BP-10707, FERM BP-10899 or FERM BP-10900 binds (recognizes).

(3-6) Epitope of Anti-hDlk-1 Antibody

An epitope (an antigenic determinant) of the anti-hDlk-1 antibody of the present invention is not limited, as long as it is at least a portion of hDlk-1 as an antigen. For example, such an epitope is preferably at least a portion of a region consisting of amino acids at positions 26 to 85 (a region comprising EGF-1 to EGF-2 of hDlk-1), a region consisting of amino acids at positions 92 to 167 (a region comprising EGF-3 to EGF-4 of hDlk-1), or a region consisting of amino acids at positions 131 to 244 (a region comprising EGF-4 to EGF-6 of hDlk-1), in the amino acid sequence of hDlk-1 as shown in SEQ ID NO: 1. Among others, a region comprising EGF-4 to EGF-6 and a region comprising EGF-4 to EGF-6 of hDlk-1 are more preferable. A region consisting of amino acids at positions 92 to 120 (a region comprising EGF-3 of hDlk-1) is particularly preferable. An anti-hDlk-1 antibody that recognizes (binds to) such regions has high internalization activity into tumor cells, for example and thus it is extremely useful as an immunoconjugate as described later.

(4) Genetically Recombinant Antibody and Antibody Fragment (4-1) Genetically Recombinant Antibody In a preferred embodiment of the anti-hDlk-1 antibody of the present invention, there is provided a genetically recombinant antibody. The type of such a genetically recombinant antibody is not limited. Examples include a chimeric antibody, a humanized antibody and a human antibody.

A chimeric antibody (that is, a humanized chimeric antibody) is an antibody formed by ligating (conjugating) the variable region of a mouse-derived antibody to the constant region of a human-derived antibody (please refer to Proc. Natl. Acad. Sci. U.S.A. 81, 6851-6855, (1984), etc.). When such a chimeric antibody is produced, the thus ligated antibody can be easily constructed by a genetic recombination technique. As such variable regions of the mouse-derived antibody used herein, the H chain V region preferably consists of the amino acid sequence as shown in SEQ ID NO: 23, for example and the L chain V region preferably consists of the amino acid sequence as shown in SEQ ID NO: 25, for example.

When a humanized antibody is produced, a complementarity determining region (CDR) is transplanted from the variable region of a mouse antibody into the variable region of a human antibody, so as to produce a reconstructed variable region, in which a framework region (FR) is derived from the human and CDR is derived from the mouse (what is called CDR grafting (CDR transplantation)). Subsequently, the thus humanized, reconstructed human variable region is ligated to a human constant region. Such a method for producing a humanized antibody is well known in the present technical field (please refer to Nature, 321, 522-525 (1986); J. Mol. Biol., 196, 901-917 (1987); Queen C et al., Proc. Natl. Acad. Sci. USA, 86: 10029-10033 (1989); JP Patent Publication (Kohyo) No. 4-502408 A (1992) (Japanese Patent No. 2828340; Queen et al.), etc.) The type of a mouse-derived CDR sequence that can be used herein for the humanized anti-hDlk-1 antibody of the present invention is not limited. As preferred examples of such mouse-derived CDR sequences, the amino acid sequences as shown in SEQ ID NOS: 30 to 32 are preferable as the CDRs 1 to 3 of the H chain V region (in this order) and the amino acid sequences as shown in SEQ ID NOS: 33 to 35 are preferable as the CDRs 1 to 3 of the L chain V region (in this order).

In general, in the case of a human antibody (a complete human antibody), its structure comprising a Hyper Variable region that is the antigen-binding site of a V region, other parts of the V region and a constant region is the same as the structure of the antibody of a human. However, such a Hyper Variable site may also be derived from other animals. A technique of producing a human antibody is publicly known and a method for producing gene sequences that are common in humans by genetic engineering has been established. A human antibody can be obtained, for example, by a method using a human antibody-producing mouse that has human chromosomal fragments comprising the genes of the H chain and L chain of the human antibody (please refer to Tomizuka, K. et al., Nature Genetics, (1977) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y., Matsuda, T. and Iijima, S. eds.), Kluwer Academic Publishers; Tomizuka, K. et. al., Proc. Natl. Acad. Sci. USA, (2000) 97, 722-727, etc.), or by a method of obtaining a phage display-derived human antibody selected from a human antibody library (please refer to Wormstone, I. M. et. al, Investigative Ophthalmology & Visual Science., (2002) 43 (7), 2301-8; Carmen, S. et. al., Briefings in Functional Genomics and Proteomics, (2002) 1 (2), 189-203; Siriwardena, D. et. al., Opthalmology, (2002) 109 (3), 427-431, etc.).

In the case of the aforementioned chimeric antibody, humanized antibody and human antibody, the N-glycoside-linked sugar chain in the antibody Fc region is preferably a sugar chain, in which fucose does not bind to N-acetylglucosamine at the reducing terminal thereof. A specific example is an antibody consisting of genetically recombinant antibody molecules, which has, in the Fc region of the antibody molecules, a sugar chain in which the position 1 of the fucose does not bind to the position 6 of the N-acetylglucosamine at the reducing terminal of the N-glycoside-linked sugar chain via an $\alpha$ bond. Such an antibody is able to significantly improve ADCC activity. This point (the characteristics of the N-glycoside-linked sugar chain in the antibody Fc region) is preferable also for the aforementioned polyclonal antibody and monoclonal antibody.

(4-2) Antibody Fragment

The anti-hDlk-1 antibody fragment of the present invention is included in the antibody of the present invention. Herein, the antibody fragment of the present invention has binding activity to hDlk-1 and anti-tumor activity in vivo, as in the case of the anti-hDlk-1 antibody of the present invention.

The fragment of the antibody means a region of a portion of an anti-hDlk-1 polyclonal antibody or anti-Dlk-1 monoclonal antibody (namely, an antibody fragment derived from the anti-hDlk-1 antibody of the present invention). Examples of such an antibody fragment include peptides comprising, as at least a portion thereof, Fab, Fab', F(ab')$_2$, Fv (variable fragment of antibody), a single-stranded antibody (an H chain, an L chain, an H chain V region and an L chain V region, etc.), scFv, diabody (scFv dimer), dsFv (a disulfide-stabilized V region) and a complementarity determining region (CDR).

Fab is an antibody fragment with a molecular weight of approximately 50,000 having antigen-binding activity, which is formed by binding about a half of the N-terminal side of the H chain and the entire L chain via a disulfide bond, among fragments obtained by treating antibody molecules with a protease, papain. In addition, it is also possible to produce such Fab by inserting DNA encoding the Fab of an antibody into a prokaryote expression vector or a eukaryote expression vector and then introducing the vector into a prokaryote or a eukaryote so as to allow the DNA to express therein.

F(ab')$_2$ is an antibody fragment with a molecular weight of approximately 100,000 having antigen-binding activity, whose size is slightly greater than Fab that binds to Fab via disulfide bond in the hinge region, among fragments obtained by treating antibody molecules with a protease, pepsin. In addition, it is also possible to produce such F(ab')$_2$ by the thioether bond or disulfide bond of Fab, as described later.

Fab' is an antibody fragment with a molecular weight of approximately 50,000 having antigen-binding activity, which is formed by cleaving the disulfide bond in the hinge region of the aforementioned F(ab')$_2$. In addition, it is also possible to produce such Fab' by inserting DNA encoding the Fab' fragment of an antibody into a prokaryote expression vector or a eukaryote expression vector and then introducing the vector into a prokaryote or a eukaryote so as to allow the DNA to express therein.

scFv is an antibody fragment having antigen-binding activity, which is a VH-P-VL or VL-P-VH polypeptide formed by ligating a single H chain V region (VH) to a single L chain V region (VL) using a suitable peptide linker (P). Such scFv can be produced by obtaining cDNA encoding the VH and VL of an antibody, constructing DNA encoding scFv, inserting the DNA into an expression vector for prokaryote or an expression vector for eukaryote and then introducing the vector into a prokaryote or a eukaryote so as to allow the DNA to express therein.

Diabody is an antibody fragment formed by dimerization of scFv, which has divalent antigen-binding activities. Such divalent antigen-binding activities may be identical to each other, or they may also be different from each other. Such diabody can be produced by obtaining cDNA encoding the VH and VL of an antibody, constructing DNA encoding scFv such that the length of the amino acid sequence of P is 8 residues or less, inserting the DNA into an expression vector for prokaryote or an expression vector for eukaryote and then introducing the vector into a prokaryote or a eukaryote so as to allow the DNA to express therein.

dsFv is an antibody fragment formed by binding polypeptides, in which one amino acid residue in each of VH and VL has been substituted with a cysteine residue, to each other via a disulfide bond between the cysteine residues. The amino acid residue to be substituted with cysteine residues can be selected based on estimation of the three-dimensional structure of the antibody according to the method of Reiter et al. (Protein Engineering, 7, 697-704, 1994). Such dsFv can be produced by obtaining cDNA encoding the VH and VL of an antibody, constructing DNA encoding dsFv, inserting the DNA into an expression vector for prokaryote or an expression vector for eukaryote and then introducing the vector into a prokaryote or a eukaryote so as to allow the DNA to express therein.

A peptide comprising CDRs comprises at least one region of CDRs (CDRs 1 to 3) of VH or VL. A peptide multiple peptides comprising CDRs can be bound to one another, directly or via a suitable peptide linker. Such a peptide comprising CDRs can be produced by constructing DNA encoding the VH and VL of an antibody, inserting the DNA into an expression vector for prokaryote or an expression vector for eukaryote and then introducing the expression vector into a prokaryote or a eukaryote so as to allow the DNA to express therein. Moreover, such a peptide comprising CDRs can also be produced by chemical synthesis methods such as a Fmoc method (a fluorenylmethyloxycarbonyl method) and a tBoc method (a t-butyloxycarbonyl method).

The antibody fragment of the present invention, as is, may be an antibody fragment, which comprises a part of or the entire antibody Fc region in which fucose does not bind to N-acetylglucosamine at the reducing terminal of an N-glycoside-linked sugar chain. Otherwise, the antibody fragment of the present invention may also be a fusion protein, in which the aforementioned antibody fragment is fused with a part of or the entire antibody Fc region in which fucose does not bind to N-acetylglucosamine at the reducing terminal of an N-glycoside-linked sugar chain. Such an antibody fragment is able to significantly improve ADCC activity and thus it is preferable.

The type of the antibody fragment of the present invention is not limited. Specific examples include antibody fragments comprising, as at least a portion thereof, the amino acid sequences as shown in SEQ ID NOS: 30 to 32 (CDRs 1 to 3 of the H chain V region). A specific example is an antibody fragment comprising the amino acid sequence as shown in SEQ ID NO: 23 (the H chain V region). Moreover, examples of the antibody fragments also include antibody fragments comprising, as at least a portion thereof, the amino acid sequences as shown in SEQ ID NOS: 33 to 35 (CDRs 1 to 3 of the L chain V region). A specific example is an antibody fragment comprising the amino acid sequence as shown in SEQ ID NO: 25 (the L chain V region).

Hereinafter, in the descriptions of the present specification, the aforementioned antibody fragments are also included in the anti-hDlk-1 antibody of the present invention.

3. Preparation of Antibody-Agent Complex

As an immunoconjugate prepared using the aforementioned anti-hDlk-1 antibody of the present invention, there can be provided an antibody-agent complex, which comprises the aforementioned antibody and a compound having anti-tumor activity and/or cell-killing activity. It is to be noted that a complex formed by previously preparing each of the aforementioned antibody molecule and the aforementioned compound having anti-tumor activity and/or cell-killing activity, separately and then combining them is generally referred to as an immunoconjugate. On the other hand, a complex obtained by ligating a protein toxin used as such a compound having anti-tumor activity and/or cell-killing activity to an antibody gene on a gene according to a genetic recombination technique, so as to allow it to express as a single protein (a fusion protein), is generally referred to as an immunotoxin.

Examples of a compound having anti-tumor activity include doxorubicin, calicheamicin, mitomycin C and Auristatin E.

Examples of a compound having cell-killing activity include saporin, lysine, pseudomonas exotoxin and diphtheria toxin. Of these, saporin and pseudomonas exotoxin are preferably used.

A method for producing an antibody-agent complex is not limited. For example, a method of coupling an antibody with an agent via a disulfide bond or a hydrazone bond is applied.

The aforementioned anti-hDlk-1 antibody of the present invention is excellent in terms of internalization activity into target tumor cells that express hDlk-1. Thus, by previously combining a compound having anti-tumor activity and cell-killing activity with the anti-hDlk-1 antibody, it becomes possible to allow such a compound to directly and highly selectively act on the tumor cells. The antibody-agent complex of the present invention is extremely excellent in terms of ability to deliver the agent to the target tumor cells.

The internalization activity into cells can be evaluated by fluorescently labeling an antibody with rhodamine or the like and then observing the migratory behavior and localization of the antibody using a fluorescence microscope or the like.

Moreover, in the present invention, in addition to the aforementioned antibody-agent complex, there can also be provided an antibody fragment-agent complex, in which the aforementioned antibody fragment is used instead of an antibody. With regard to the details of such an antibody fragment-agent complex, the descriptions of the aforementioned antibody-agent complex can be applied, as appropriate.

Hereinafter, in the descriptions of the present specification, such an antibody fragment-agent complex is also included in the antibody-agent complex of the present invention.

4. Pharmaceutical Composition

The anti-hDlk-1 antibody and antibody-agent complex of the present invention are useful as active ingredients contained in a pharmaceutical composition.

The pharmaceutical composition is useful as a pharmaceutical composition for treating and/or diagnosing a tumor. In particular, since the anti-hDlk-1 antibody of the present invention and an antibody-agent complex comprising the aforementioned antibody have tumor angiogenesis-inhibiting activity as such anti-tumor activity, they are preferably used in the treatment of tumor. That is to say, the anti-hDlk-1 antibody and antibody-agent complex of the present invention are useful as active ingredients contained in a tumor therapeutic agent, a tumor angiogenesis inhibitor and a tumor diagnostic agent.

It is preferable to provide the pharmaceutical composition of the present invention in the form of a pharmaceutical composition comprising the anti-hDlk-1 antibody and/or antibody-agent complex of the present invention as active ingredient(s) and further comprising a pharmacologically acceptable carrier.

Target diseases (tumors), to which the pharmaceutical composition of the present invention is applied, include: the aforementioned known human tumors, in which expression of hDlk-1 had previously been confirmed; and human colon cancer and human breast cancer, in which expression of hDlk-1 has been confirmed by the present inventors. Among others, one or two or more types selected from colon cancer, human breast cancer, human liver cancer and human neurocytoma are particularly preferable. Such target disease may be a single disease, or two or more diseases may be developed in combination.

Examples of the "pharmacologically acceptable carrier" include an excipient, a diluent, an extender, a disintegrator, a stabilizer, a preservative, a buffer, an emulsifier, an aromatic, a coloring agent, a sweetener, a thickener, a corrigent, a solubilizer and other additives. Using one or more types of such carriers, a pharmaceutical composition can be prepared in the form of an injection, a liquid agent, a capsule, a suspension, an emulsion, a syrup, etc. These pharmaceutical compositions can be administered orally or parenterally. Another form for parenteral administration is an injection comprising one or more active ingredients, which is prepared by an ordinary method. Such an injection can be produced by dissolving or suspending the present antibody in a pharmacologically acceptable carrier such as a normal saline solution or a commercially available distilled water used for injection.

In particular, when an antibody fragment derived from the anti-hDlk-1 antibody of the present invention (particularly, an antibody fragment with a low molecular weight) is administered into a living body, a colloidal dispersion system can be used in addition to the aforementioned components. Such a colloidal dispersion system is anticipated to have an effect of enhancing the stability of a compound (an antibody fragment) in a living body or an effect of efficiently transporting such a compound to a specific organ, tissue, or cell. The type of such a colloidal dispersion system is not limited, as long as it is commonly used. An example of such a colloidal dispersion system is a dispersion system comprising, as a base, polyethylene glycol, a macromolecular complex, a macromolecular aggregate, a nanocapsule, microsphere, beads and lipids including an oil in water emulsifier, micelle, mixed micelle and liposome. Preferred examples of such a colloidal dispersion system include multiple liposomes and the vesicles of artificial membrane, which have an effect of efficiently transporting such a compound to a specific organ, tissue, or cell (Mannino et al., Biotechniques, 1988, 6, 682; Blume and Cevc, Biochem. et Biophys. Acta, 1990, 1029, 91; Lappalainen et al., Antiviral Res., 1994, 23, 119; Chonn and Cullis, Current Op. Biotech., 1995, 6, 698).

The dose of the pharmaceutical composition of the present invention differs depending on the age, sex, body weight and symptoms of a patient, therapeutic effects, an administration method, a treatment time, the types of the anti-hDlk-1 antibody and antibody-agent complex of the present invention contained in the pharmaceutical composition, etc. In general, the present pharmaceutical composition may be administered within the range between 600 μg and 6,000 mg per adult per administration. However, the dose is not limited to the aforementioned range.

In a case where the pharmaceutical composition is administered in the form of an injection, for example, it may be administered at a dose of 100 μg to 100 mg, per administration, per body weight of a human patient, once or divided over several administrations, as an average daily dose. Examples of the dosage form include intravenous injection, subcutaneous injection, intradermal injection, intramuscular injection and intraperitoneal injection. Of these, intravenous injection is preferable. In addition, such an injection may be prepared in the form of a nonaqueous diluent (e.g. polyethylene glycol, vegetable oil such as olive oil, alcohols such as ethanol, etc.), a suspension, or an emulsion. Such an injection can be sterilized by mechanical sterilization using a filter, the mixing of a microbicide, etc. The injection can be produced in the form of an injection to be prepared before using. That is, a sterilized solid composition is prepared by a freeze-drying method or the like and the composition is then dissolved in sterilized distilled water used for injection or other solvents before it is used, so that it can be then used.

The present invention provides the use of the aforementioned anti-hDlk-1 antibody and/or antibody-agent complex of the present invention in production of a pharmaceutical (an agent) for treating and/or diagnosing a tumor. In addition, the present invention provides the aforementioned anti-hDlk-1 antibody and/or antibody-agent complex of the present invention, which are used for treating and/or diagnosing tumor.

Moreover, the present invention provides a method for treating and/or diagnosing a tumor, which comprises using (namely, administering to patients) the aforementioned anti-hDlk-1 antibody and/or antibody-agent complex of the present invention. Furthermore, the present invention also provides the use of the aforementioned anti-hDlk-1 antibody and/or antibody-agent complex of the present invention in the treatment and/or diagnosis of a tumor.

5. Method for Detecting Tumor

The method for detecting a tumor of the present invention is characterized in that it comprises allowing the aforementioned anti-hDlk-1 antibody of the present invention to react with a sample collected from a living body (hereinafter referred to as a biological sample) and detecting a signal of the reacted antibody.

As described above, since hDlk-1 has been confirmed to be specifically expressed in various types of tumor cells, hDlk-1 and particularly, free hDlk-1 (an extracellular region portion of hDlk-1) can be used as a marker for various types of tumors. In particular, such hDlk-1 can be preferably used as a marker for human colon cancer, human breast cancer and human liver cancer.

Thus, the anti-hDlk-1 antibody of the present invention is allowed to react with a biological sample and a signal of the reacted antibody is then detected, so as to detect a tumor. The obtained antibody signal can be used as an indicator of the amount of an antigen in the biological sample (that is, an hDlk-1 amount or a free hDlk-1 amount). In detection of the tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flowcytometry and the like can be used. In radioimmunoassay, a labeled antibody is used and thus an antibody signal is expressed as the amount of the labeled antibody that is directly detected. Otherwise, an antibody whose concentration or antibody titer has been known may be used as a standard solution and thus a signal of the target antibody may be expressed as a relative value. That is, both the standard solution and the analyte may be measured using a measurement device and an antibody signal in a biological sample may be expressed as a value relative to the value of the standard solution used as a criterion. Examples of such radioimmunoassay include the ELISA method, the EI method, the RIA method, fluorescence immunoassay (FIA) and luminescence immunoassay. Of these, the ELISA method is particularly preferable in that it is simple and highly sensitive.

In the present invention, the state of tumor can be evaluated or diagnosed, using the detection result obtained by the aforementioned detection method as an indicator. For example, when the detection result exceeds a predetermined standard value, the state of tumor is defined as tumor positive and when the detection result is less than the predetermined standard value, it is defined as tumor negative. In the case of tumor positive, it is determined that a certain type of tumor could have been developed and thus the tumor state can be evaluated. The term "the state of tumor" is used herein to mean the presence or absence of the development of tumor, or the progression degree thereof. Thus, specific examples of the state of tumor include the presence or absence of the development of tumor, the progression degree thereof, the degree of malignancy, the presence or absence of metastasis and the presence or absence of recurrence.

In the aforementioned evaluation, as a state of tumor to be evaluated, only one state may be selected from the aforementioned examples, or multiple examples may be combined and selected. The presence or absence of tumor can be evaluated by determining whether or not the tumor has been developed, with reference to the predetermined standard value used as a boundary, based on the obtained detection result. The degree of malignancy is used as an indicator that indicates the progression degree of cancer. Based on the detection result, the target tumor can be classified into a certain disease stage and it can be evaluated. Otherwise, early cancer and advanced cancer can be distinguished from each other and then they can be evaluated. For example, it is also possible to determine the target tumor as early cancer or advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

6. Kit for Detecting or Diagnosing Tumor

The anti-hDlk-1 antibody of the present invention can be provided in the form of a kit for detecting or diagnosing a tumor. The kit of the present invention comprises a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an Eppendorf tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc.

The kit of the present invention can be effectively used to carry out the aforementioned detection method of the present invention and thus it is extremely useful.

Hereinafter, the present invention will be more specifically described in the following examples. However, these examples are not intended to limit the scope of the present invention.

EXAMPLE 1

<Materials and Method>

1. Cell Lines

HEK-293-hDlk, 7E2-C-hDlk and Huh-7-hDlk cell lines were produced in accordance with the descriptions of WO 2005/052156 and they were used. Moreover, human neuroblastoma SK-N-F1 cells were acquired from the American Type Culture Collection (ATCC; catalog No. CRL2142).

SW480-hDlk cells were obtained by introducing an expression vector, pcDNA-hdlk-Flag (please refer to WO 2005/052156) that contained a full-length hDlk-1 gene, into a human colon cancer-derived cell line, SW480 (obtained from the Laboratory of Cell Growth and Differentiation, Institute of Molecular and Cellular Biosciences, University of Tokyo), then selecting cells using an antibiotic G418 (geneticin, GIBCO BRL) and then establishing a cell line that stably expressed hDlk-1.

2. Preparation of Anti-hDlk-1 Polyclonal Antibody

In order to construct an hDlk-1 extracellular region (FA-1) expression vector, the following primers were designed and synthesized.

```
Forward (F) primer:
5'-cgcgtccgcaaccagaagccc-3'        (SEQ ID NO: 3)

Reverse (R) primer:
5'-ctcgaggtgctccggctgctgcaccggc-3' (SEQ ID NO: 4)
```

To design the R primer, restriction enzyme sequence digested by XhoI was added to the R primer. PCR reaction was carried out with the following composition of a reaction solution under the following reaction conditions using these primers and cDNA of hDlk-1 as a template.

<<Composition of Reaction Solution>>

| | |
|---|---|
| Template DNA: | 1 µL |
| 10 × PCR buffer: | 5 µL |
| 2.5 mM dNTP: | 4 µL |
| Taq DNA polymerase: | 0.5 µL |
| F primer (10 µM): | 1 µL |
| R primer (10 µM): | 1 µL |
| Sterilized water: | 37.5 µL |
| Total: | 50 µL |

<<Reaction Conditions>>

One cycle consisting of "heat denaturation/dissociation: 95° C. (60 sec) → Annealing: 55° C. (60 sec) → Synthesis/elongation: 72° C. (60 sec)" was repeated 35 times (total 35 cycles).

The obtained cDNA of hDlk-1 extracellular region (human FA1) was cloned into a pCRII vector (Invitrogen) (pCRII-hFA1). The cloned human FA1 cDNA was confirmed by a sequencer.

An EcoRI/XhoI fragment containing the human FA1 cDNA was cut out of the pCRII-hFA1 and it was then inserted into the EcoRI/XhoI site of a pcDNA4/Myc-His vector (Invitrogen) (pcDNA4-hFA1). An Myc tag and an His tag were added to the C-terminal of Dlk-1 protein of this expression vector and thus human FA1 was expressed as fusion protein with the Myc tag and the His tag. The fusion protein was used as an antigen and a rabbit was immunized with the antigen according to an ordinary method, so as to prepare an anti-hDlk-1 polyclonal antibody.

3. Preparation of EGF-like Motif-Deficient Mutant of hDlk-1 Gene

For use in the epitope analysis of the anti-hDlk-1 monoclonal antibody, EGF-like motif-deficient mutants of the hDlk-1 gene were prepared, as described below.

First, primers used for amplifying the target region by a PCR method were prepared. The prepared primer sequences are as shown in the following Table 1. To prepare the primers, a restriction enzyme sequence digested with NotI was added to the F primer and a restriction enzyme sequence digested with XbaI was added to the R primer. However, such a restriction enzyme sequence digested with XbaI was not added to the R primer used for amplifying EGF (4-6) and EGF (5-6) regions. It is to be noted that, in the "construct" column in Table 1, the notaion such as "EGF (1-4)" means contiguous regions from EGF-1 to EGF-4 in the 6 EGF-like motifs (EGF-1 to EGF-6) existing in the FA-1 region of hDlk-1.

TABLE 1

| Construct | Primer name * | Primer sequence | SEQ ID NO: |
|---|---|---|---|
| EGF(1-4) | Y403Not | 5'-gcggccggctgaatgcttcccggcc-3' | 5 |
| | Y402Xba | 5'-tctagagaggctgttggccacgatctcgc-3' | 6 |
| EGF(1-3) | Y403Not | 5'-gcggccggctgaatgcttcccggcc-3' | 7 |
| | Y410Xba | 5'-tctagacccgtccttttctggcagtcc-3' | 8 |
| EGF(1-2) | Y403Not | 5'-gcggccggctgaatgcttcccggcc-3' | 9 |
| | Y405Xba | 5'-tctagaggcccgaacatctctatcac-3' | 10 |
| EGF(4-6) | Y409Not | 5'-gcggccgcaaaaaggacgggccctgtg-3' | 11 |
| | Rv | 5'-gcgtatagtaagctctgcgg-3' | 12 |
| EGF(5-6) | Y401Not | 5'-caggcagcggccgcgagatcgtggccaac-3' | 13 |
| | Rv | 5'-gcgtatagtaagctctgcgg-3' | 14 |

*With regard to each construct, the upper case indicates the F primer and the lower case indicates the R primer.

Using each of the aforementioned primers, PCR was carried out with the following composition of a reaction solution under the following reaction conditions.

<<Composition of Reaction Solution>>

| Template DNA: | 1 μL |
|---|---|
| 10 × PCR buffer: | 5 μL |
| 2.5 mM dNTP: | 4 μL |
| Taq DNA polymerase: | 0.5 μL |
| F primer (10 μM): | 1 μL |
| R primer (10 μM): | 1 μL |
| Sterilized water: | 37.5 μL |
| Total: | 50 μL |

<<Reaction Conditions>>

One cycle consisting of "heat denaturation/dissociation: 95° C. (60 sec) → Annealing: 55° C. (60 sec) → Synthesis/elongation: 72° C. (60 sec)" was repeated 35 times (total 35 cycles).

Each fragment amplified by the PCR method was cloned into a pCRII vector (Invitrogen) using a TA cloning kit (Invitrogen) and the nucleotide sequence thereof was then confirmed. Thereafter, a fragment was obtained by cleavage with NotI/XbaI and this fragment was then subcloned into the NotI/XbaI site of pME18S-CFHX-FXYD TM. It is to be noted that the pME18S-CFHX-FXYD TM is an expression vector (obtained from the Laboratory of Cell Growth and Differentiation, Institute of Molecular and Cellular Biosciences, University of Tokyo), which has been designed such that the expressed protein of interest could have the signal sequence of human CD8a (GenBank Accession No. NM_001768) and a His tag sequence at the N-terminus thereof.

4. Preparation of Anti-hDlk-1 Monoclonal Antibody (1) Cell Immunization, Protein Antigen Immunization The hDlk-1-expressing cell lines (HEK-293-hDlk cells, 7E2-C-hDlk cells) and the FA-1 region of hDlk-1 (hereinafter referred to as hFA-1) prepared by the aforementioned method were used as antigen. In the case of the hDlk-1-expressing cell lines, $1 \times 10^7$ cells were mixed with an immunization adjuvant (complete Freund's adjuvant; Wako Pure Chemical Industries, Ltd.) or TITERMAX GOLD®(Funakoshi Corp.) at a mixing ratio of 1:1. In the case of the hFA-1 protein, 20 .mu.g of the protein was mixed with an immunization adjuvant (complete Freund's adjuvant; Wako Pure Chemical Industries, Ltd.) or TITERMAX GOLD®(Funakoshi Corp.) at a mixing ratio of 1:1. Thus, an emulsion was prepared by such mixing and it was then injected into both footpads of 6-week-old rats (Wister) and mice (C57/BL6, Balb/c) (initial immunization). Three days and ten days after the initial immunization, booster was carried out. On the day after the final immunization, the lymph nodes of both patellas were collected from them and lymphocytes were then prepared therefrom. For booster, a cell suspension formed by suspending $5 \times 10^6$ cells in PBS was used in the case of cell immunization. In the case of a protein antigen, 5 μg in a PBS solution was used. On the day after the final immunization, the lymph nodes of both patellas were collected from them and lymphocytes were then prepared therefrom. For the booster, a cell suspension using PBS was used as an antigen. The thus prepared lymphocytes were mixed with a mouse myeloma cell line (P3-X63-Ag8.653) at a mixing ratio of 3:1 and cell fusion was then carried out by a polyethylene glycol method. A selective medium containing HAT (aminopterin, hypoxanthine and thymidine) was used and the cells were cultured in a 96-well flat-bottom plate, a 5% CO.sub.2 incubator.

The cells were cultured for 10 to 14 days and a culture supernatant of the proliferating hybridomas was subjected to a first screening according to Cell ELISA (as described later) and was then subjected to a second screening according to FACS analysis using HEK-293 cells. Thereafter, hybridoma clones that produce anti-hDlk-1 monoclonal antibodies were prepared by a limiting dilution method.

(2) DNA Immunization

Likewise, for the purpose of preparing anti-hDlk-1 monoclonal antibodies, using a method called a DNA immunization method, monoclonal antibodies that recognize the three-dimensional structure of hDlk-1 and inhibit the physiological activity of the organism were produced. In the case of the DNA immunization method, since an hDlk-1 gene incorporated into the introduced expression vector is expressed in the body of a mouse, it becomes possible to present an antigen, while maintaining the original three-dimensional structure or various types of modifications after translation (e.g. sugar chain modification, a disulfide cross-linking, etc.). Thus, an attempt was made to produce a specific monoclonal antibodies that recognizes the original three-dimensional structure of hDlk-1 and inhibits the physiological activity of the organism, although the production of such a specific monoclonal antibody would be difficult when the conventional denatured protein or synthetic peptide was used as an immunogen.

The full-length cDNA of hDlk-1 was incorporated into a tag-added mammal expression vector. Whether or not the produced gene construct was expressed on a cell surface, as it had been designed, was examined before immunization, using mammalian cells. That is to say, the produced gene construct was transiently introduced into mammalian cells. The gene construct-introduced mammalian cells were cultured in a $CO_2$ incubator for 24 hours and they were then used in FCM analysis. For such FCM analysis, an antibody that reacts with the tag added to the aforementioned introduced gene was added to the culture solution containing the gene-introduced cultured cells and the solution was then left at rest for 30 minutes. Thereafter, a fluorescently-labeled secondary antibody that specifically recognizes the tag was added to the reaction solution and the solution was then left at rest for 30 minutes. Thereafter, the reaction solution was used in FCM analysis. It was demonstrated that the gene construct produced in the present invention was expressed on the cell surface.

In order to develop anti-hDlk-1 monoclonal antibody that recognizes the three-dimensional structure of hDlk-1 and inhibits the physiological activity of the organism, various types of gene constructs as constructed above were used singly or in combination and they were introduced into an animal to be immunized according to various gene introduction methods (intramuscular injection, electroporation, or a gene gun) (for approximately 2 to 3 months). In order to analyze serum collected from the immunized animal, the aforementioned HEK293-hDlk cells were used. Serum collected from the animal immunized with the aforementioned introduced gene was added to a culture supernatant containing the HEK293-hDlk cells and the culture supernatant was then left at rest for 30 minutes. Thereafter, a fluorescently-labeled secondary antibody that specifically recognizes the immunoglobulin of the immunized animal was added to the reaction solution. After the solution had been left at rest for 30 minutes, it was used in FCM analysis. An animal which produces a specific antibody that strongly recognizes the HEK293-hDlk cells was anatomized and B cells were then isolated from the animal according to an ordinary method, so as to produce anti-hDlk-1 monoclonal antibodies.

5. Purification of Antibody

The hybridoma clones produced by the aforementioned method were administered at a cell density of $3\times10^6$ cells into the abdominal cavity of a BALB/c nude mouse, to which 2,6,10,14-tetramethylpentadecane (pristine) had previously (7 days before) been administered. Two weeks later, ascites was collected. Thereafter, affinity purification was performed on this ascites using a protein G column (HITRAP™ protein G; GE Healthcare Biosciences) after caprylic acid precipitation, so as to obtain an anti-hDlk-1 monoclonal antibody produced by each hybridoma clone. The subsequent analyses were carried out using the thus purified anti-hDlk-1 monoclonal antibodies.

6. Labeling of Antibody

In order to classify the produced anti-hDlk-1 monoclonal antibodies based on the epitopes or in order to evaluate internalization activity, the obtained antibodies were labeled. The biotin labeling of the antibody was carried out using ECL Protein Biotinylation module (GE Healthcare Biosciences; RPN2202). The rhodamine labeling of the antibody was carried out using EZ-LABEL™ Rhodamine Protein Labeling kit (Pierce; 53002). The FITC labeling of the antibody was carried out using EZ-LABEL™ Fluorescein Isothiocyanate (FITC) Protein Labeling kit (Pierce; 53004). The manual included with each kit was used.

7. Cell ELISA

The aforementioned 7E2-C(hdlk) cell line was seeded at a cell density of $7.5\times10^3$ cells/well into a gelatin-coated 96-well culture plate (Corning) and the cells were then cultured at 37° C. for 2 days. After the cells were washed with ice-cold PBS and they were then fixed with a 4% paraformaldehyde solution and were then treated with a 0.2% TRITON™-X-100 (product name) solution, so as to obtain a plate used for cell ELISA. Thereafter, an ELISA method was carried out according to an ordinary method. Specific procedures are as follows.

First, blocking was carried out using a 1% BSA-PBS solution at room temperature for 2 hours. Subsequently, a hybridoma supernatant was added thereto and the mixture was reacted at room temperature for 1 hour. Thereafter, the cells (or plates) was washed with a 0.1% TWEEN® 20 (product name)-PBS solution 3 times. Biotinylated anti-rat IgG (Vector Laboratory) was diluted 100-fold with a 0.1% TWEEN® 20-PBS solution and it was used as a secondary antibody. The cells were allowed to react with it at room temperature for 1 hour and the cells were then washed with a 0.1% TWEEN® 20-PBS solution 3 times. Thereafter, horseradish peroxidase-streptavidin (HRP; Vector Laboratory) diluted 1,000-fold with a 0.1% TWEEN® 20-PBS solution was further allowed to react with the cells at room temperature for 1 hour and the cells was then washed with a 0.1% TWEEN® 20-PBS solution 3 times. A TMB (3,3',5,5'-tetramethylbenzidine; SIGMA) substrate solution was added to the cells to carry out a chromogenic reaction and 1 M sulfuric acid was then added to the reaction solution to terminate the reaction. Using Microplate reader Model 550 (Bio-Rad), absorbance was measured.

8. FACS Analysis

The cells were removed from the culture dish by a trypsin treatment and a cell suspension (cell density: $5\times10^6$ cells/mL) was then prepared. Thereafter, 0.5 μg of an anti-human Dlk monoclonal antibody was allowed to react with 100 .mu.L of the cell suspension at 4° C. for 30 minutes. After the reaction product had been washed with PBS, it was allowed to react with PE-labeled anti-mouse IgG or PE-labeled anti-rat IgG (both of which were available from BD Pharmingen) (0.5 μg) at 4° C. for 30 minutes, followed by analysis using FACS-CALIBUR™ (Becton, Dickinson and Company).

9. Calculation of Dissociation Constant (Kd Value) by ELISA Method

The antigen affinity (Kd value) of the produced anti-hDlk-1 monoclonal antibody was calculated by a method using ELISA (Djavadi-Ohaniance L. et al. (1996), In Antibody Engineering, Chapter 4, pp. 77-97. IRL Press, Oxford).

Specifically, the purified recombinant hFA-1 protein (1 µg/mL) was added to a 96-well culture plate (Corning) to fix as an antigen (at room temperature for 1 hour). Subsequently, the plate was washed with PBS 3 times and 2% skim milk (PBS solution) was added thereto for blocking (at room temperature for 1 hour). After the plate had been washed with PBS 2 times, an antigen-antibody complex formed by previously mixing an antigen solution (a purified hFA-1 protein; 50, 25, 12.5, 6.25 and 3.125 nM) with each clone of the anti-hDlk-1 monoclonal antibody (0.5 nM) and then equilibrating the mixture was added to the aforementioned ELISA plate for a reaction (at room temperature for 1 hour). After the plate had been washed with PBS 3 times, it was allowed to react with HRP-labeled anti-mouse IgG (final concentration: 1 µg/mL) or HRP-labeled anti-rat IgG (final concentration: 1 µg/mL) (both of which were available from GE Healthcare Biosciences), which had been diluted with a blocking solution, at room temperature for 1 hour.

10. Epitope Analysis of Anti-Human Dlk-1 Monoclonal Antibody

The prepared approximately 100 types of anti-hDlk-1 monoclonal antibodies were classified using epitopes recognizing them. Each of the aforementioned expression vectors, hdlk-EGF(1-3)/pME18S-CFHX, hdlk-EGF (3-4)/pME18S-CFHX and hdlk-EGF (4-6)/pME18S-CFHX, was introduced into COS-7 cells. 24 to 72 hours after the gene introduction, the cells were removed from a culture dish by a trypsin treatment and the type of an EGF-like motif of hDlk-1 recognized by each antibody clone was then examined by FACS analysis.

11. Immunohistostaining Method

A human cancer tissue array (Cybrdi; colon cancer tissue array Lot: CC05-01-001; breast cancer tissue array Lot: CC08-02-002) was subjected to a deparaffinization treatment. Thereafter, it was subjected to an antigen activation treatment using an autoclave (121° C., 5 minutes) in a 10 mM citric acid buffer (pH 6.0) and it was then used in staining using an anti-hDlk-1 polyclonal antibody. A chromogenic reaction was carried out using DAB (3,3'-diaminobenzidine) as a substrate and thereafter, nuclear staining was carried out using hematoxylin as counter staining. Specifically, the following operations were carried out.

A section, which had been fixed with neutral formalin and had been then embedded in paraffin, was subjected to a deparaffinization treatment and then to an antigen activation treatment using an autoclave (121° C., 5 minutes) in a 10 mM sodium citrate solution. Subsequently, the resultant section was treated at room temperature for 20 minutes with a solution formed by adding a hydrogen peroxide solution to methanol to a final concentration of 0.3%, so as to eliminate endogenous peroxidase activity. Thereafter, the section was washed with PBS at room temperature for 5 minutes 2 times and it was then blocked for 30 minutes using a BLOCK-ACE reagent (Dainippon Pharmaceutical Co., Ltd.), so as to conduct an operation to block nonspecific binding sites in the tissues. Subsequently, an anti-hDlk-1 polyclonal antibody (final concentration: 0.5 µg/mL), which had been diluted with a 1/10 diluted BLOCK-ACE reagent, was allowed to react with the section at room temperature for 1 hour and it was then washed with PBS for 5 minutes 3 times. Subsequently, a biotinylated anti-rabbit IgG antibody which had been diluted 100-fold with a 1/10 diluted BLOCK-ACE reagent, was allowed to react with the section at room temperature for 1 hour and it was then washed with PBS for 5 minutes 3 times. Thereafter, reagents in an ABC kit were mixed in accordance with the instruction included therewith to produce an ABC complex and it was then allowed to react with the section at room temperature for 30 minutes. The resultant was washed with PBS for 5 minutes 3 times and a chromogenic reaction was then carried out using a peroxidase substrate (0.02% DAB (3,3'-diaminobenzidine), a 0.03% hydrogen peroxide solution and 50 mM Tris-HCl (pH 7.5)). After confirmation of color development, the reaction product was washed with water for 10 minutes and the nucleus was then stained with a Mayer's hematoxylin solution (Wako Pure Chemical Industries, Ltd.). Thereafter, it was dehydrated with alcohol, penetrated with xylene and then embedded with ENTELLAN® New (Merch Japan).

12. Preparation of Cancer-Bearing Mice and Evaluation of Drug Efficacy of Anti-hDlk-1 Monoclonal Antibody (1) Prevention Model A liver cancer cell line (Huh-7-hDlk) that expresses hDlk-1 was removed by a trypsin treatment and it was then added to PBS to prepare a cell suspension at a cell density of $6 \times 10^7$ cells/mL. The suspension was mixed with an equal amount of matrigel (BD Pharmingen) on ice. Using a 26 G syringe, 100 µl ($3 \times 10^6$ cells) of the mixture was subcatenously injected into the right flank of each 6-week-old female nude mouse (Balb/c, nu/nu). On the day of transplantation of the cancer cells, the mice were divided into several groups and administration of an antibody (20 mg/kg body weight; intraperitoneal administration) was initiated. Thereafter, the same above administration was carried out at intervals of once every 3 days. Anti-tumor activity was evaluated based on tumor formation frequency and tumor volume. Such tumor volume was calculated using the following expression:

$$\text{Tumor volume } (\text{mm}^3) = (\text{minor axis})^2 \times (\text{major axis}) \times \pi/6$$

(2) Treatment Model

A liver cancer cell line (Huh-7-hDlk) that expresses hDlk-1 and a colon cancer cell line (SW480-hDlk) that expresses hDlk-1 were removed by a trypsin treatment and each cell line was then added to PBS to prepare a cell suspension at a cell density of 6.times.10.sup.7 to 10.times.10.sup.7 cells/mL. The suspension was mixed with an equal amount of MATRIGEL™ (BD Pharmingen) on ice. Using a 26 G syringe, 100 µL ($3 \times 10^6$ to $5 \times 10^6$ cells) of the mixture was subcutaneously injected into the right flank of each 6-week-old female nude mouse (Balb/c, nu/nu). Ten to fourteen days after transplantation of the cancer cells, mice whose tumor volume had become 50 to 150 mm$^3$ (mean value: approximately 100 mm$^3$) were divided into several groups. The day on which the mice were divided was defined as a first day (Day 1) and administration of an antibody was initiated on that day. The antibody was intraperitoneally administered to the mice at intervals of once every 3 days (20 mg/kg body weight). Anti-tumor activity was evaluated by measuring tumor volume. A significant difference test was carried out by a Student's-t-test and when the obtained value was P<0.05 was determined to be statistically significant.

13. Evaluation of Internalization Activity of Anti-hDlk-1 Monoclonal Antibody

Internalization activity, by which an hDlk-1 monoclonal antibody is incorporated into cells mediated by endocytosis after it has bound to an antigen, depends on an epitope recognized by the antibody. Thus, the internalization activity of the produced anti-hDlk-1 monoclonal antibodies were evaluated. As a method for evaluating internalization activity by FACS analysis, such internalization activity was evaluated by FACS analysis and observation under a fluorescence microscope.

Evaluation of internalization activity by FACS analysis was carried out by the following method. An anti-hDlk-1 monoclonal antibody (0.5 μg) was added to HEK-293-hdlk cells (2 ×10⁵ cells) for reaction (4° C., 20 minutes) and the cells were then washed with PBS 2 times. Thereafter, the cells was suspended in a DMEM medium, followed by incubation at 37° C. (60 minutes, 90 minutes, 120 minutes and 240 minutes), so as to promote the internalization of an antigen-antibody complex on the cell surface. Thereafter, the cells were centrifuged (1,000 rpm, 5 minutes) to recover them and the recovered cells were then allowed to react (4° C., 20 minutes) with PE-labeled anti-mouse (or rat) IgG (0.5 μg). Thereafter, the cells were analyzed by FACSCALIBUR (Becton, Dickinson and Company).

Such as same method, an FITC-labeled anti-hDlk-1 monoclonal antibody was allowed to react with HEK-293-hdlk cells by the same above method and the cells were then washed with PBS 2 times. Thereafter, the cells were suspended in a DMEM medium, followed by incubation at 37° C. (120 minutes). The cells were then analyzed by FACS-CALIBUR (Becton, Dickinson and Company).

Moreover, a rhodamine-labeled anti-hDlk-1 monoclonal antibody (0.5 μg) was added to HEK-293-hdlk cells (2×10⁵ cells) for reaction (4° C., 20 minutes) and the cells were then washed with PBS 2 times. Thereafter, the cells were suspended in a DMEM medium, followed by incubation at 37° C. (15 minutes, 30 minutes, 60 minutes and 120 minutes). Thereafter, a smear preparations were prepared by Cytospin (Shandon) (800 rpm, 3 minutes) and the smear preparations were then entraped using a mounting solution (Vector Laboratory). Thereafter, localization of an antigen-antibody complex was observed under a fluorescence microscope (Nikon; Eclipse E800).

14. Preparation of Immunoconjugate Using Anti-hDlk-1 Monoclonal Antibody

Saporin, a plant-derived protein toxin, was conjugated with an anti-hDLk-1 monoclonal antibody clone M3-1 (mouse IgG1) having high internalization activity after binding to an antigen and with a clone M1-290 (mouse IgG2b) used as a control, so as to prepare immunoconjugates (Advanced Targeting System, San Diego).

15. Evaluation of Drug Efficacy of Immunoconjugates Using Anti-hDlk-1 Monoclonal Antibody Cells were removed from a culture dish by a trypsin treatment and a cell suspension was prepared at a cell density of 1×10⁵ cells in a DMEM medium, to which 10% FBS had been added. The cell suspension was inoculated at a cell density of 1×10⁴ cells/well on a 96-well flat-bottom plate coated with collagen and the cells were then cultured for 2 to 3 hours, so that the cells were adhered thereto. Subsequently, various types of immunoconjugates such as mouse IgG-saporin (IgG-SAP), M3-1-saporin (M3-1-SAP) and M1-290-saporin (M1-290-SAP) were added to the cells. Each immunoconjugate was added thereto in concentrations of 0.1, 1, 10, 100 and 1,000 ng/mL. 48 to 72 hours after the culture, absorbance was measured by an MTT method.

Anti-tumor activity in vivo was evaluated, using cancer-bearing mice in which the aforementioned Huh-7-hDlk cells were used.

16. MTT Method

TetraColor ONE (Seikagaku Corp.) was added to cells cultured on a 96-well plate and they were then reacted in a 5% CO₂ incubator for 3 to 4 hours. After completion of the reaction, the 96-well plate was directly applied to a Microplate Reader, so as to measure the absorbance at a wavelength of 490 nm (a control wavelength: 655 nm).

<Results>

1. Analysis of Tumor Growth-Inhibiting Activity of Known Anti-hDlk-1 Monoclonal Antibodies (1C1, 4C4 and 31C4) in Human Liver Cancer Cell Xenografts (Prevention Models)

hDlk-1 is expressed on the surfaces of various types of cancer cells. If an hDlk-1 gene is stably expressed in a human liver cancer cell line, a tumor growth rate is significantly promoted when the aforementioned gene is transplanted subcutaneously in a nude mouse (please refer to WO 2005/052156). Thus, an anti-hDlk-1 antibody is considered to be useful as a cancer therapeutic agent. Since the gene sequence/amino acid sequence of the hDlk-1 itself are known, in principle, it is possible to obtain a monoclonal antibody against hDlk-1 according to a known method using a synthetic peptide or a purified protein as an immunogen. However, in general, the possibility of actually producing an antibody exhibiting activity as a cancer therapeutic agent, namely, an antibody exhibiting anti-tumor activity at an individual level (in vivo) is still unknown and it cannot be estimated from the type of an antigen, an expression level, a protein structure, etc. Among approximately several tens of thousands types of monoclonal antibodies, those that have been placed on the market as therapeutic agents for diseases including tumors (cancers) as typical examples are only approximately 20 types. As is clear from this fact, a majority of antibodies do not exhibit pharmaceutical effects at an individual level.

It has been known that known anti-hDlk-1 monoclonal antibodies (clones 1C1, 4C4 and 31C4) kill human liver cancer cells in the presence of, at least, a complement (please refer to WO 2005/052156). However, the pharmaceutical effects of such antibodies in vivo have been unknown.

First, the anti-tumor activity in vivo of each of the three known clones was examined by transplanting a liver cancer cell line (Huh-7-hDlk) that expresses hDlk-1 subcutaneously in a nude mouse, initiating administration of the antibody at the same time of the transplantation and then analyzing the effect of the antibody on the implantation of the tumor cells subcutaneously in the nude mouse and the tumor growth.

As shown in Table 2 below, in a case where administration of the antibody was initiated at the same time of the cell transplantation, on the 14$^{th}$ day (Day 14), tumor was formed in all 10 individuals in a control group (rat IgG administered) (mean tumor volume: 382.0±74.8 mm³). On the other hand, in the case of anti-hDlk-1 monoclonal antibody administration groups, the tumor formation rate was 40% in the 1C1 administration group and it was 30% in the 4C4 administration group and 31C4 administration group. Thus, the tumor formation rate was significantly low in the anti-hDlk-1 monoclonal antibody administration groups. Even on the 21$^{st}$ day (Day 21), the tumor formation rate was 70% in the 1C1 administration group and it was 50% in the 4C4 administration group and 31C4 administration group. Thus, in all the antibody administration groups, tumor formation was inhibited by administration of the antibody. The volume (mean value) of the formed tumor in the antibody administration groups was lower than that in the control group. However, a statistically significant difference was not found between the two types of groups.

TABLE 2

|  | Administration group | N (Number of mice) | Tumor formation rate | Tumor volume (mm³) |
|---|---|---|---|---|
| Day 14 | Rat IgG | 10 | 100% (10/10) | 382.0 ± 74.8 |
|  | 1C1 | 4 | 40% (4/10) | 656.2 ± 241.21 |
|  | 4C4 | 3 | 30% (3/10) | 77.1 ± 30.0 |
|  | 31C4 | 3 | 40% (3/10) | 156.5 ± 55.8 |

TABLE 2-continued

|  | Administration group | N (Number of mice) | Tumor formation rate | Tumor volume (mm³) |
|---|---|---|---|---|
| Day 18 | Rat IgG | 10 | 100% (10/10) | 979.2 ± 152.7 |
|  | 1C1 | 6 | 60% (6/10) | 646.7 ± 280.8 |
|  | 4C4 | 5 | 50% (5/10) | 371.7 ± 118.2 |
|  | 31C4 | 5 | 50% (5/10) | 474.5 ± 163.1 |
| Day 21 | Rat IgG | 10 | 100% (10/10) | 1464.4 ± 207.6 |
|  | 1C1 | 7 | 70% (7/10) | 899.25 ± 308.4 |
|  | 4C4 | 5 | 50% (5/10) | 653.5 ± 212.8 |
|  | 31C4 | 5 | 50% (5/10) | 770.1 ± 216.1.8 |

2. Analysis of Tumor Growth-Inhibiting Activity of Known Anti-hDlk-1 Monoclonal Antibodies (1C1, 4C4 and 31C4) in Human Liver Cell Xenografts (Treatment Models)

In order that an anti-hDlk-1 monoclonal antibody may exhibit its pharmaceutical effect as a cancer therapeutic antibody, it is extremely important for the antibody to exhibit its anti-tumor activity on the established tumor tissues. In addition, in the aforementioned Prevention models, the anti-tumor activity of an antibody can be presumed to a certain extent by making a comparison among the tumor formation rates. However, such tumor formation rates vary widely among individuals and thus, anti-tumor activity cannot be accurately evaluated.

Thus, Huh-7-hDlk cells were transplanted subcutaneously in a nude mouse and the pharmaceutical effect of each antibody was evaluated using Treatment models, in which administration of the antibody was initiated at a stage where the mean tumor volume had become 100 mm³.

As shown in FIG. 1, in the case of such Treatment models, each of 1C1 (rat IgG1) (FIG. 1A), 4C4 (rat IgG2a) (FIG. 1B) and 31C4 (rat IgG2a) (FIG. 1C) was administered at a dose of 20 mg/kg body weight into the abdominal cavity of the nude mouse and the effect of the antibody on tumor growth was then analyzed. However, as a result, all clones did not exhibit significant tumor growth-inhibiting activity.

3. Analysis of Anti-Tumor Activity of Novel Anti-hDlk-1 Monoclonal Antibody in Vivo in Human Liver Cancer Cell Xenografts (Treatment Models)

It is essential for a cancer therapeutic antibody that targets hDlk-1 to specifically kill tumor tissues that express hDlk-1 or to exhibit activity of inhibiting tumor growth in Xenograft Treatment models.

Anti-hDlk-1 monoclonal antibodies (approximately 100 clones), which were newly produced in the invention of the present application, were evaluated also using Xenograft Treatment models in which Huh-7-hDlk cells were used. Among the newly produced approximately 100 clones, a majority of clones did not exhibit their pharmaceutical effect in the Treatment models, as with the three known clones. Nevertheless, several clones exhibiting significant tumor growth-inhibiting activity, such as clones DI-2-14, 2-13, BA-1-3D, DI-6 and M3-1, were obtained.

In the clone DI-2-14 (mouse IgG1) administration group, after administration of the antibody, tumor growth was inhibited in all individuals (N=8). On the 14$^{th}$ day (Day 14) after initiation of the administration of the antibody, the tumor volume was 175.5±46.5 mm³ (P<0.01 by Student's t-test) in the clone DI-2-14 administration group, whereas it was 907.7±142.8 mm³ in the control group (N=8) (FIG. 2A). When the tumor volume at the time of initiation of the administration of the antibody was defined as 1.0, the tumor volume on the 14$^{th}$ day (Day 14) was 1.85 in the clone DI-2-14 administration group, whereas it was 9.24 in the control group. The weight of the tumor excised was 0.15±0.04 (g) (P<0.01 by Student's t-test) in the clone DI-2-14 administration group, whereas it was 0.58±0.07 (g) in the control group (FIG. 2B).

As shown in FIG. 2C, the anti-tumor activity of the clone DI-2-14 administered was reproduced in another independent test. In the same manner as described above, at a stage where the mean value of the tumor volume had reached 100 mm³ (control group: 103.8±11 mm³ (N=7); DI-2-14 administration group: 101.4±9.5 mm³ (N=8)), administration of the antibody was initiated. On the 14$^{th}$ day (Day 14) after initiation of the administration, the tumor volume of the clone DI-2-14 administration group was 148.83±32.65 mm³ (P<0.01 by Student's t-test), whereas it was 733.37±244.86 mm³ in the control group.

In the clone 2-13 (rat IgG2b) administration group (N=10), it was not perfect but the tumor growth rate was statistically significantly inhibited. On the 14$^{th}$ day (Day 14) after initiation of the administration of the antibody, the tumor volume of the clone 2-13 administration group was 832.9±131.8 mm³ (P<0.01 by Student's t-test), whereas it was 1580.2±179.4 mm³ in the control group (N=10). Thus, the clone 2-13 exhibited a tumor growth-inhibiting activity of approximately 50% (FIG. 3A).

Likewise, in the clone BA-1-3D (mouse IgG2a) administration group (N=8) and the clone DI-6 (mouse IgG1) administration group (N=8), the tumor volume was 380.8±54.4 mm³ (FIG. 3B) in the BA-1-3D administration group and it was 321.0±59.6 mm³ (FIG. 3C) in the clone DI-6 administration group, whereas it was 907.7±142.8 mm³ in the control group (N=8). Thus, tumor growth was significantly inhibited by both types of antibodies (P<0.01 by Student's t-test).

Moreover, in the clone M3-1 (mouse IgG1) administration group (N=8) as well, the tumor growth rate was significantly inhibited. On the 14$^{th}$ day (Day 14) after initiation of the administration, the tumor volume was 457.0±123.75 mm³ in the clone M3-1 administration group (P<0.05 by Student's t-test), whereas it was 1123.8±249.1 mm³ in the control group (N=7) (please refer to FIG. 3D and Table 3).

Among the aforementioned clones, a hybridoma that produces the clone M3-1 was referred to as "Mouse-Mouse hybridoma: M3-1," and it was deposited with the NITE Patent Microorganisms Depositary (NPMD), the National Institute of Advanced Industrial Science and Technology, an Independent Administrative Institution under the Ministry of Economy, Trade and Industry, (the AIST Tsukuba Central 6, Higashi 1-1-1, Tsukuba, Ibaraki, Japan, postal code: 305-8566), on Oct. 18, 2006 (accession No. FERM BP-10707).

A hybridoma that produces the clone DI-2-14 was referred to as "Mouse-Mouse hybridoma: M3-1," and it was deposited with the same above national institute on Aug. 21, 2007 (accession No. FERM BP-10899).

Likewise, a hybridoma that produces the clone DI-6 was referred to as "Mouse-Mouse hybridoma: M3-1," and it was deposited with the same above national institute on Aug. 21, 2007 (accession No. FERM BP-10900).

TABLE 3

| Group | N (number of mice) | Tumor volume (mm³) | Growth rate (-fold) | Tumor weight (g) |
|---|---|---|---|---|
| Mouse IgG (control) | 8 | 907.7 ± 142.8 | 9.42 | 0.58 ± 0.07 |
| DI-2-14 | 8 | *175.5 ± 46.5 | 1.85 | *0.15 ± 0.04 |
| DI-6 | 8 | *321.0 ± 59.6 | 3.41 | **0.37 ± 0.06 |
| BA-1-3D | 8 | *380.8 ± 54.4 | 4.06 | *0.34 ± 0.06 |

TABLE 3-continued

| Group | N (number of mice) | Tumor volume (mm³) | Growth rate (-fold) | Tumor weight (g) |
|---|---|---|---|---|
| Mouse IgG (control) | 7 | 1123.8 ± 249.1 | 9.61 | n.e.. |
| M3-1 | 8 | **457.0 ± 123.75 | 4.1 | n.e.. |
| Rat IgG (control) | 10 | 1580.2 ± 179.4 | 14.5 | n.e.. |
| 2-13 | 10 | *832.9 ± 131.8 | 7.5 | n.e.. |

4. Analysis of Anti-Tumor Activity in Human Colon Cancer Cell Xenografts (Treatment Models)

As in the case of using the aforementioned human liver cancer cell Xenograft Treatment models, the anti-tumor activity of the clone 2-13 in human colon cancer cell line (SW480-hDlk) Xenograft Treatment models was analyzed (FIG. 4).

In a clone 2-13 administration group, tumor growth was significantly inhibited when compared with a control group (a rat IgG administration group). On the 16$^{th}$ day (Day 16), the tumor volume was 452.71±54.97 mm³ (which corresponded to 2.87, when the value on the administration initiation day was defined as 1.0) in the clone 2-13 administration group (N=8) (P<0.05 by Student's t-test), whereas it was 877.27±176.82 mm³ (which corresponded to 5.01, when the value on the administration initiation day was defined as 1.0) in the rat IgG administration group (N=7) (FIG. 4).

From the above results, it became clear that the anti-hDlk-1 monoclonal antibody exhibits significant tumor growth-inhibiting activity in vivo, not only in liver cancer cells, but also in colon cancer cells.

5. Antigen-Binding Activity of Anti-hDlk-1 Monoclonal Antibodies (Clones DI-2-14, 2-13, BA-1-3D, DI-6 and M3-1) (FACS Analysis Using HEK-293-hDlk Cells and Calculation of Dissociation Constant by ELISA)

With regard to the anti-hDlk-1 monoclonal antibodies that exhibited significant anti-tumor activity in human cancer cell Xenograft models, their affinity for hDlk-1 as an antigen was analyzed by FACS using HEK-293-hDlk cells (FIG. 5) and Huh-7-hDlk cells (FIG. 6). As a result, it was demonstrated that all clones recognized all cell lines and that they recognized the three-dimensional structure of hDlk-1. Although data was not given, all clones did not recognize at all HEK293 cells and Huh-7 cells that did not express hDlk-1.

Subsequently, the affinity (dissociation constant) of these clones for an antigen was calculated by the aforementioned ELISA method. As a result, the Kd value of the clone DI-2-14 was found to be $9.26 \times 10^{-9}$ (M), that of the clone M3-1 was found to be $6.28 \times 10^{-9}$ (M), that of the clone BA-1-3D was found to be $32.2 \times 10^{-9}$ (M) and that of the clone DI-6 was found to be $10.1 \times 10^{-9}$ (M). The affinity of the clone 2-13 for the purified recombinant hFA-1 was not high and thus the Kd value thereof could not be calculated by the aforementioned method.

6. Epitope Analyses of Anti-hDlk-1 Monoclonal Antibodies

Next, the epitope analyses of anti-hDlk-1 monoclonal antibodies were carried out.

Each of expression vectors hDlk (EGF 1-2)-pME-CHFX, hDlk (EGF 1-3)-pME-CHFX, hDlk (EGF 3-4)-pME-CHFX, hDlk (EGF 4-6)-pME18-CHFX and hDlk (EGF 5-6)-pME18-CHFX (FIG. 7) was introduced into COS-7 cells and they were then subjected to FACS analysis and the immunostaining of Cytospin specimens, so as to examine sites in a region containing 6 EGF-like motifs existing in the FA-1 region (extracellular region) of hDlk-1, which were recognized by each anti-hDlk-1 monoclonal antibody.

As a result of the FACS analysis and immunostaining, it was found that the clone DI-2-14 recognized EGF (1-3) and EGF (3-4), but that it did not recognize at all EGF (1-2), EGF (4-6) and EGF (5-6) (FIG. 8). It was demonstrated that the epitope recognized by the clone DI-2-14 may be a region containing the 3$^{rd}$ EGF-like motif (EGF-3) of hDlk-1 to the 4$^{th}$ EGF-like motif (EGF-4) thereof (a region comprising amino acids at positions 92 to 167 of hDlk-1) and that it may be EGF-3 (a region comprising amino acids at positions 92 to 120 of hDlk-1). It has been reported that, among mouse IgG isotypes, IgG2a and IgG2b have strong antibody-dependent cytotoxic activity (ADCC) and that the ADCC of IgG1 is low (please refer to Kipps, T. J. et al., 1985). The isotype of the clone DI-2-14 is mouse IgG1. Thus, it was demonstrated that the extremely strong tumor growth-inhibiting activity of the clone DI-2-14 inhibits the functions of hDlk-1 at a level higher than cancer cell cytotoxic activity via effector cells, such as ADCC activity and thus that it exhibits anti-tumor activity. Hence, it was demonstrated that a region containing EGF-3 and EGF-4 of hDlk-1 and particularly, EGF-3 is a domain especially important for the functions of hDlk-1.

Moreover, the clones 2-13, DI-6 and BA-1-3D recognized EGF (1-2) and EGF (1-3), but they did not recognize at all EGF (3-4) and EGF (4-6) (FIG. 9). It was shown that the epitopes recognized by the three above clones are a region containing the 1$^{st}$ EGF-like motif (EGF-1) to the 2$^{nd}$ EGF-like motif (EGF-2) of hDlk-1 (a region comprises amino acids at positions 26 to 85 of hDlk-1). Thus, it was shown that the region containing the EGF-1 and EGF-2 of hDlk-1 is a domain especially important for the functions of the hDlk-1.

Furthermore, the clone M3-1 recognized EGF(1-4) and EGF(4-6), but it did not recognize EGF(1-2), EGF(1-3) and EGF(3-4) (FIG. 10). It was shown that the epitope recognized by the clone M3-1 is a region comprising the 4$^{th}$ EGF-like motif (EGF-4) to the 6$^{th}$ EGF-like motif (EGF-6) of hDlk-1 (a region comprising amino acids at positions 131 to 244 of hDlk-1). Thus, it was shown that the region containing the EGF-4, EGF-5 and EGF-6 of hDlk-1 is a domain especially important for the functions of the hDlk-1.

7. Internalization Activity of Anti-hDlk-1 Monoclonal Antibody

The produced anti-hDlk-1 monoclonal antibody clones were classified based on epitopes recognized by the clones. Regarding the thus classified clones belonging to several groups, their internalization activity after recognition of antigens was examined.

With regard to clone M1-290 recognizing EGF(1-2), clone M3-1 recognizing EGF(4-6) and clone M3-4 recognizing EGF(5-6), each antibody was allowed to react with HEK293-hDlk cells, followed by incubation at 37° C. Thereafter, it was allowed to react with a PE-labeled anti-mouse antibody. As shown in FIG. 11A, when the fluorescence intensity obtained without incubation was defined as 100%, when compared with other clones, the fluorescence intensity of the Clone M3-1 was reduced at a significantly rapid rate, depending on the incubation time. This result demonstrated that, after completion of an antigen-antibody reaction, the amount of an antigen-antibody complex on the cell surface is reduced by being internalized into the cells time-dependently. The fluorescence intensity after each incubation time is as follows.

60 minutes; M3-1: 38.7%, M1-290: 52.1%, M3-4: 74.1%
90 minutes; M3-1: 36.9%, M1-290: 47.1%, M3-4: 71.15%
120 minutes; M3-1: 28.1%, M1-290: 36.3%, M3-4: 57.3%
240 minutes; M3-1: 12.2%, M1-290: 31.2%, M3-4: 41.4%

It was confirmed that the factor of reduction of a mean fluorescence intensity after incubation is not the removal of the anti-hDlk-1 monoclonal antibody from an antigen, which has bound to the antigen during the incubation. The clone M3-1 was directly labeled with FITC and it was then allowed to react with HEK293-hDlk cells in the same above manner. After washing with PBS, it was incubated at 37° C. for 120 minutes. Thereafter, FACS analysis was carried out and the fluorescence intensity obtained immediately after the reaction was compared with the fluorescence intensity obtained 120 minutes after the incubation. As a result, there was no significant difference between the two types of fluorescence intensity (without incubation: 100%; 120 minutes after the incubation: 110.9%) (FIG. 11B).

Subsequently, the rhodamine-labeled antibody was allowed to react with HEK293-hDlk cells. After washing with PBS, it was incubated at 37° C. in the same above manner. Thereafter, a smear preparations were prepared using Cytospin and localization of the fluorescence-labeled antibody was observed under a fluorescence microscope. As a result, as shown in FIG. 12, without incubation, localization of the antibody into the cell membrane was observed. However, in the case of the clones M3-1 and DI-1 that recognize EGF(4-6), the clones were incorporated into the cells due to endocytosis by incubation at 37° C. for only 15 minutes and they were then incorporated into vesicles, so that intracellular localization of the clones was observed such as dots. On the other hand, in the case of the clones M1-290 and M3-4, a majority of them were localized in the cell membrane, although localization was observed such as dots (FIG. 12).

From the aforementioned results, it was found that antibodies recognizing EGF(4-6), such as the clone M3-1, had significantly high internalization activity after recognition of antigens, when compared with other antibodies recognizing other domains. Accordingly, since an immunoconjugate of an anti-hDlk-1 antibody such as the clone M3-1 and an anti-cancer agent or cytotoxin is rapidly incorporated into a target cell, it is considered that the immunoconjugate exhibits high pharmacological effect of the anticancer agent or cytotoxin and that it has a few side effects.

8. Cytotoxic Activity of Anti-hDlk-1 Monoclonal Antibody Immunoconjugate

Saporin was allowed to bind to each of the clone M3-1 having internalization activity and to the clone M1-290 used as a control, so as to prepare immunoconjugates (M3-1-SAP and M1-290-SAP). Thus, the pharmaceutical effects of these immunoconjugates were evaluated and thus the effectiveness of a missile therapy using an immunoconjugate of the anti-hDlk-1 monoclonal antibody was analyzed. Both M3-1-SAP and M1-290-SAP did not exhibit at all toxicity to HEK293 cells that did not express hDlk-1.

Subsequently, these immunoconjugates were added to Huh7-hDlk cells and SK-N-F1 cells (endogenous hDlk-1-expressing neuroblastoma) that expressed hDlk-1 and they were then cultured. As a result, a control (mouse IgG-SAP) exhibited almost no cytotoxic activity on all cells. However, when M3-1-SAP was added to the culture solution and was then cultured, the cells were damaged concentration-dependently. In the case of a concentration of 1 µg/mL, the survival rate was found to be 23.3±1.35% (N=3) in the Huh-7-hDlk cells and it was found to be 9.38±2.1% (N=3) in the SK-N-F1 cells. Thus, M3-1-SAP exhibited strong cytotoxic activity (FIG. 13).

The cytotoxic activity of M3-1-SAP on the SK-N-F1 cells (endogenous hDlk-1-expressing neuroblastoma) was compared with the cytotoxic activity of M1-290-SAP on the same above cells. As a result, as shown in FIG. 13B, the activities of the these immunoconjugates were almost equivalent to each other (FIG. 13B).

9. Tumor Growth-Inhibiting Activity in Vivo of Anti-hDlk-1 Monoclonal Antibody Immunoconjugates The effectiveness of M3-1-SAP as an immunoconjugate, namely, its anti-tumor activity and side effects occurring when it is administered to individual mice, were evaluated using Huh-7-hDlk cell Xenograft models. M1-290-SAP was used as a control. Anti-tumor activity was evaluated based on tumor volume in the same manner as that described above. Side effects were analyzed based on a change in body weight and a mortality rate after administration of such immunoconjugates.

In a mouse IgG administration group (N=8), an increase or decrease in body weight was not observed throughout the test period (14 days). On the other hand, in an M3-1-SAP (5 mg/kg body weight; intraperitoneal administration) administration group (N=8) and an M1-290-SAP (5 mg/kg body weight; intraperitoneal administration) administration group (N=8), a decrease in body weight was observed on the $4^{th}$ day (Day 4) after initiation of the administration of each immunoconjugate (in the case of "M3-1-SAP," Day 1: 21.2±1.36 (g), Day 4: 18.5±1.44 (g); in the case of "M1-290-SAP," Day 1: 21.13±0.81 (g), Day 4: 17.9±0.85 (g)). In particular, the toxicity of M1-290-SAP which has low internalization activity was strong, two out of the eight mice died on the $4^{th}$ day (Day 4) and the remaining six mice died on the $5^{th}$ day (Day 5). Thus, as a result, 5 days after initiation of the administration, all the mice died (FIG. 14B).

On the other hand, all mice in the M3-1-SAP administration group survived and their body weight was recovered after the $8^{th}$ day (Day 8).

Also, as shown in FIG. 15, tumor growth was strongly inhibited in the M3-1-SAP administration group. On the $14^{th}$ day (Day 14), the tumor volume in the control group was found to be 1123.8±245.65 mm$^3$, whereas the tumor volume in the M3-1-SAP administration group was found to be 415.8±105.1 mm$^3$ (P<0.05 Student's t-test) (the immunoconjugate was administered twice, on Day 1 and Day 4).

Moreover, in order to confirm the anti-tumor activity of M3-1-SAP, M3-1-SAP was locally administered to a tumor portion (1 mg/mL M3-1-SAP, 40 µL/tumor). M3-1-SAP and control IgG were administered twice, namely, on the time point at which the tumor volume became a predetermined volume (control group: 144.98±6.1 mm$^3$ (N=5); M3-1-SAP group: 145.87±21.26 mm$^3$ (N=5)) and on the $4^{th}$ day (Day 4) after initiation of the administration. Thereafter, the growth of tumor volume was observed.

As a result, as shown in FIG. 17A, in the M3-1-SAP administration group, the growth of tumor was almost completely inhibited until the $7^{th}$ day (Day 7) (control group: 584.02±137.07 mm$^3$; M3-1-SAP group: 148.67±38.0 mm$^3$; P<0.01 by Student's t-test). Even on the $14^{th}$ day, the tumor volume in the M3-1-SAP administration group was found to be 575.75±216.61 mm$^3$ (P<0.05 by Student's t-test), whereas the tumor volume in the control group was found to be 2038.66±333.17 mm$^3$. Thus, M3-1-SAP exhibited extremely strong anti-tumor activity.

As shown in FIG. 16B, even in the case of intratumoral administration of M3-1-SAP, after the second administration on the $4^{th}$ day (Day 4), all mice survived, although their body weight reduction was slightly observed. After the $9^{th}$ day (Day 9), their body weight was gradually recovered and on the $10^{th}$ day (Day 10), it was completely recovered to a normal condition before administration.

On the other hand, as shown in FIG. 16C, when an existing anti-cancer agent Cisplatin (anti-malignant tumor agent Randa Injection; Nippon Kayaku Co., Ltd.) was administered, tumor growth was almost completely inhibited by administration of 5 mg/kg of the agent (on the 16$^{th}$ day, control group (PBS group): 1085.36±286.30 mm$^3$; Cisplatin group: 77.28±15.20 mm$^3$; P<0.01 by Student's t-test). However, as shown in FIG. 16D, in the Cisplatin administration group, a significant decrease in body weight was observed over time. On the 16$^{th}$ day (Day 16), the body weight of mice in the Cisplatin administration group was found to be 13.24±1.83 g (P<0.01 by Student's t-test), whereas the body weight of mice in the control group was found to be 20.58±0.53 g. Thus, a significantly strong side effect (body weight reduction) was observed.

The above results demonstrated that, when the clone M3-1 having high internalization activity (an antibody recognizing EGF(4-6)) is used as an immunoconjugate, it has a few side effects and high anti-tumor activity, when compared with other clones.

10. Expression of hDlk-1 in Human Colon Cancer Tissues and Breast Cancer Tissues It has previously been reported that hDlk-1 is expressed in solid cancers such as neuroendocrine tumor, neuroblastoma, glioma, neurofibromatosis type 1, small cell lung cancer, liver cancer, kidney cancer and ovarian cancer and in blood cancers such as myelodysplastic syndrome and acute myelocytic leukemia.

In order to examine expression of hDlk-1 in cancers other than the aforementioned cancers, a commercially available human cancer tissue array was immunostained with an anti-hDlk-1 antibody and expression of hDlk-1 in various cancers was analyzed. The hDlk-1 positive rate in colon cancer was examined using a colon cancer tissue array (Cybrdi; lot No. CC05-01-001). FIG. 17 shows representative stained photographs. Seventy specimens of colon cancer tissues were examined. As a result, in the case of adenocarcinoma, 12 out of 43 specimens (27.9%) were strongly positive and 19 specimens thereof (44.2%) were weakly positive. In such adenocarcinoma cases as a whole, 31 out of 43 analytes (72.1%) were hDlk-1 positive (Please refer to Table 4).

Moreover, in the case of 11 specimens of papillary adenocarcinoma in the same tissue array, 6 analytes (54.5%) were strongly positive to hDlk-1 (please refer to Table 4).

TABLE 4

|  | hDlk-1 negative | hDlk-1 weakly positive | hDlk-1 strongly positive |
|---|---|---|---|
| Adenocarcinoma |  |  |  |
| Grade I | 0 | 2 | 1 |
| Grade II | 4 | 13 | 8 |
| Grade III | 8 | 4 | 3 |
| Total | 12 | 19 | 12 |
| Papillary adenocarcinoma |  |  |  |
| Grade I | 0 | 3 | 3 |
| Grade II | 1 | 2 | 3 |
| Grade III | 0 | 0 | 0 |
| Total | 1 | 5 | 6 |

The hDlk-1 positive ratio in breast cancer was examined using a breast cancer tissue array (Cybrdi; lot No. CC08-02-002). This tissue array is composed of total 63 sections collected from 53 specimens and 17 specimens (17 sections) thereof were derived from infiltrating duct carcinoma, 2 specimens (2 sections) thereof were derived from intraductal carcinoma, 34 specimens (44 sections) thereof were derived from normal tissues or non-cancerous tissues such as collagen fibers. Its stained level, however was extremely low, although hDlk-1 was weakly positive in the specimens from normal mammary gland tissues (FIG. 18). On the other hand, 5 out of 17 specimens (29%) of infiltrating duct carcinoma were strongly positive to hDlk-1 (please refer to FIG. 18, Table 5).

TABLE 5

| Infiltrating duct carcinoma | hDlk-1 negative | hDlk-1 weakly positive | hDlk-1 strongly positive |
|---|---|---|---|
| Grade I | 1 | 0 | 0 |
| Grade II | 7 | 3 | 5 |
| Grade III | 0 | 1 | 0 |
| Total | 8 | 4 | 5 |

Intraductal carcinoma (2 analytes): hDlk-1 strongly positive (1), hDlk-1 negative (1)
Normal mammary gland, collagen fiber, etc. (34 analytes): hDlk-1 negative (24), hDlk-1 weakly positive (10)

It became clear that hDlk-1 was strongly expressed in approximately 30% of both colon cancer and breast cancer, as well as in the previously known hDlk-1-expressing cancers. As described in the aforementioned example, an anti-hDlk-1 monoclonal antibody exhibited anti-tumor activity on Xenograft models of colon cancer cells, as well as on Xenograft models of liver cancer cells. Thus, the anti-hDlk-1 monoclonal antibody becomes a therapeutic agent effective for colon cancer, as well as for liver cancer. Similarly, it also becomes an effective therapeutic agent that targets breast cancer or other hDlk-1-expressing cancer cells.

EXAMPLE 2

1. Dose-Dependent Anti-Tumor Activity of Mouse Anti-Human Dlk-1 Antibody (Clone DI-2-14) in Human Dlk-1-Expressing Liver Cancer Cell Line (Huh-7-Dlk Cells) Xenograft Treatment Models <Purpose>

As described in Example 1, the clone DI-2-14 (mouse IgG1) that is an anti-human Dlk-1 monoclonal antibody exhibited extremely high anti-tumor activity, at a dose of 20 mg/kg body weight, in the human liver cancer cell line (Huh-7-hDlk cells) Xenograft Treatment models. Thus, in order to further examine the anti-tumor activity of the clone DI-2-14, dose-dependent anti-tumor activity was evaluated.

<Method>

Anti-tumor activity was evaluated in the same manner as that described in Example 1, except for the dose of the antibody was changed.

<Results>

As shown in FIG. 19, the growth of tumor was dose-dependently inhibited by administration of the clone DI-2-14. On the 8$^{th}$ day (Day 8) after administration of the antibody, the tumor volume was found to be 522.76±107.9 mm$^3$ in the DI-2-14 (1 mg/kg) administration group (N=9), it was found to be 309.2±58.9 mm$^3$ in the DI-2-14 (2 mg/kg) administration group (N=9) and it was found to be 285.8±38.2 mm$^3$ in the DI-2-14 (5 mg/kg) administration group (N=9). In contrast, in the control group (N=9), the tumor volume was found to be 782.1±124.4 mm$^3$.

2. Anti-Tumor Activity of Mouse Anti-Human Dlk-1 Antibody (Clone DI-2-14) in Human Neuroblastoma SK-N-F1 Cell Xenograft Treatment Models <Purpose>

As described in Example 1, among 5 types of anti-human Dlk-1-monoclonal antibodies that exhibited anti-tumor activity in human liver cancer cell line (Huh-7-hDlk cells) Xenograft Treatment models, with regard to the clone DI-2-14 (mouse IgG1) exhibiting particularly strong anti-tumor activity, its anti-tumor activity in the Xenograft Treatment models of human neuroblastoma (SK-N-F1cells) was evaluated. Huh-7-Dlk cells are considered to be a cell line, in which a human Dlk-1-gene was allowed to extrinsically stably express in Huh-7 cells. In contrast, SK-N-F1 cells are considered to be a cell line, in which Dlk-1 is endogenously expressed on the cell surface. Accordingly, a phenomenon whereby the clone DI-2-14 exhibits anti-tumor activity in such an SK-N-F1 cell line Xenograft Treatment model when it is administered thereto is identical to a phenomenon whereby an anti-human Dlk-1 monoclonal antibody exhibits its pharmaceutical effect on human neuroblastoma cells. At the same time, it can also be said that the anti-human Dlk-1 monoclonal antibody (in particular, clone DI-2-14) is effective for (exhibits its pharmaceutical effect on) various types of cancer cells, which express Dlk-1 on the cell surface.

<Method>

Human neuroblastoma (SK-N-F1 cells; ATCC catalog No. CRL2142) that endogenously express hDlk-1 on the cell surface was removed by a trypsin treatment and a cell suspension ($6 \times 10^7$ cells/mL) was then prepared with PBS. The cell suspension was mixed with an equal amount of matrigel (BD Pharmingen) on ice. Using a 26 G syringe, 100 µL ($3 \times 10^6$ cells) of the mixture was injected under the skin of the right flank of each 6-week-old female severe combined immunodeficiency mouse (NOD-scid). Ten to fourteen days after transplantation of the cancer cells, mice whose tumor volume had grown to 50 to 150 mm$^3$ (mean value: 100 mm$^3$) were divided into several groups. The day at which the mice were divided into several groups was defined as a first day (Day 1) and administration of an antibody (clone DI-2-14) was initiated. The antibody was intraperitoneally administered at intervals of once every 3 days (5 mg/kg body weight, 20 mg/kg body weight). As with Example 1, anti-tumor activity was evaluated by measuring tumor volume. In addition, on the final day of the experiment, tumor was excised by an autopsy and the tumor weight was measured and evaluated. A significant difference test was carried out by a Student's t-test and it was determined that P<0.05 was statistically significant.

<Results>

As shown in FIG. 20A, in the case of the clone DI-2-14 (mouse IgG1) administration group, tumor growth was significantly inhibited in both the 5 mg/kg administration group (N=8) and the 20 mg/kg administration group (N=7), when compared with the control group (N=7). In particular, in the 20 mg/kg administration group (N=7), from the following day of initiation of the administration to the 23$^{rd}$ day (Day 23) at which the experiment was completed, the tumor volume relative to the same above day was statistically significantly small (P<0.01 by Student's t-test).

On the 23$^{rd}$ day (Day 23) after initiation of the administration, the tumor volume was found to be 333.8±6.8 mm$^3$ (P<0.01 by Student's t-test) in the clone DI-2-14 (5 mg/kg body weight) administration group and it was found to be 233.0±16.4 mm$^3$ (P<0.01 by Student's t-test) in the clone DI-2-14 (20 mg/kg body weight), whereas it was found to be 527.8±48.9 mm$^3$ in the control group. Thus, the dose-dependent anti-tumor activity of the clone DI-2-14 was confirmed (DI-2-14 (5 mg/kg) vs DI-2-14 (20 mg/kg), Day 23, P<0.01 by Student's t-test).

The weight of the tumor excised was found to be 0.03±0.009 (g) (P<0.05 by Student's t-test) in the clone DI-2-14 (5 mg/kg body weight) administration group and it was found to be 0.02±0.005 (g) (P<0.05 by Student's t-test) in the clone DI-2-14 (20 mg/kg body weight) administration group, whereas it was found to be 0.07±0.04 (g) in the control group. As in the case of tumor volume, there was a significant difference in tumor weight between the 5 mg/kg clone ID-2-14 administration group and the 20 mg/kg clone DI-2-14 administration group (P<0.05 by Student's t-test). Thus, dose-dependent anti-tumor activity was confirmed (FIG. 20B).

3. Determination of Variable Region Sequence of Antibody Gene of Mouse Anti-Human Dlk-1-Antibody (clone DI-2-14) and Construction of Chimeric DI-2-14 Expression Vector Mouse anti-human Dlk-1 monoclonal antibody-producing hybridomas were cultured in a DMEM medium containing 10% fetal bovine serum at 37° C. in a 7.5% CO$_2$ incubator. Total RNA was extracted from $3 \times 10^6$ hybridomas, using a TRIzol reagent (Invitrogen). Thereafter, employing GeneRacer Kit (Invitrogen), cDNA was synthesized according to a method included with the kit, using oligo dT primers. A gene encoding each of the variable regions of the H chain and L chain (VH and VL) of the clone DI-2-14 (mouse IgG1) was cloned by a PCR method using the synthesized cDNA as a template and a primer included with the GeneRacer Kit as a 5'-primer were used. On the other hand, with regard to a 3'-primer, a primer having a sequence complementary to a mouse γ1 constant region is used as a 3'-primer used in VH amplification and a primer having a sequence complementary to a mouse κ constant region is used as a 3'-primer used in VL amplification.

```
5'-primer (F primer):
5'-cgactggagcacgaggacactga-3'        (SEQ ID NO: 15)

3'-primer (R primer):
VH: 5'-gccagtggatagacagatgg-3'       (SEQ ID NO: 16)

VL: 5'-gatggatacagttggtgcagc-3'      (SEQ ID NO: 17)
```

Using each of the aforementioned primers, PCR was carried out with the following composition of a reaction solution, under the following reaction conditions.

<<Composition of Reaction Solution>>

| | |
|---|---|
| Template cDNA: | 1.5 µL |
| 10 × ThermalAce PCR buffer: | 5 µL |
| 2 mM dNTP: | 5 µL |
| ThermalAce polymerase: | 0.5 µL |
| F primer (10 µM): | 3 µL |
| R primer (10 µM): | 1.5 µL |
| Sterilized water: | 33.5 µL |
| Total: | 50 µL |

<<Reaction Conditions>>

One cycle consisting of "heat denaturation/dissociation: 94° C. (10 sec) → Annealing: 55° C. (10 sec) → Synthesis/elongation: 72° C. (60 sec)" was repeated 35 times (total 35 cycles).

The cDNA of each of the synthesized VH and VL was subcloned into a pCR4Blunt-TOPO vector (Invitrogen) and the nucleotide sequence thereof was then determined. The nucleotide sequences of multiple VH clones and VL clones were determined and typical nucleotide sequences of the variable regions of mouse H chain and L chain were identified. FIGS. 21 and 22 show the consensus cDNA sequences of the VH and VL of DI-2-14 and the putative amino acid sequences.

Subsequently, to the VH- and VL-coding regions, mouse germ line JH- and Jκ-derived splicing donor signals, each corresponding to the aforementioned regions, were added, respectively. Thereafter, suitable restriction enzyme recognition sequences used for insertion into an animal cell expression vector were further added to both termini. The thus produced VH (FIG. 23) and VL (FIG. 24) genes having functions as exons were inserted into an animal cell expression vector (FIG. 25) having the constant regions of human γ1 chain and κ chain, so as to produce a mouse-human chimeric antibody (DI-2-14 IgG1/K) expression vector (pChDI-2-14).

4. Purification of ChDI-2-14 Antibody Protein

The established NS0 cell line stably producing a ChDI-2-14 antibody was adapted to a serum-free medium (Hybridoma SFM, Invitrogen). Thereafter, a culture supernatant obtained by culturing the cells in the serum-free medium was recovered and an antibody was then purified by an ordinary method using a Protein A column (GE Healthcare).

FIG. 26 shows a mouse DI-2-14 antibody and a purified ChDI-2-14 antibody, which were applied to SDS-PAGE and were then stained with CBB. In both cases, an approximately 50-kD H chain and an approximately 25-kD L chain were detected under reductive conditions, so that production of a ChDI-2-14 antibody protein was confirmed.

5. Antigen Affinity of Chimeric DI-2-14 Antibody (ChDI-2-14)

The antigen affinity of the purified ChDI-2-14 protein was analyzed by a method using ELISA.

ELISA was carried out in the same manner as described in Example 1, using an ELISA plate on which the purified recombinant hFA-1 protein (0.5 to 1 µg/mL) had been immobilized. Specifically, the ELISA plate was washed with a washing buffer 3 times and it was then blocked using a blocking solution at room temperature for 1 hour (or at 4° C. overnight). Thereafter, the plate was washed with a washing buffer 2 times and a mouse DI-2-14 antibody and a ChDI-2-14 antibody, wherein dilution series were produced using an ELISA buffer, were added to the plate, so that they were allowed to react (at 4° C. overnight). Thereafter, the plate was washed with a washing buffer 3 times and it was then allowed to react with HRP-labeled anti-mouse IgG (final concentration: 1 µg/mL) or HRP-labeled anti-human IgG (final concentration: 1 µg/mL) (both products manufactured by GE Healthcare), which had been diluted with a blocking solution. As a result, the reaction curve of mouse DI-2-14 and the reaction curve of ChDI-2-14 were almost overlapped and EC50 was 10 ng/mL in both cases (FIG. 27).

Moreover, the binding activity of each antibody to a Dlk-1 protein expressed on the surface of a living cell was analyzed by flowcytometry using HEK293-hDlk cells. As a result, as with the results of ELISA, ChDI-2-14 exhibited antigen-binding ability that was equivalent to that of mouse DI-2-14 (FIG. 28).

The above results demonstrated that, since a chimeric DI-2-14 antibody (ChDI-2-14) maintains antigen affinity almost equivalent to a mouse DI-2-14 antibody, the produced chimeric DI-2-14 antibody maintains the strong anti-tumor activity in vivo of the mouse DI-2-14 antibody and thus that the chimeric DI-2-14 antibody can be a therapeutic antibody, a diagnostic antibody, or a detective antibody, which is effective for cancers that express Dlk-1 on the cell surface.

6. Expression of Dlk-1 on Cell Surfaces of Human Liver Cancer, Breast Cancer and Leukemia Cell Lines (FACS)

In order to examine expression of Dlk-1 in human cancer cells more in detail, analysis by flowcytometry using an anti-human Dlk-1 antibody was performed on liver cancer cell lines (7 cell lines), breast cancer cell lines (10 cell lines) and acute myelocytic leukemia (AML) cell lines (7 cell lines).

The used cell lines as listed below were acquired from Japanese Health Sciences Foundation (Health Science Research Resources Bank), ATCC (American Type Culture Collection), ECACC (European Collection of Cell Cultures) and DSMZ (German Collection of Microorganisms and Cell Cultures).

HL-60(ATCC), NB-4 (DSMZ), MV-4-11 (ATCC), KG-1 (ATCC), KG-1a (ATCC), TF-1 (ATCC), CMK-11-5 (Japanese Health Sciences Foundation), HepG2 (Japanese Health Sciences Foundation), C3A/HepG2 (ATCC), Huh-7 (Japanese Health Sciences Foundation), OCUG-1 (Japanese Health Sciences Foundation), HLE (Japanese Health Sciences Foundation), HLF (Human Science Promotion Corporation), SK-HEP-1 (ATCC), HCC1143 (ATCC), JIMT-1 (DSMZ), ZR-75-1 (ATCC), MDA-MB-415 (ATCC), BT549 (ATCC), BT-474 (ATCC), MDA-MB-231 (ATCC), DU4475 (ATCC), T47D (ATCC) and MDA-MB-468 (ATCC)

In the case of the liver cancer cell lines, expression of Dlk-1 on the cell surface was confirmed in all the used 7 cell lines (FIG. 29). In the case of the breast cancer cell lines, among the used 10 types of cell lines, strong expression of Dlk-1 was confirmed in HCC1143 cells and JIMT-1 cells (FIG. 30) and even in the remaining 8 types of cell lines, expression of Dlk-1 was confirmed on the cell surface, although the expression level was low (FIG. 30). In the case of the AML cell lines, among the used 7 types of cell lines, expression of Dlk-1 on the cell surface was confirmed in 4 types of cell lines such as CMK-11-5 cells, TF-1 cells, MV-4-11 cells and NB-4 cells (FIG. 31).

EXAMPLE 3

Angiogenesis-Inhibiting Effect of DI-2-14 Antibody (Mouse Anti-Human Dlk-1 Monoclonal Antibody, Clone DI-2-14) in Vivo
<Method>
(1) Immunohistostaining Using Huh-7-hdlk cell cancer-bearing mice, cancer tissues were excised from each of a mouse IgG administration group (a control group: 2 mice) and a DI-2-14 administration group (4 mice). The cancer tissues were embedded into an O.C.T compound (Tissue-Tek) and a fresh frozen section (7 µm) was produced. The section was fixed at room temperature with 2.5% glutaraldehyde/PBS for 15 minutes and then with 0.5% Triton X-100/PBS for 3 minutes. It was then washed with PBS at room temperature for 5 minutes, 3 times. Subsequently, the section was treated at room temperature for 5 minutes using a solution produced by adding a hydrogen peroxide solution to methanol to a final concentration of 0.3%, so as to remove endogenous peroxidase activity. Thereafter, the slide was washed with PBS, 0.1% Tween/PBS and 0.02% Tween/PBS in this order, at room temperature for 5 minutes for each washing solution. In accordance to the protocols of M.O.M.™ Immunodetection Kit (VECTOR), a blocking operation was carried out using M.O.M.™ mouse Ig Blocking Reagent, to block nonspecific binding sites in the tissues. Thereafter, the slide was washed with PBS at room temperature for 2 minutes 2 times. It was then reacted with M.O.M.™ Diluent at room temperature for 5 minutes. Since tumor vessel in the formed Huh-7-hdlk cell-derived tumor was derived from mouse vascular endothelial cells, an anti-mouse Flk-1/VEGF-R2 antibody (final concentration: 2 µg/ml) diluted with M.O.M.™ mouse Ig Blocking Reagent was reacted with it at room temperature for 30 minutes and the slide was then washed with PBS at room temperature for 2 minutes 2 times. Subsequently, a biotinylated anti-rat IgG antibody diluted 100-fold with M.O.M.™ Diluent was allowed to react with the reaction product at room temperature for 10 minutes. After the reaction product was washed with PBS for 2 minutes 2 times, immunohistostaining was carried out according to Immunohistostaining method as described in 11 above.

(2) RT-PCR

The term "RT-PCR" is used in the present example to mean a reaction in which cDNA synthesis from the extracted RNA and PCR using the cDNA as a template were carried out, separately.

Using Huh-7-hdlk cell cancer-bearing mice, cancer tissues were extracted from each of a mouse IgG administration group (a control group: 7 mice) and a DI-2-14 administration group (7 mice). Thereafter, RNA was extracted from the cancer tissues, using a Trizol reagent (Invitrogen). Subsequently, using 1$^{st}$ strand cDNA synthesis kit (GE Healthcare), 1$^{st}$ strand cDNA was synthesized according to the protocols included with the kit.

Using the synthesized 1$^{st}$ strand cDNA as a template, expression of a gene of mouse Flk-1/VEGF-R2 (Genbank accession No. X70842) used as a tumor vascular endothelial cell marker in the cancer tissues excised from each of the mouse IgG administration group (the control group: 7 mice) and the DI-2-14 administration group (7 mice) was analyzed by the PCR method.

The following PCR primers were used (PCR amplification product: 336 bp).

```
F primer:
5'-ctt-tac-tct-ccc-cag-tta-ca-3'   (SEQ ID NO: 18)

R primer:
5'-ctt-tct-att-gtc-aag-gtg-ct-3'   (SEQ ID NO: 19)
```

Using the aforementioned primers, PCR was carried out with the following composition of a reaction solution under the following reaction conditions.

<<Composition of Reaction Solution>>

| | |
|---|---|
| Template DNA: | 1 µL |
| 10 × PCR buffer: | 5 µL |
| 2.5 mM dNTP: | 4 µL |
| Taq DNA polymerase: | 0.5 µL |
| F primer (10 µM): | 1 µL |
| R primer (10 µM): | 1 µL |
| Sterilized water: | 37.5 µL |
| Total: | 50 µL |

<<Reaction Conditions>>

After performing denaturation at 95° C. (3 minutes), one cycle consisting of "heat denaturation/dissociation: 95° C. (60 sec) → Annealing: 55° C. (60 sec) → Synthesis/elongation: 72° C. (60 sec)" was repeated 35 times (total 35 cycles).

As an internal control, GAPDH (human GAPDH: NM_002046; mouse GAPDH: NM_008084, NM_001001303, XM_001003314, XM_988853, XM_990238) was used. As PCR primers used in amplification of GAPDH, the following primers were used (PCR amplification product: 452 bp). These primers enable amplification in both cases of using either human GAPDH or mouse GAPDH as a template.

```
F primer:
5'-acc-aca-gtc-cat-gcc-atc-ac-3'   (SEQ ID NO: 20)

R primer:
5'-tcc-acc-acc-ctg-ttg-ctg-ta-3'   (SEQ ID NO: 21)
```

The amplification of GAPDH was carried out in the same PCR condition of the above described Flk-1/VEGFR-2.

In order to quantify PCR products, the products were first separated by 1.2% agarose gel electrophoresis and it was then stained with ethidium bromide. Thereafter, the obtained electrophoretic image was captured by a scanner, the PCR product was then quantified with NIH Image and a graph was then product based on the ratio of Flk-1/GAPDH.

<Results>

As shown in FIG. 32, the number of tumor vascular endothelial cells, whose nucleus was confirmed by nuclear staining with hematoxylin in 8 to 13 visual fields (an objective lens of 200-fold) from each of an IgG administration group (20 mg/kg body weight) (2 mice) and a DI-2-14 administration group (20 mg/kg body weight) (4 mice), and which were positive to Flk-1/VEGF-R2, was counted (the IgG administration group: total 25 visual fields; the DI-2-14 administration group: total 35 visual fields) and the number of tumor vascular cells per visual field was counted. As a result, the number of such cells was found to be 112.0±63.6 (Flk-1 positive cell number/visual field) in the IgG administration group, whereas the number of such cells was found to be 36.3±2.2 (Flk-1-positive cell number/visual field) in the DI-2-14 administration group. Thus, the number of tumor vascular cells was significantly small (P<0.01) and thus it was demonstrated that tumor angiogenesis was inhibited by administration of DI-2-14.

Moreover, in another experiment, Huh-7-hDlk-1 cell cancer-bearing mice were also used and expression of a gene of Flk-1/VEGF-R2 acting as a marker gene specific for tumor vascular endothelial cells in the tumor formed from each of an IgG administration group (20 mg/kg body weight, N=7) and a DI-2-14 administration group (20 mg/kg body weight, N=7) was semi-quantitatively analyzed by RT-PCR. As a result, as shown in FIG. 33, expression of the Flk-1/VEGF-R2 gene was decreased in the tumor from the DI-2-14 administration group. This result demonstrated that tumor angiogenesis was inhibited by administration of DI-2-14.

<Consideration>

It has been known that tumor angiogenesis is essential for formation of cancer. As a cancer therapeutic antibody that mainly acts to inhibit such tumor angiogenesis, an anti-VEGF antibody (Avastin) has been known. To date, information regarding the angiogenesis or angiogenesis-inhibiting activity of Dlk-1 and an anti-Dlk-1 antibody has not been provided. In addition, with regard to the functions of Dlk-1, the control of differentiation of adipose cells and acceleration of the growth of glioma cells or leukemia cells by stable introduction of the Dlk-1 gene have been reported. However, it has been impossible to predict, based on the previous information, the fact that an anti-Dlk-1 antibody (DI-2-14) has tumor angiogenesis-inhibiting activity. The present example showed at least one action mechanism of the anti-tumor activity in vivo of the DI-2-14 antibody.

INDUSTRIAL APPLICABILITY

According to the present invention, there can be provided an anti-human Dlk-1 antibodies having anti-tumor activity and in particular, an anti-human Dlk-1 monoclonal antibodies having anti-tumor activity in vivo. Moreover, the present invention provides a hybridomas that produce the aforementioned antibodies, a complex of the aforementioned antibodies and various types of agents, a pharmaceutical composition for diagnosing or treating a tumor, a method for detecting tumor and a kit for detecting or diagnosing a tumor.

The invention claimed is:

1. An isolated antibody against human Dlk-1, which has anti-tumor activity in vivo, wherein the tumor is human liver cancer or human neuroblastoma, and wherein the amino acid sequences of CDRs 1 to 3 of the H chain V region of the antibody are the amino acid sequences as shown in SEQ ID NOS: 30 to 32, respectively and the amino acid sequences of CDRs 1 to 3 of the L chain V region of the antibody are the amino acid sequences as shown in SEQ ID NOS: 33 to 35, respectively.

2. The antibody according to claim 1, wherein the anti-tumor activity is tumor angiogenesis-inhibiting activity.

3. The antibody according to claim 1, which is a monoclonal antibody.

4. The antibody according to claim 1, wherein the antibody is a genetically recombinant antibody.

5. The antibody according to claim 4, wherein the genetically recombinant antibody is a chimeric antibody or a humanized antibody.

6. The antibody according to claim 5, wherein the amino acid sequence of the H chain V region of the chimeric antibody comprises the amino acid sequence as shown in SEQ ID NO: 23 and the amino acid sequence of the L chain V region of the chimeric antibody comprises the amino acid sequence as shown in SEQ ID NO: 25.

7. The antibody according to claim 1, which binds to a site, to which a monoclonal antibody produced by a hybridoma having accession no. FERM BP-10899 binds.

8. The antibody according to claim 1, which binds to at least a portion of a region comprising amino acids at positions 92 to 167 in the amino acid sequence of human Dlk-1 as shown in SEQ ID NO: 2.

9. An isolated antibody fragment from the antibody according to claim 1, wherein the antibody fragment comprises the amino acid sequences as shown in SEQ ID NOS: 30 to 32 and the amino acid sequences as shown in SEQ ID NOS: 33 to 35.

10. The antibody fragment according to claim 9, which comprises the amino acid sequence as shown in SEQ ID NO: 23.

11. The antibody fragment according to claim 9, which comprises the amino acid sequence as shown in SEQ ID NO: 25.

12. A monoclonal antibody produced by a hybridoma selected from the group consisting of a hybridoma having accession no. FERM BP-10707, a hybridoma having accession no. FERM BP-10899 and a hybridoma having accession no. FERM BP-10900.

* * * * *

UNITED STATES PATENT AND TRADEMARK OFFICE
CERTIFICATE OF CORRECTION

PATENT NO. : 8,227,578 B2
APPLICATION NO. : 12/514230
DATED : July 24, 2012
INVENTOR(S) : Koji Nakamura and Rie Tajima It is certified that error appears in the above-identified patent and that said Letters Patent is hereby corrected as shown below:

Title Page, Item (73) Assignee should read -- LIVTECH INC., Tokyo (JP) --

Signed and Sealed this
Twentieth Day of November, 2012

David J. Kappos
*Director of the United States Patent and Trademark Office*

```
                              SEQUENCE LISTING

<160> NUMBER OF SEQ ID NOS: 35

<210> SEQ ID NO 1
<211> LENGTH: 1532
<212> TYPE: DNA
<213> ORGANISM: Homo sapiens
<220> FEATURE:
<221> NAME/KEY: CDS
<222> LOCATION: (154)..(1305)

<400> SEQUENCE: 1
gagagcgcag cgcgcagccc ggtgcagccc tggctttccc ctcgctgcgc gcccgcgccc      60
cctttcgcgt ccgcaaccag aagcccagtg cggcgccagg agccgacccc gcgcccgcac     120
cgctcccggg accgcgaccc cggccgccca gag atg acc gcg acc gaa gcc ctc     174
                                     Met Thr Ala Thr Glu Ala Leu
                                       1               5 ctg cgc gtc ctc ttg ctc ctg ctg gct ttc ggc cac agc acc tat ggg       222
Leu Arg Val Leu Leu Leu Leu Leu Ala Phe Gly His Ser Thr Tyr Gly
         10                  15                  20 gct gaa tgc ttc ccg gcc tgc aac ccc caa aat gga ttc tgc gag gat       270
Ala Glu Cys Phe Pro Ala Cys Asn Pro Gln Asn Gly Phe Cys Glu Asp
     25                  30                  35 gac aat gtt tgc agg tgc cag cct ggc tgg cag ggt ccc ctt tgt gac       318
Asp Asn Val Cys Arg Cys Gln Pro Gly Trp Gln Gly Pro Leu Cys Asp
 40                  45                  50                  55 cag tgc gtg acc tct ccc ggc tgc ctt cac gga ctc tgt gga gaa ccc       366
Gln Cys Val Thr Ser Pro Gly Cys Leu His Gly Leu Cys Gly Glu Pro
                 60                  65                  70 ggg cag tgc att tgc acc gac ggc tgg gac ggg gag ctc tgt gat aga       414
Gly Gln Cys Ile Cys Thr Asp Gly Trp Asp Gly Glu Leu Cys Asp Arg
             75                  80                  85 gat gtt cgg gcc tgc tcc tcg gcc ccc tgt gcc aac aac ggg acc tgc       462
Asp Val Arg Ala Cys Ser Ser Ala Pro Cys Ala Asn Asn Gly Thr Cys
         90                  95                 100 gtg agc ctg gac gat ggc ctc tat gaa tgc tcc tgt gcc ccc ggg tac       510
Val Ser Leu Asp Asp Gly Leu Tyr Glu Cys Ser Cys Ala Pro Gly Tyr
    105                 110                 115 tcg gga aag gac tgc cag aaa aag gac ggg ccc tgt gtg atc aac ggc       558
Ser Gly Lys Asp Cys Gln Lys Lys Asp Gly Pro Cys Val Ile Asn Gly
120                 125                 130                 135 tcc ccc tgc cag cac gga ggc acc tgc gtg gat gat gag ggc cgg gcc       606
Ser Pro Cys Gln His Gly Gly Thr Cys Val Asp Asp Glu Gly Arg Ala
                140                 145                 150 tcc cat gcc tcc tgc ctg tgc ccc cct ggc ttc tca ggc aat ttc tgc       654
Ser His Ala Ser Cys Leu Cys Pro Pro Gly Phe Ser Gly Asn Phe Cys
            155                 160                 165 gag atc gtg gcc aac agc tgc acc ccc aac cca tgc gag aac gac ggc       702
Glu Ile Val Ala Asn Ser Cys Thr Pro Asn Pro Cys Glu Asn Asp Gly
        170                 175                 180 gtc tgc act gac att ggg ggc gac ttc cgc tgc cgg tgc cca gcc ggc       750
Val Cys Thr Asp Ile Gly Gly Asp Phe Arg Cys Arg Cys Pro Ala Gly
    185                 190                 195
```

-continued

| | | |
|---|---|---|
| ttc atc gac aag acc tgc agc cgc ccg gtg acc aac tgc gcc agc agc<br>Phe Ile Asp Lys Thr Cys Ser Arg Pro Val Thr Asn Cys Ala Ser Ser<br>200                          205                       210                        215 | 798 |
| ccg tgc cag aac ggg ggc acc tgc ctg cag cac acc cag gtg agc tac<br>Pro Cys Gln Asn Gly Gly Thr Cys Leu Gln His Thr Gln Val Ser Tyr<br>                    220                       225                        230 | 846 |
| gag tgt ctg tgc aag ccc gag ttc aca ggt ctc acc tgt gtc aag aag<br>Glu Cys Leu Cys Lys Pro Glu Phe Thr Gly Leu Thr Cys Val Lys Lys<br>235                          240                       245 | 894 |
| cgc gcg ctg agc ccc cag cag gtc acc cgt ctg ccc agc ggc tat ggg<br>Arg Ala Leu Ser Pro Gln Gln Val Thr Arg Leu Pro Ser Gly Tyr Gly<br>          250                       255                       260 | 942 |
| ctg gcc tac cgc ctg acc cct ggg gtg cac gag ctg ccg gtg cag cag<br>Leu Ala Tyr Arg Leu Thr Pro Gly Val His Glu Leu Pro Val Gln Gln<br>265                          270                       275 | 990 |
| ccg gag cac cgc atc ctg aag gtg tcc atg aaa gag ctc aac aag aaa<br>Pro Glu His Arg Ile Leu Lys Val Ser Met Lys Glu Leu Asn Lys Lys<br>280                          285                       290                       295 | 1038 |
| acc cct ctc ctc acc gag ggc cag gcc atc tgc ttc acc atc ctg ggc<br>Thr Pro Leu Leu Thr Glu Gly Gln Ala Ile Cys Phe Thr Ile Leu Gly<br>                    300                       305                        310 | 1086 |
| gtg ctc acc agc ctg gtg gtg ctg ggc act gtg ggt atc gtc ttc ctc<br>Val Leu Thr Ser Leu Val Val Leu Gly Thr Val Gly Ile Val Phe Leu<br>               315                       320                       325 | 1134 |
| aac aag tgc gag acc tgg gtg tcc aac ctg cgc tac aac cac atg ctg<br>Asn Lys Cys Glu Thr Trp Val Ser Asn Leu Arg Tyr Asn His Met Leu<br>330                          335                       340 | 1182 |
| cgg aag aag aag aac ctg ctg ctt cag tac aac agc ggg gag gac ctg<br>Arg Lys Lys Lys Asn Leu Leu Leu Gln Tyr Asn Ser Gly Glu Asp Leu<br>345                          350                       355 | 1230 |
| gcc gtc aac atc atc ttc ccc gag aag atc gac atg acc acc ttc agc<br>Ala Val Asn Ile Ile Phe Pro Glu Lys Ile Asp Met Thr Thr Phe Ser<br>360                          365                       370                       375 | 1278 |
| aag gag gcc ggc gac gag gag atc taa gcagcgttcc cacagccccc<br>Lys Glu Ala Gly Asp Glu Glu Ile<br>               380 | 1325 |
| tctagattct tggagttccg cagagcttac tatacgcggt ctgtcctaat ctttgtggtg | 1385 |
| ttcgctatct cttgtgtcaa atctggtgaa cgctacgctt acatatattg tctttgtgct | 1445 |
| gctgtgtgac aaacgcaatg caaaaacaat cctctttctc tctcttaatg catgatacag | 1505 |
| aataataata agaatttcat ctttaaa | 1532 |

<210> SEQ ID NO 2
<211> LENGTH: 383
<212> TYPE: PRT
<213> ORGANISM: Homo sapiens

<400> SEQUENCE: 2

Met Thr Ala Thr Glu Ala Leu Leu Arg Val Leu Leu Leu Leu Leu Ala
1                    5                        10                       15

Phe Gly His Ser Thr Tyr Gly Ala Glu Cys Phe Pro Ala Cys Asn Pro
                  20                       25                       30

Gln Asn Gly Phe Cys Glu Asp Asp Asn Val Cys Arg Cys Gln Pro Gly
               35                       40                       45

Trp Gln Gly Pro Leu Cys Asp Gln Cys Val Thr Ser Pro Gly Cys Leu
        50                       55                       60

His Gly Leu Cys Gly Glu Pro Gly Gln Cys Ile Cys Thr Asp Gly Trp
65                    70                       75                       80

Asp Gly Glu Leu Cys Asp Arg Asp Val Arg Ala Cys Ser Ser Ala Pro
                85                  90                  95

Cys Ala Asn Asn Gly Thr Cys Val Ser Leu Asp Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
            165                 170                 175

Asn Pro Cys Glu Asn Asp Gly Val Cys Thr Asp Ile Gly Gly Asp Phe
        180                 185                 190

Arg Cys Arg Cys Pro Ala Gly Phe Ile Asp Lys Thr Cys Ser Arg Pro
    195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
            245                 250                 255

Arg Leu Pro Ser Gly Tyr Gly Leu Ala Tyr Arg Leu Thr Pro Gly Val
        260                 265                 270

His Glu Leu Pro Val Gln Gln Pro Glu His Arg Ile Leu Lys Val Ser
    275                 280                 285

Met Lys Glu Leu Asn Lys Lys Thr Pro Leu Leu Thr Glu Gly Gln Ala
290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
            325                 330                 335

Leu Arg Tyr Asn His Met Leu Arg Lys Lys Lys Asn Leu Leu Leu Gln
        340                 345                 350

Tyr Asn Ser Gly Glu Asp Leu Ala Val Asn Ile Ile Phe Pro Glu Lys
    355                 360                 365

Ile Asp Met Thr Thr Phe Ser Lys Glu Ala Gly Asp Glu Glu Ile
370                 375                 380

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
cgcgtccgca accagaagcc c                                        21

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4
ctcgaggtgc tccggctgct gcaccggc                                 28

```
<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
gcggccggct gaatgcttcc cggcc                                           25

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
tctagagagg ctgttggcca cgatctcgc                                       29

<210> SEQ ID NO 7
<211> LENGTH: 25
<212> TYPE: DNA
<213> ORGANISM: Artificial
<220> FEATURE:
<223> OTHER INFORMATION: primer

<400> SEQUENCE: 7
gcggccggct gaatgcttcc cggcc                                           25

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
tctagacccg tcctttttct ggcagtcc                                        28

<210> SEQ ID NO 9
<211> LENGTH: 25
<212> TYPE: DNA
<213> ORGANISM: Artificial
<220> FEATURE:
<223> OTHER INFORMATION: primer

<400> SEQUENCE: 9
gcggccggct gaatgcttcc cggcc                                           25

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
tctagaggcc cgaacatctc tatcac                                          26

<210> SEQ ID NO 11
<211> LENGTH: 27
<212> TYPE: DNA
<213> ORGANISM: Artificial
<220> FEATURE:
<223> OTHER INFORMATION: primer
```

```
<400> SEQUENCE: 11
gcggccgcaa aaaggacggg ccctgtg                                    27

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
gcgtatagta agctctgcgg                                            20

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
caggcagcgg ccgcgagatc gtggccaac                                  29

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
gcgtatagta agctctgcgg                                            20

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
cgactggagc acgaggacac tga                                        23

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gccagtggat agacagatgg                                            20

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
gatggataca gttggtgcag c                                          21

<210> SEQ ID NO 18
<211> LENGTH: 20
```

```
<212> TYPE: DNA
<213> ORGANISM: Artificial
<220> FEATURE:
<223> OTHER INFORMATION: primer

<400> SEQUENCE: 18
ctttactctc cccagttaca                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ctttctattg tcaaggtgct                                               20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
accacagtcc atgccatcac                                               20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
tccaccaccc tgttgctgta                                               20

<210> SEQ ID NO 22
<211> LENGTH: 411
<212> TYPE: DNA
<213> ORGANISM: Mus musculus
<220> FEATURE:
<221> NAME/KEY: CDS
<222> LOCATION: (1)..(411)

<400> SEQUENCE: 22 atg aaa tgc agc tgg gtt atc ttc ttc ctg atg gca gtg gtt aca ggg     48
Met Lys Cys Ser Trp Val Ile Phe Phe Leu Met Ala Val Val Thr Gly
 1               5                  10                  15 gtc aat tca gag gtt cag ctg cag cag tct ggg gca gag ctt gtg aag     96
Val Asn Ser Glu Val Gln Leu Gln Gln Ser Gly Ala Glu Leu Val Lys
             20                  25                  30 cca ggg gcc tca gtc aag ttg tcc tgc aca gct tct ggc ttc aac att    144
Pro Gly Ala Ser Val Lys Leu Ser Cys Thr Ala Ser Gly Phe Asn Ile
         35                  40                  45 aga gac acc tat ata cac tgg gtg aag cag agg cct gag cag ggc ctg    192
Arg Asp Thr Tyr Ile His Trp Val Lys Gln Arg Pro Glu Gln Gly Leu
     50                  55                  60 gag tgg att gga agg att gat cct ccg aat ggt aat ctt aaa tat gac    240
Glu Trp Ile Gly Arg Ile Asp Pro Pro Asn Gly Asn Leu Lys Tyr Asp
 65                  70                  75                  80 ccg aag ttc cag ggc aag gcc act ata aca gca gac aca tcc tcc aac    288
Pro Lys Phe Gln Gly Lys Ala Thr Ile Thr Ala Asp Thr Ser Ser Asn
                 85                  90                  95
```

```
aca gcc tac ctg cag ttc agc agc ctg aca tct gag gac act gcc gtc    336
Thr Ala Tyr Leu Gln Phe Ser Ser Leu Thr Ser Glu Asp Thr Ala Val
        100                 105                 110 tat tac tgt gca agg tct gat ggt tac tcc ttt gct tac tgg ggc caa    384
Tyr Tyr Cys Ala Arg Ser Asp Gly Tyr Ser Phe Ala Tyr Trp Gly Gln
            115                 120                 125 ggg act ctg gtc act gtc tct gca gcc                                411
Gly Thr Leu Val Thr Val Ser Ala Ala
    130                 135
```

<210> SEQ ID NO 23
<211> LENGTH: 137
<212> TYPE: PRT
<213> ORGANISM: Mus musculus

<400> SEQUENCE: 23

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Arg Asp Thr Tyr Ile His Trp Val Lys Gln Arg Pro Glu Gln Gly Leu
    50                  55                  60

Glu Trp Ile Gly Arg Ile Asp Pro Pro Asn Gly Asn Leu Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Phe Ser Ser Leu Thr Ser Glu Asp Thr Ala Val
            100                 105                 110

Tyr Tyr Cys Ala Arg Ser Asp Gly Tyr Ser Phe Ala Tyr Trp Gly Gln
        115                 120                 125

Gly Thr Leu Val Thr Val Ser Ala Ala
    130                 135
```

<210> SEQ ID NO 24
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 24

```
atg agg tgc cta gct gag ttc ctg ggg ctg ctt gtg ctc tgg atc cct    48
Met Arg Cys Leu Ala Glu Phe Leu Gly Leu Leu Val Leu Trp Ile Pro
1               5                   10                  15 gga gcc att ggg gat att gtg atg act cag gct gca ccc tct gta cct    96
Gly Ala Ile Gly Asp Ile Val Met Thr Gln Ala Ala Pro Ser Val Pro
            20                  25                  30 gtc act cct gga gag tca gta tcc atc tcc tgc agg tct agt aag agt   144
Val Thr Pro Gly Glu Ser Val Ser Ile Ser Cys Arg Ser Ser Lys Ser
        35                  40                  45 ctc ctg cat agt aat ggc aac act tac ttg tat tgg ttc ctg cag agg   192
Leu Leu His Ser Asn Gly Asn Thr Tyr Leu Tyr Trp Phe Leu Gln Arg
    50                  55                  60 cca ggc cag tct cct cag ctc ctg ata tat cgg atg tcc aac ctt gcc   240
Pro Gly Gln Ser Pro Gln Leu Leu Ile Tyr Arg Met Ser Asn Leu Ala
65                  70                  75                  80 tca gga gtc cca gac agg ttc agt ggc agt ggg tca gga act gct ttc   288
Ser Gly Val Pro Asp Arg Phe Ser Gly Ser Gly Ser Gly Thr Ala Phe
```

```
aca ctg aga atc agt aga gtg gag gct gag gat gtg ggt gtt tat tac       336
Thr Leu Arg Ile Ser Arg Val Glu Ala Glu Asp Val Gly Val Tyr Tyr
            100                 105                 110 tgt atg caa cat gta gaa tat cca ttc acg ttc ggc tcg ggg aca aag       384
Cys Met Gln His Val Glu Tyr Pro Phe Thr Phe Gly Ser Gly Thr Lys
        115                 120                 125 ttg gaa ata aaa                                                       396
Leu Glu Ile Lys
    130

<210> SEQ ID NO 25
<211> LENGTH: 132
<212> TYPE: PRT
<213> ORGANISM: Mus musculus

<400> SEQUENCE: 25

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Val Glu Tyr Pro Phe Thr Phe Gly Ser Gly Thr Lys
        115                 120                 125

Leu Glu Ile Lys
    130

<210> SEQ ID NO 26
<211> LENGTH: 442
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (13)..(420)

<400> SEQUENCE: 26
actagtacca cc atg aaa tgc agc tgg gtt atc ttc ttc ctg atg gca gtg    51
             Met Lys Cys Ser Trp Val Ile Phe Phe Leu Met Ala Val
             1               5                   10 gtt aca ggg gtc aat tca gag gtt cag ctg cag cag tct ggg gca gag      99
Val Thr Gly Val Asn Ser Glu Val Gln Leu Gln Gln Ser Gly Ala Glu
        15                  20                  25 ctt gtg aag cca ggg gcc tca gtc aag ttg tcc tgc aca gct tct ggc     147
Leu Val Lys Pro Gly Ala Ser Val Lys Leu Ser Cys Thr Ala Ser Gly
30                  35                  40                  45 ttc aac att aga gac acc tat ata cac tgg gtg aag cag agg cct gag     195
Phe Asn Ile Arg Asp Thr Tyr Ile His Trp Val Lys Gln Arg Pro Glu
                50                  55                  60 cag ggc ctg gag tgg att gga agg att gat cct ccg aat ggt aat ctt     243
Gln Gly Leu Glu Trp Ile Gly Arg Ile Asp Pro Pro Asn Gly Asn Leu
```

```
aaa tat gac ccg aag ttc cag ggc aag gcc act ata aca gca gac aca    291
Lys Tyr Asp Pro Lys Phe Gln Gly Lys Ala Thr Ile Thr Ala Asp Thr
         80                  85                  90 tcc tcc aac aca gcc tac ctg cag ttc agc agc ctg aca tct gag gac    339
Ser Ser Asn Thr Ala Tyr Leu Gln Phe Ser Ser Leu Thr Ser Glu Asp
 95                 100                 105 act gcc gtc tat tac tgt gca agg tct gat ggt tac tcc ttt gct tac    387
Thr Ala Val Tyr Tyr Cys Ala Arg Ser Asp Gly Tyr Ser Phe Ala Tyr
110                 115                 120                 125 tgg ggc caa ggg act ctg gtc act gtc tct gca ggtgagtcct aacttcaagc  440
Trp Gly Gln Gly Thr Leu Val Thr Val Ser Ala
                130                 135 tt                                                                 442

<210> SEQ ID NO 27
<211> LENGTH: 136
<212> TYPE: PRT
<213> ORGANISM: Artificial
<220> FEATURE:
<223> OTHER INFORMATION: Synthetic Construct (recombinant protein)

<400> SEQUENCE: 27

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Arg Asp Thr Tyr Ile His Trp Val Lys Gln Arg Pro Glu Gln Gly Leu
    50                  55                  60

Glu Trp Ile Gly Arg Ile Asp Pro Pro Asn Gly Asn Leu Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Phe Ser Ser Leu Thr Ser Glu Asp Thr Ala Val
            100                 105                 110

Tyr Tyr Cys Ala Arg Ser Asp Gly Tyr Ser Phe Ala Tyr Trp Gly Gln
        115                 120                 125

Gly Thr Leu Val Thr Val Ser Ala
    130                 135

<210> SEQ ID NO 28
<211> LENGTH: 431
<212> TYPE: DNA
<213> ORGANISM: Artificial
<220> FEATURE:
<223> OTHER INFORMATION: recombinant DNA
<220> FEATURE:
<221> NAME/KEY: CDS
<222> LOCATION: (13)..(420)

<400> SEQUENCE: 28
gctagcacca cc atg agg tgc cta gct gag ttc ctg ggg ctg ctt gtg ctc   51
              Met Arg Cys Leu Ala Glu Phe Leu Gly Leu Leu Val Leu
              1               5                   10 tgg atc cct gga gcc att ggg gat att gtg atg act cag gct gca ccc    99
Trp Ile Pro Gly Ala Ile Gly Asp Ile Val Met Thr Gln Ala Ala Pro
            15                  20                  25 tct gta cct gtc act cct gga gag tca gta tcc atc tcc tgc agg tct   147
Ser Val Pro Val Thr Pro Gly Glu Ser Val Ser Ile Ser Cys Arg Ser
```

-continued

```
              30                  35                  40                  45
agt aag agt ctc ctg cat agt aat ggc aac act tac ttg tat tgg ttc         195
Ser Lys Ser Leu Leu His Ser Asn Gly Asn Thr Tyr Leu Tyr Trp Phe
                    50                  55                  60 ctg cag agg cca ggc cag tct cct cag ctc ctg ata tat cgg atg tcc         243
Leu Gln Arg Pro Gly Gln Ser Pro Gln Leu Leu Ile Tyr Arg Met Ser
            65                  70                  75 aac ctt gcc tca gga gtc cca gac agg ttc agt ggc agt ggg tca gga         291
Asn Leu Ala Ser Gly Val Pro Asp Arg Phe Ser Gly Ser Gly Ser Gly
                80                  85                  90 act gct ttc aca ctg aga atc agt aga gtg gag gct gag gat gtg ggt         339
Thr Ala Phe Thr Leu Arg Ile Ser Arg Val Glu Ala Glu Asp Val Gly
            95                  100                 105 gtt tat tac tgt atg caa cat gta gaa tat cca ttc acg ttc ggc tcg         387
Val Tyr Tyr Cys Met Gln His Val Glu Tyr Pro Phe Thr Phe Gly Ser
110                 115                 120                 125 ggg aca aag ttg gaa ata aaa cgt aag tag act tttgcgaatt c               431
Gly Thr Lys Leu Glu Ile Lys Arg Lys     Thr
                    130                         135
```

<210> SEQ ID NO 29
<211> LENGTH: 134
<212> TYPE: PRT
<213> ORGANISM: Artificial
<220> FEATURE:
<223> OTHER INFORMATION: Synthetic Construct (recombinant protein)

<400> SEQUENCE: 29

```
Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Val Glu Tyr Pro Phe Thr Phe Gly Ser Gly Thr Lys
        115                 120                 125

Leu Glu Ile Lys Arg Lys
    130
```

<210> SEQ ID NO 30
<211> LENGTH: 5
<212> TYPE: PRT
<213> ORGANISM: Mus musculus

<400> SEQUENCE: 30

```
Asp Thr Tyr Ile His
1               5
```

<210> SEQ ID NO 31
<211> LENGTH: 17
<212> TYPE: PRT
<213> ORGANISM: Mus musculus

```
<400> SEQUENCE: 31

Arg Ile Asp Pro Pro Asn Gly Asn Leu Lys Tyr Asp Pro Lys Phe Gln
1               5                   10                  15

Gly

<210> SEQ ID NO 32
<211> LENGTH: 8
<212> TYPE: PRT
<213> ORGANISM: Mus musculus

<400> SEQUENCE: 32

Ser Asp Gly Tyr Ser Phe Ala Tyr
1               5

<210> SEQ ID NO 33
<211> LENGTH: 16
<212> TYPE: PRT
<213> ORGANISM: Mus musculus

<400> SEQUENCE: 33

Arg Ser Ser Lys Ser Leu Leu His Ser Asn Gly Asn Thr Tyr Leu Tyr
1               5                   10                  15

<210> SEQ ID NO 34
<211> LENGTH: 7
<212> TYPE: PRT
<213> ORGANISM: Mus musculus

<400> SEQUENCE: 34

Arg Met Ser Asn Leu Ala Ser
1               5

<210> SEQ ID NO 35
<211> LENGTH: 9
<212> TYPE: PRT
<213> ORGANISM: Mus musculus

<400> SEQUENCE: 35

Met Gln His Val Glu Tyr Pro Phe Thr
1               5
```